(12) United States Patent
Kim et al.

(10) Patent No.: US 11,751,470 B2
(45) Date of Patent: Sep. 5, 2023

(54) COMPOUND AND ORGANIC LIGHT EMITTING DEVICE COMPRISING THE SAME

(71) Applicant: LG Chem, Ltd., Seoul (KR)

(72) Inventors: Yongwook Kim, Daejeon (KR); Young Kwang Kim, Daejeon (KR); Beomshin Cho, Daejeon (KR); Jaesoon Bae, Daejeon (KR); Jaechol Lee, Daejeon (KR); Yebyeol Kim, Daejeon (KR)

(73) Assignee: LG Chem, Ltd.

( * ) Notice: Subject to any disclaimer, the term of this patent is extended or adjusted under 35 U.S.C. 154(b) by 449 days.

(21) Appl. No.: 17/057,965

(22) PCT Filed: Sep. 30, 2019

(86) PCT No.: PCT/KR2019/012738
§ 371 (c)(1),
(2) Date: Nov. 23, 2020

(87) PCT Pub. No.: WO2020/080702
PCT Pub. Date: Apr. 23, 2020

(65) Prior Publication Data
US 2021/0234105 A1    Jul. 29, 2021

(30) Foreign Application Priority Data

Oct. 16, 2018 (KR) .......... 10-2018-0123388

(51) Int. Cl.
*C07C 15/14* (2006.01)
*H10K 85/40* (2023.01)
(Continued)

(52) U.S. Cl.
CPC .............. *H10K 85/40* (2023.02); *C07C 15/14* (2013.01); *C07F 7/0812* (2013.01); *C09K 11/06* (2013.01);
(Continued)

(58) Field of Classification Search
None
See application file for complete search history.

(56) References Cited

U.S. PATENT DOCUMENTS 9,773,987 B2    9/2017   Jung et al.
2004/0251816 A1   12/2004  Leo et al.
(Continued)

FOREIGN PATENT DOCUMENTS

CN    104768940 A    7/2015
CN    106206964 A    12/2016
(Continued)

OTHER PUBLICATIONS

International Search Report for Application PCT/KR2019/012738 dated Jan. 15, 2020, 2 pages.

*Primary Examiner* — Robert S Loewe
(74) *Attorney, Agent, or Firm* — Lerner David LLP

(57) ABSTRACT

There are provided a novel compound represented by the following Chemical Formula 1 and an organic light emitting device using the same,

[Chemical Formula 1]

(Continued)

-continued

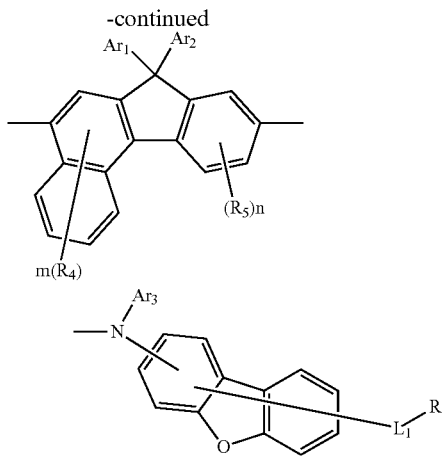

wherein m, n, R, $R_4$, $R_5$, $L_1$ and $Ar_1$ to $Ar_3$ are defined therein.

16 Claims, 1 Drawing Sheet

(51) Int. Cl.
*C07F 7/08* (2006.01)
*C09K 11/06* (2006.01)
*H10K 85/60* (2023.01)
*H10K 50/11* (2023.01)
*H10K 50/15* (2023.01)
*H10K 50/16* (2023.01)
*H10K 50/17* (2023.01)
*H10K 101/10* (2023.01)

(52) U.S. Cl.
CPC ....... *H10K 85/626* (2023.02); *C07C 2603/24* (2017.05); *C09K 2211/1007* (2013.01); *C09K 2211/1011* (2013.01); *C09K 2211/1018* (2013.01); *H10K 50/11* (2023.02); *H10K 50/15* (2023.02); *H10K 50/16* (2023.02); *H10K 50/17* (2023.02); *H10K 85/622* (2023.02); *H10K 85/633* (2023.02); *H10K 85/636* (2023.02); *H10K 85/6574* (2023.02); *H10K 2101/10* (2023.02)

(56) References Cited

U.S. PATENT DOCUMENTS

| | | | |
|---|---|---|---|
| 2014/0131681 | A1 | 5/2014 | Ito et al. |
| 2014/0209869 | A1 | 7/2014 | Jung et al. |
| 2015/0034915 | A1 | 2/2015 | Kim et al. |
| 2016/0104847 | A1 | 4/2016 | Xia et al. |
| 2016/0149139 | A1* | 5/2016 | Xia ............. H10K 85/40 252/301.16 |
| 2016/0351816 | A1 | 12/2016 | Kim et al. |
| 2016/0351817 | A1 | 12/2016 | Kim et al. |
| 2017/0309827 | A1 | 10/2017 | Zeng et al. |
| 2017/0317286 | A1* | 11/2017 | Ito ............. H10K 85/622 |
| 2018/0083209 | A1 | 3/2018 | Ueno et al. |
| 2018/0248130 | A1 | 8/2018 | Shin et al. |

FOREIGN PATENT DOCUMENTS

| | | |
|---|---|---|
| CN | 106206999 A | 12/2016 |
| CN | 107868097 A | 4/2018 |
| KR | 20000051826 A | 8/2000 |
| KR | 20140096659 A | 8/2014 |
| KR | 20150014778 A | 2/2015 |
| KR | 20150079664 A | 7/2015 |
| KR | 20160040198 A | 4/2016 |
| KR | 20160043505 A | 4/2016 |
| KR | 20160141360 A | 12/2016 |
| KR | 20160141361 A | 12/2016 |
| KR | 20170121575 A | 11/2017 |
| KR | 20180032735 A | 4/2018 |
| KR | 20180099965 A | 9/2018 |
| WO | 2003012890 A2 | 2/2003 |
| WO | WO-2014065391 A1 * | 5/2014 ........... C07B 59/002 |

* cited by examiner

[FIG. 1]
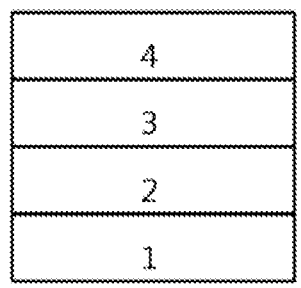
[FIG. 2]
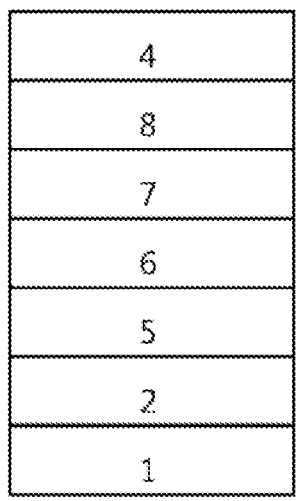

COMPOUND AND ORGANIC LIGHT EMITTING DEVICE COMPRISING THE SAME

CROSS-REFERENCE TO RELATED APPLICATIONS

This application is a national phase entry under 35 U.S.C. § 371 of International Application No. PCT/KR2019/012738 filed Sep. 30, 2019, which claims priority from Korean Patent Application No. 10-2018-0123388 filed Oct. 16, 2018, all of which are incorporated herein by reference.

TECHNICAL FIELD

The present disclosure relates to a novel compound and an organic light emitting device using the same.

BACKGROUND OF ART

In general, organic light emission refers to a phenomenon wherein electric energy is converted into light energy using organic material. Organic light emitting devices using organic light emission phenomenon have wide viewing angle, excellent contrast, rapid response time, and excellent luminance, driving voltage and response speed properties, and thus, many studies are being progressed.

An organic light emitting device generally has a structure comprising an anode, a cathode, and an organic material layer between the anode and cathode. The organic material layer often consists of multilayers comprising different materials so as to increase the efficiency and stability of an organic light emitting device, and for example, it may consist of a hole injection layer, a hole transport layer, a light emission layer, an electron transport layer, an electron injection layer, and the like. In such a structure of the organic light emitting device, if voltage is applied between two electrodes, holes are injected from the anode and electrons injected from the cathode into the organic material layer, and when the injected holes and electrons meet, excitons are formed, and when the excitons fall back to the ground state, light is emitted.

There is a continued demand for the development of novel materials for the organic materials used in the organic light emitting devices.

PRIOR ART LITERATURE

Patent Literature (Patent Literature 0001) Korean Laid-Open Patent Publication No. 10-2000-0051826

DETAILED DESCRIPTION OF THE INVENTION

Technical Problem

The present disclosure relates to a novel compound and an organic light emitting device using the same.

Technical Solution

There is provided a compound represented by the following Chemical Formula 1:

[Chemical Formula 1]

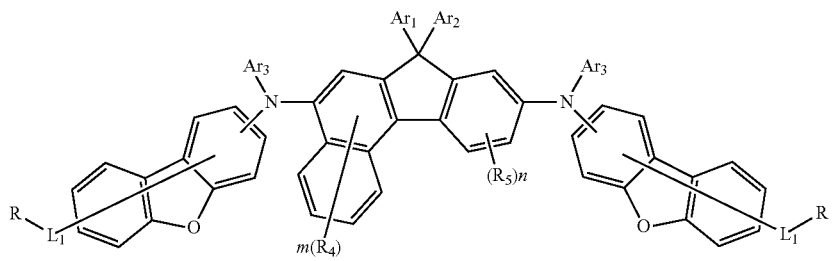

in the Chemical Formula 1,

R is $Si(R_1)(R_2)(R_3)$, $R_1$ to $R_3$ are each independently, hydrogen; deuterium; substituted or unsubstituted $C_{1-60}$ alkyl; or substituted or unsubstituted $C_{6-60}$ aryl; (tri($C_{1-60}$ alkyl)silyl)-($C_{1-10}$ alkylene)-; or (tri($C_{6-60}$ aryl)silyl)-($C_{1-10}$ alkylene)-, or $R_1$ and $R_2$ are linked to form a ring, provided that all of $R_1$ to $R_3$ are not substituted or unsubstituted $C_{1-60}$ alkyl, $L_1$ is a single bond; phenylene; or naphthalenediyl, m and n are each independently, an integer of 0 to 3, $R_4$ and $R_5$ are each independently, hydrogen; deuterium; halogen; cyano; substituted or unsubstituted $C_{1-60}$ alkyl; substituted or unsubstituted $C_{1-60}$ alkoxy; substituted or unsubstituted $C_{1-60}$ thioalkyl; substituted or unsubstituted $C_{3-60}$ cycloalkyl; substituted or unsubstituted $C_{6-60}$ aryl; or substituted or unsubstituted $C_{5-60}$ heteroaryl comprising one or more heteroatoms selected from the group consisting of N, O and S, $Ar_3$ is deuterium; $C_{1-10}$ alkyl; substituted or unsubstituted $C_{6-60}$ aryl; or substituted or unsubstituted $C_{5-60}$ heteroaryl comprising one or more heteroatoms selected from the group consisting of N, O and S, $Ar_1$ and $Ar_2$ are each independently, hydrogen; deuterium; substituted or unsubstituted $C_{1-60}$ alkyl; substituted or unsubstituted $C_{3-60}$ cycloalkyl; substituted or unsubstituted $C_{6-60}$ aryl; or substituted or unsubstituted $C_{5-60}$ heteroaryl comprising one or more heteroatoms selected from the group consisting of N, O and S, or linked with each other to form $C_{3-60}$ cycloalkyl or a substituent represented by the following Chemical Formula 2,

[Chemical Formula 2]

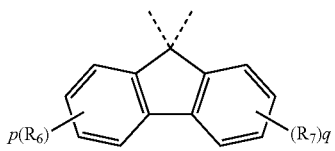

p and q are each independently, an integer of 0 to 4, $R_6$ and $R_7$ are each independently, hydrogen; deuterium; halogen; cyano; substituted or unsubstituted $C_{1-60}$ alkyl; substituted or unsubstituted $C_{1-60}$ alkoxy; substituted or unsubstituted $C_{1-60}$ thioalkyl; substituted or unsubstituted $C_{3-60}$ cycloalkyl; substituted or unsubstituted $C_{6-60}$ aryl; or substituted or unsubstituted $C_{5-60}$ heteroaryl comprising one or more heteroatoms selected from the group consisting of N, O and S.

There is also provided an organic light emitting device comprising a first electrode; a second electrode opposite the first electrode; and one or more organic material layers between the first electrode and the second electrode, wherein one or more of the organic material layers comprise the compound represented by the Chemical Formula 1.

Advantageous Effects

The compounds represented by the Chemical Formula 1 may be used as materials of organic material layers of organic light emitting devices, and improve efficiency, achieve low driving voltage and/or life characteristics in organic light emitting devices. And, the compounds represented by the Chemical Formula 1 may be used as materials for hole injection, hole transport, hole injection and transport, light emission, electron transport or electron injection.

BRIEF DESCRIPTION OF DRAWINGS

FIG. 1 shows the example of an organic light emitting device consisting of a substrate (1), an anode (2), a light emission layer (3), and a cathode (4).

FIG. 2 shows the example of an organic light emitting device consisting of a substrate (1), an anode (2), a hole injection layer (5), a hole transport layer (6), a light emission layer (7), an electron transport layer (8) and a cathode (4).

DETAILED DESCRIPTION OF THE EMBODIMENTS

Hereinafter, the present disclosure will be explained in more detail.

There is provided a compound represented by the above Chemical Formula 1.

As used herein, $-\xi-$, or | means a bond connected to other substituents.

As used herein, the term "substituted or unsubstituted" means unsubstituted or substituted with one or more substituents selected from the group consisting of deuterium; halogen; nitrile; nitro; hydroxy; carbonyl; ester; imide; amino; phosphine oxide; alkoxy; aryloxy; alkylthioxy; arylthioxy; alkylsulfoxy; arylsulfoxy; silyl; boron; alkyl; cycloalkyl; alkenyl; aryl; aralkyl; aralkenyl; alkylaryl; alkylamine; aralkylamine; heteroarylamine; arylamine; arylphosphine; or heterocyclic group comprising one or more of N, O and S atoms, or unsubstituted or substituted with a substituent in which two or more of the above described substituents are connected. For example, "a substituent in which two or more substituents are connected" may be a biphenyl group. Namely, a biphenyl group may be an aryl group, or it may be interpreted as a substituent in which two phenyl groups are connected.

Throughout the specification, the carbon number of a carbonyl group is not specifically limited, but is preferably 1 to 40. Specifically, it may be a compound of the following structure, but is not limited thereto.

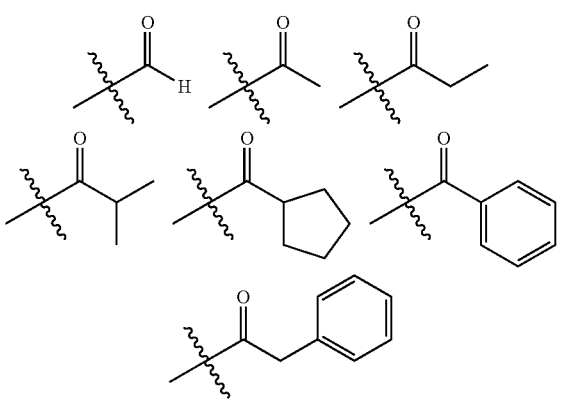

Throughout the specification, oxygen of an ester group may be substituted with a liner, branched or cyclic C1-25 alkyl group or C6-25 aryl group. Specifically, it may be a compound of the following structure, but is not limited thereto.

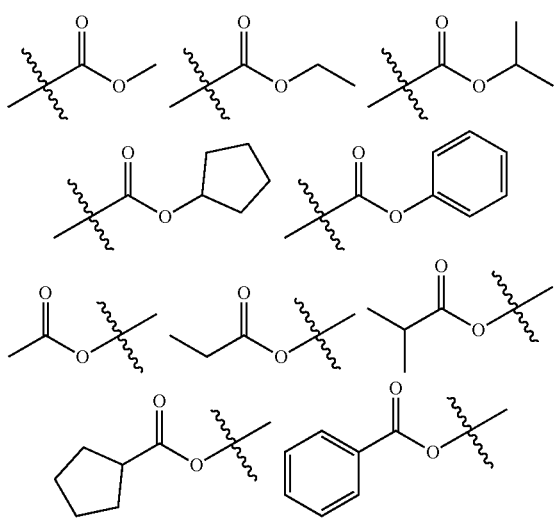

Throughout the specification, the carbon number of an imide group is not specifically limited, but is preferably 1 to 25. Specifically, it may be a compound of the following structure, but is not limited thereto.

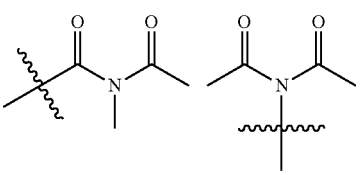

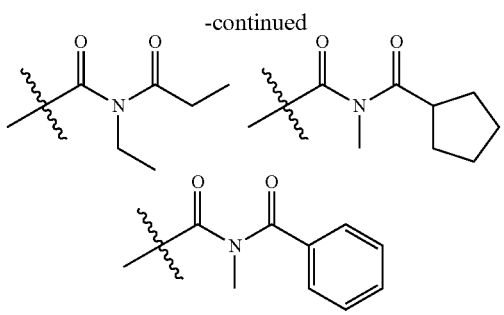

Throughout the specification, a silyl group may be specifically a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

Throughout the specification, a boron group may be specifically a trimethylboron group, a triethylboron group, a t-butyldimethylboron group, a triphenylboron group, a phenylboron group, and the like, but is not limited thereto.

Throughout the specification, examples of a halogen group may include fluorine, chlorine, bromine or iodine.

Throughout the specification, an alkyl group may be linear or branched, and the carbon number is not specifically limited, but preferably 1 to 40. According to one embodiment, the carbon number of the alkyl group is 1 to 20. According to one embodiment, the carbon number of the alkyl group is 1 to 10. According to one embodiment, the carbon number of the alkyl group is 1 to 6. Specific examples of the alkyl group may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 4-methylhexyl, 5-methylhexyl, and the like, but are not limited thereto.

Throughout the specification, an alkenyl group may be linear or branched, and the carbon number is not specifically limited, but is preferably 2 to 40. According to one embodiment, the carbon number of the alkenyl group is 2 to 20. According to another embodiment, the carbon number of the alkenyl group is 2 to 10. According to yet another embodiment, the carbon number of the alkenyl group is 2 to 6. Specific examples may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, stilbenyl, styrenyl, and the like, but are not limited thereto.

Throughout the specification, a cycloalkyl group is not specifically limited, but the carbon number is preferably 3 to 60, and according to one embodiment, the carbon number of the cycloalkyl group is 3 to 30. According to another embodiment, the carbon number of the cycloalkyl group is 3 to 20. According to yet another embodiment, the carbon number of the cycloalkyl group is 3 to 6. Specific examples may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

Throughout the specification, an aryl group is not specifically limited, but preferably has a carbon number of 6 to 60, and it may be a monocyclic aryl group or a polycyclic aryl group. According to one embodiment, the carbon number of the aryl group is 6 to 30. According to one embodiment, the carbon number of the aryl group is 6 to 20. As the monocyclic aryl group, a phenyl group, a biphenyl group, a terphenyl group, and the like may be mentioned, but not limited thereto. As the polycyclic aryl group, a naphthyl group, an anthracenyl group, a phenanthryl group, a pyrenyl group, a perylenyl group, a chrysenyl group, a fluorenyl group, and the like may be mentioned, but not limited thereto.

Throughout the specification, a fluorenyl group may be substituted, and two substituents may be linked to form a spiro structure. In case the fluorenyl group is substituted, it may be

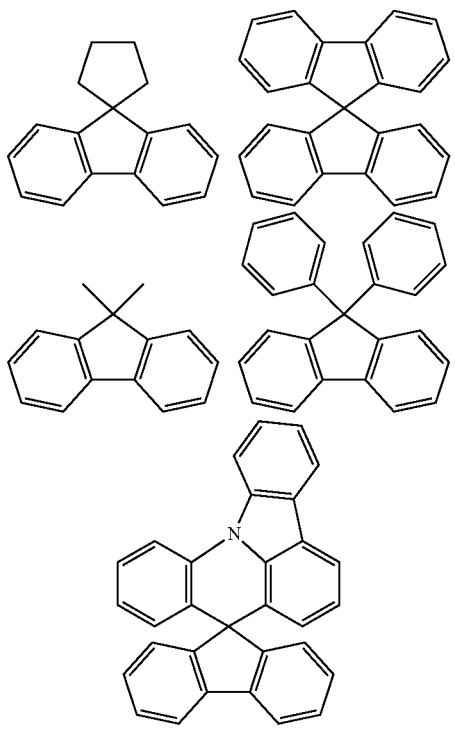

and the like, but is not limited thereto.

Throughout the specification, a heterocyclic group is a heterocyclic group comprising one or more selected from O, N, P, Si and S as heteroatom, and the carbon number is not specifically limited, but preferably 2 to 60. As the examples of the heterocyclic groups, a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazino pyrazinyl group, an isoquinoline group, an indole group, a carbozole group, a benzoxazole group, a benzoimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group and a dibenzofuranyl group, and the like may be mentioned, but are not limited thereto.

Throughout the specification, the aryl groups of an aryalkyl group, an aralkenyl group, an alkylaryl group, and an arylamine group are as explained in the aryl group. Throughout the specification, the alkyl group of an aralkyl group, an alkylaryl group, and an alkylamine group are as explained in the alkyl group. Throughout the specification, for heteroaryl of heteroarylamine, explanations about the heterocyclic group may be applied. Throughout the specification, the alkenyl group of an aralkenyl group is as explained in the alkenyl group. Throughout the specification, for arylene, except being divalent, explanations about the aryl group may be applied. Throughout the specification, for heteroarylene, except being divalent, explanations about the heterocyclic group may be applied. Throughout the specification, for hydrocarbon ring, except that it is not monovalent, and is formed by bonding of two substituents, explanations about the aryl group or cycloalkyl group may be applied. Throughout the specification, for heterocycle, except that it is not a monovalent group, and is formed by bonding of two substituents, explanations about the heterocyclic group may be applied.

Preferably, the Chemical Formula 1 may be any one of the following Chemical Formulas 1-1 to 1-5.

[Chemical Formula 1-1]

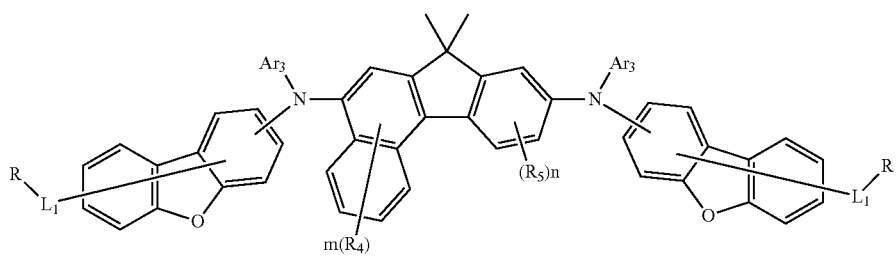

[Chemical Formula 1-2]

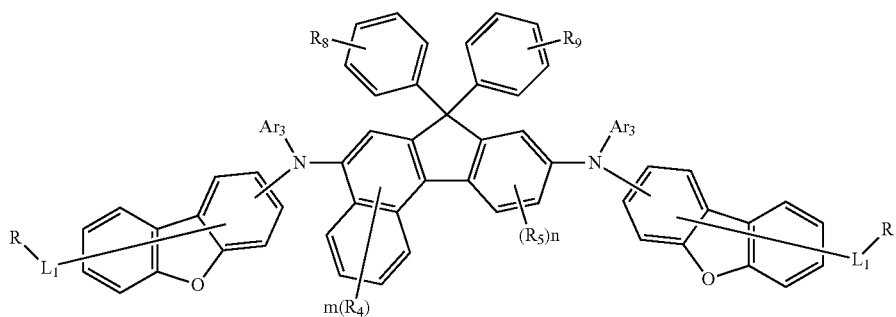

[Chemical Formula 1-3]

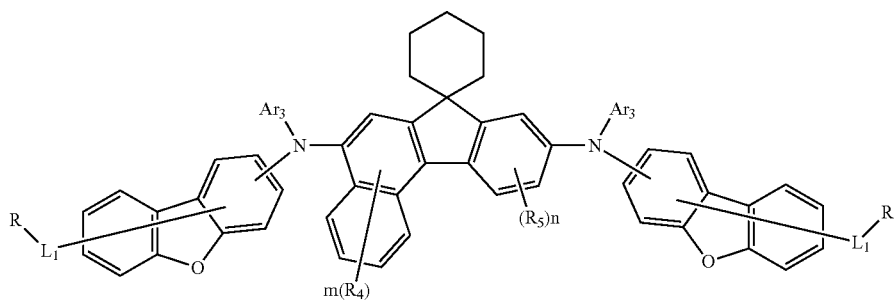

[Chemical Formula 1-4]

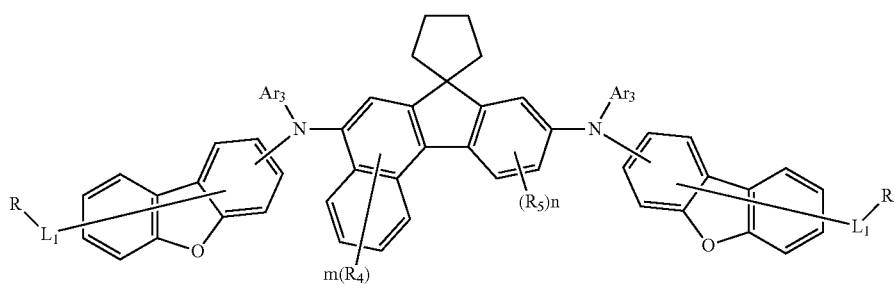

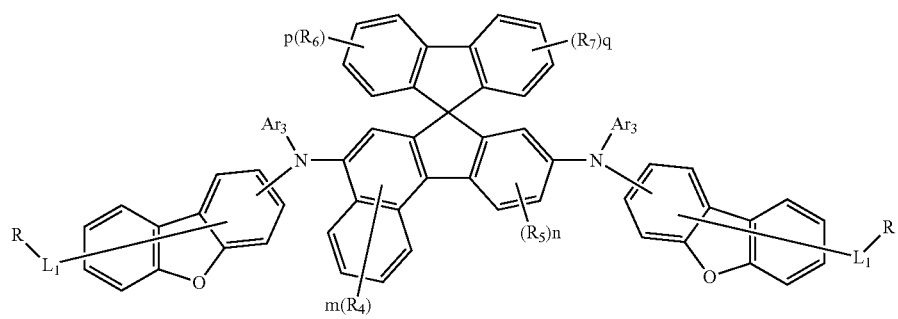

in the Chemical Formulas 1-1 to 1-5, $R_8$ and $R_9$ are each independently, hydrogen; or substituted or unsubstituted $C_{1-60}$ alkyl, and m, n, p, q, R, $R_4$ to $R_7$, $L_1$ and $Ar_3$ are as defined above.

Preferably, $R_1$ to $R_3$ are each independently, methyl; i-propyl; t-butyl; phenyl; or trimethylsilyl-ethylene.

Preferably, at least one of $R_1$ to $R_3$ may be phenyl.

Preferably, $L_1$ may be a single bond; or phenylene.

And, preferably, both m and n may be 0.

Preferably, p and q may be each independently, 0 or 1.

Preferably, $R_6$ and $R_7$ may be each independently, hydrogen; or $C_{1-10}$ alkyl, more preferably, hydrogen, methyl or t-butyl.

Preferably, $R_8$ and $R_9$ may be each independently, hydrogen; or $C_{1-10}$ alkyl, more preferably, hydrogen, methyl or t-butyl.

Preferably, Ara may be deuterium; $C_{1-10}$ alkyl; or phenyl unsubstituted or substituted with tri($C_{1-5}$ alkyl)silyl; or naphthyl.

For example, the compound represented by the Chemical Formula 1 may be selected from the group consisting of the following compounds:

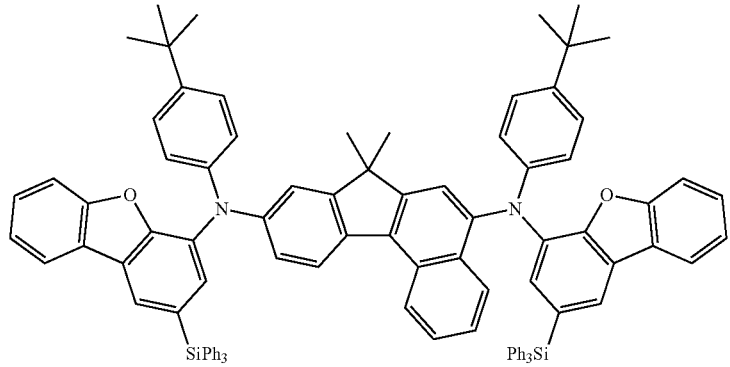

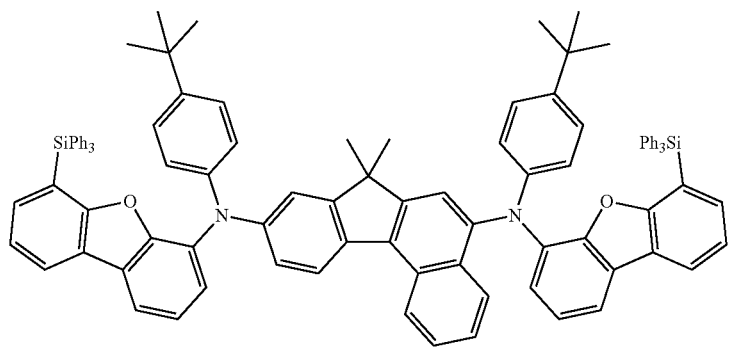

-continued
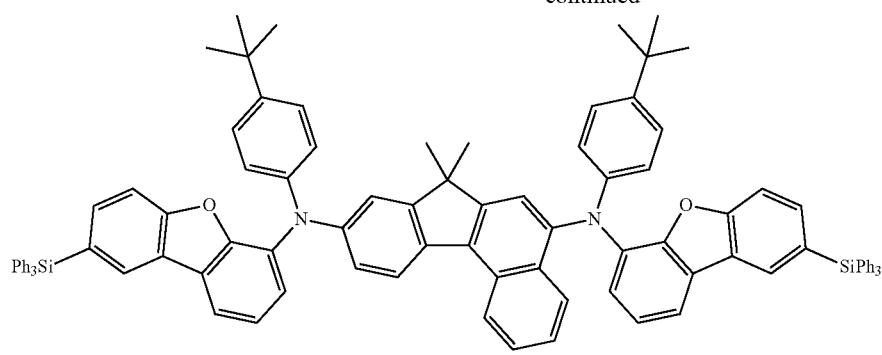
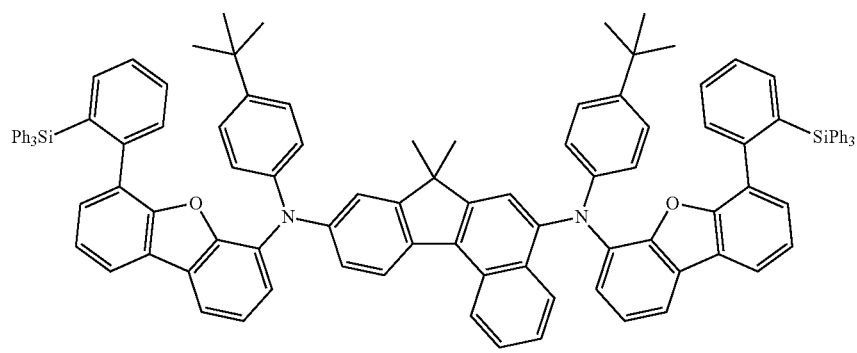
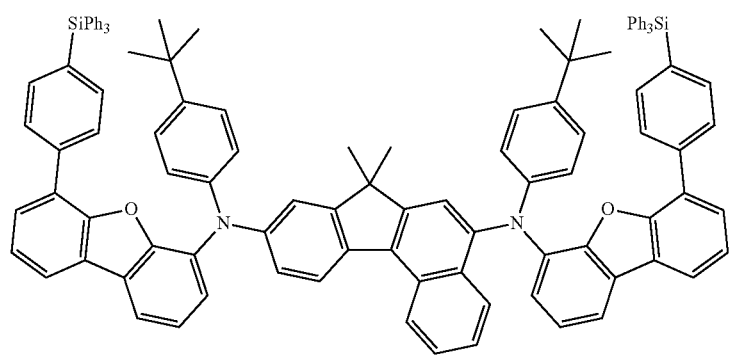
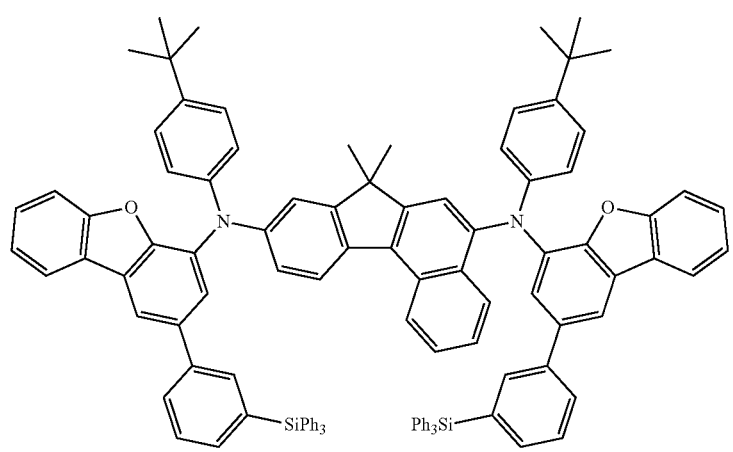

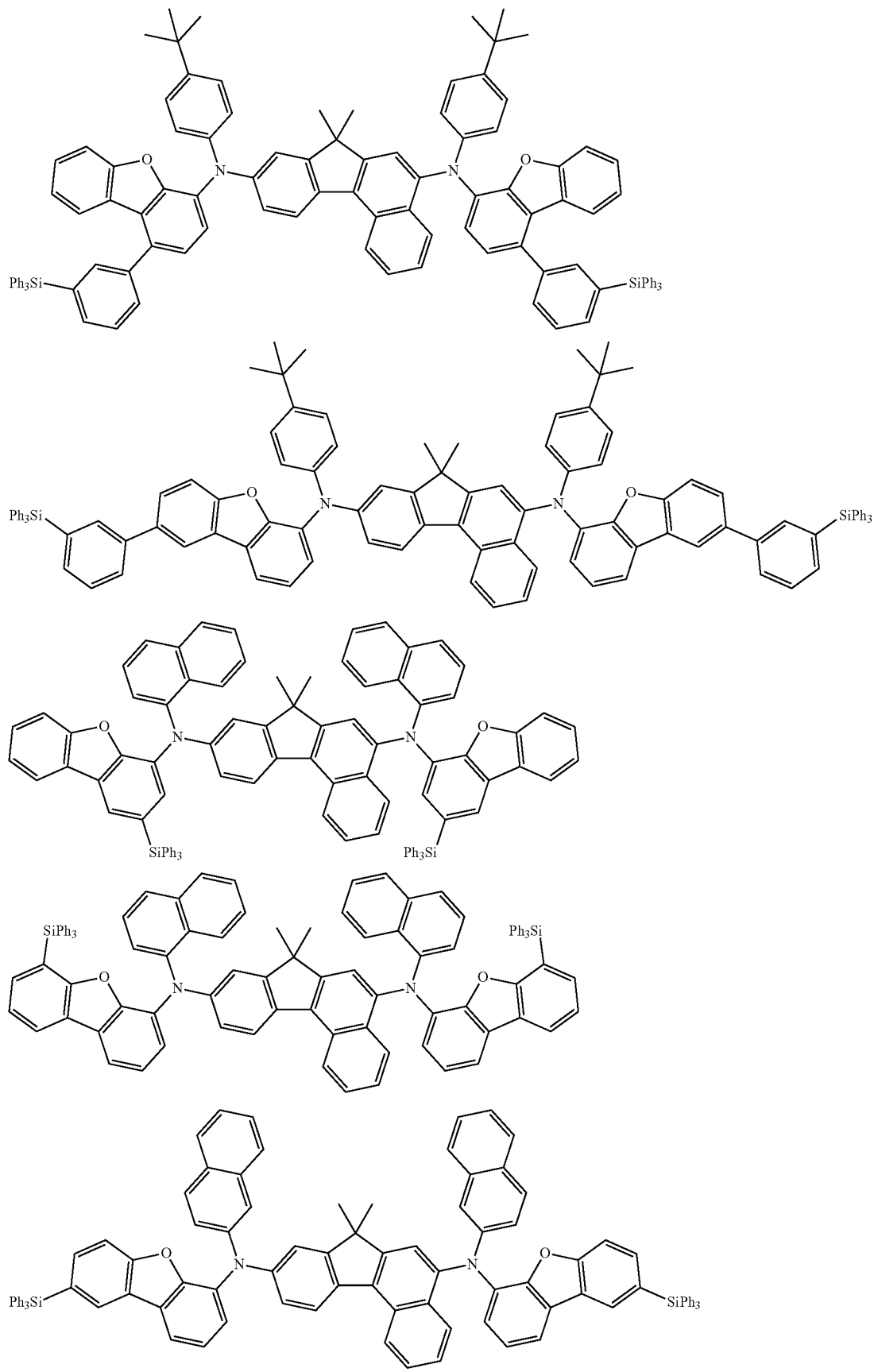

-continued
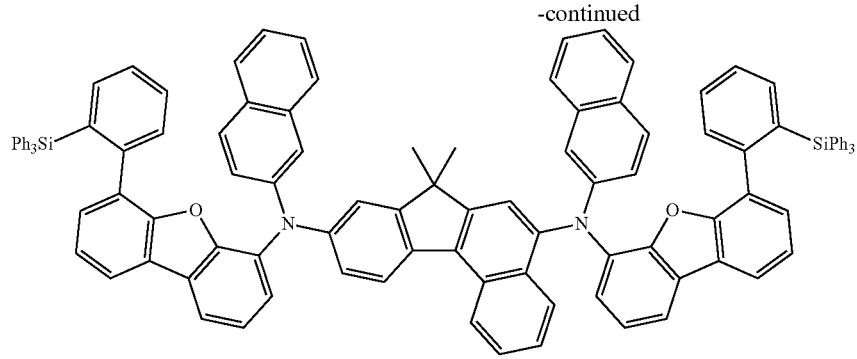
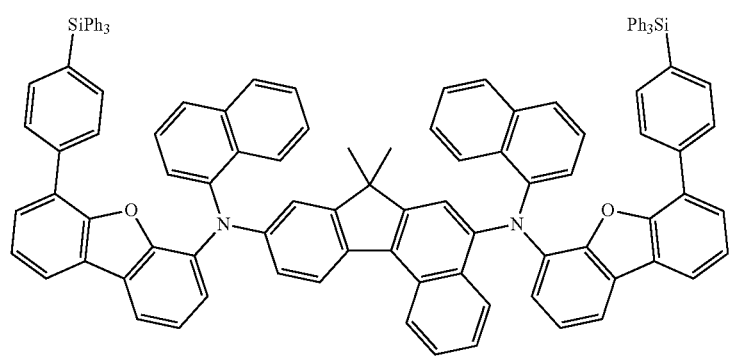
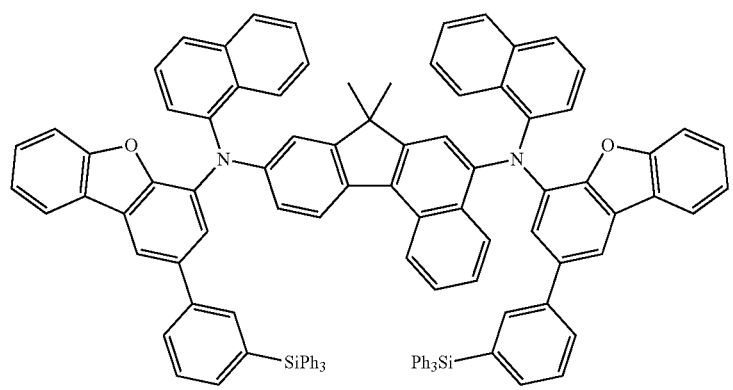
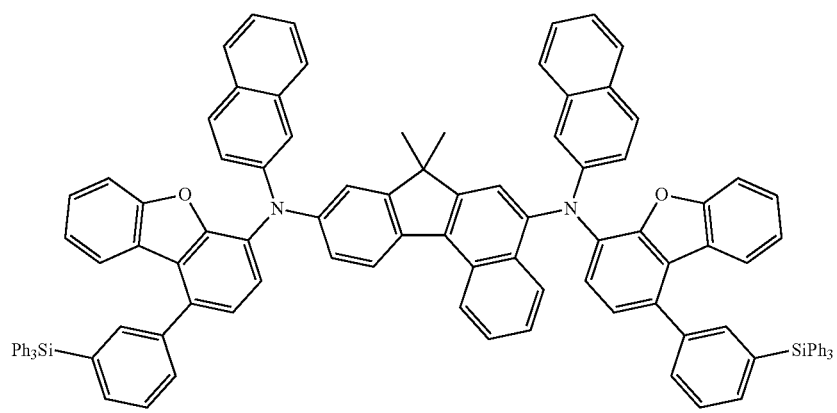

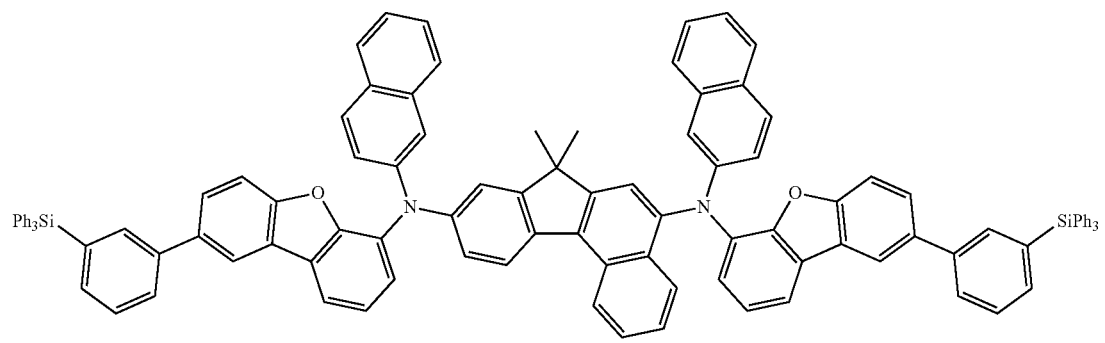
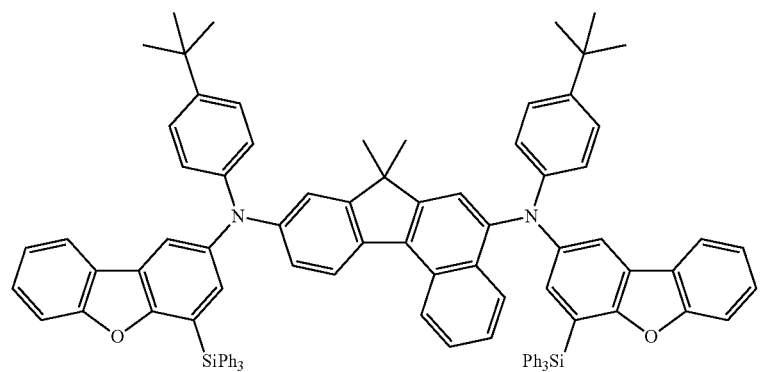
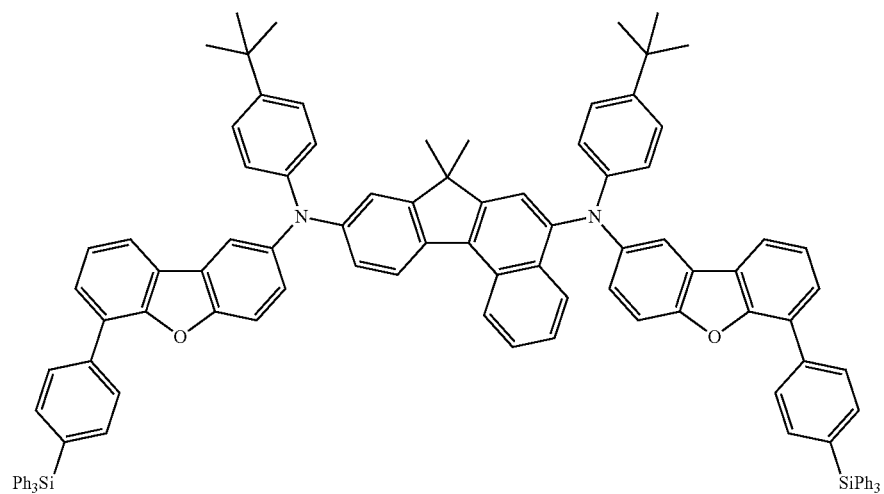
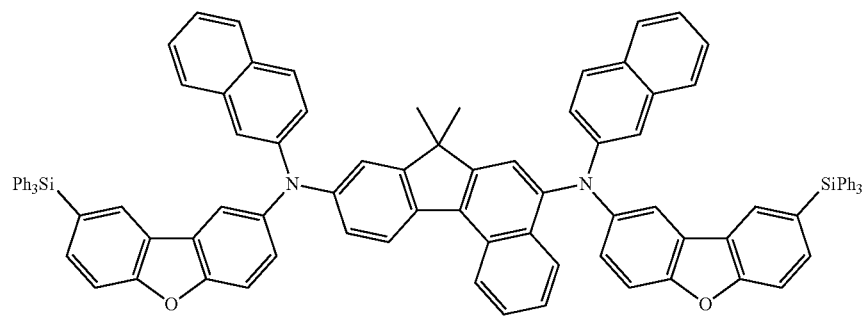

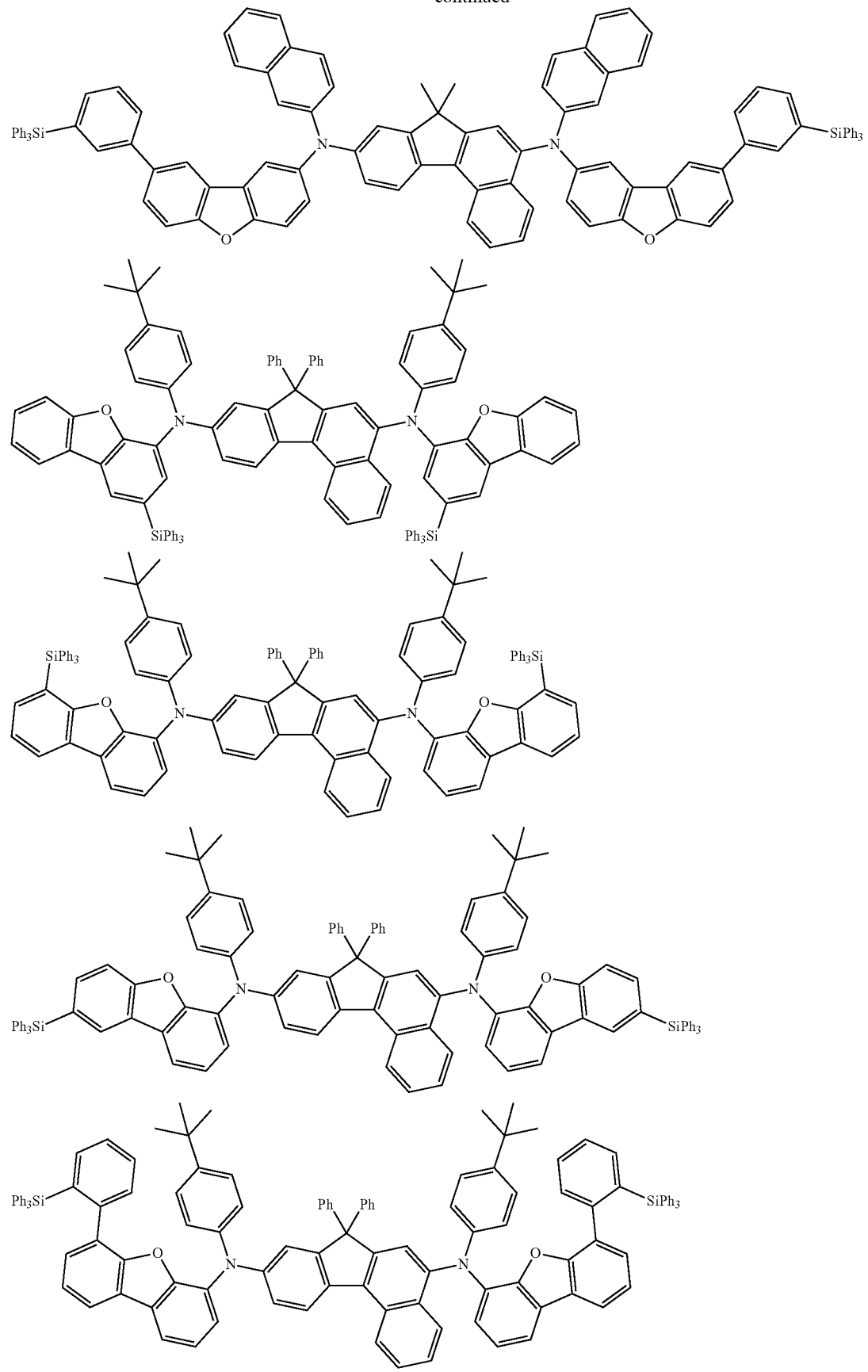

-continued
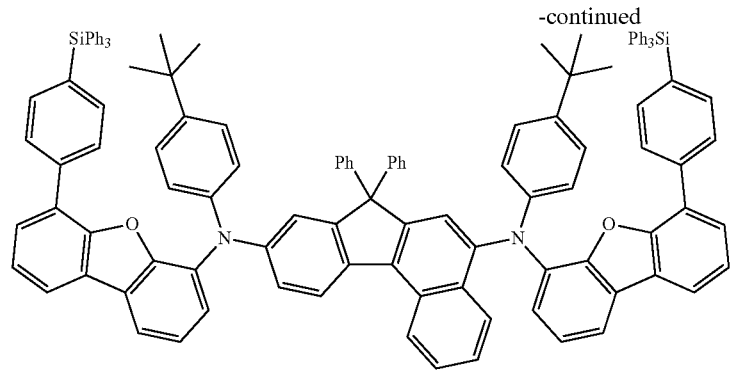
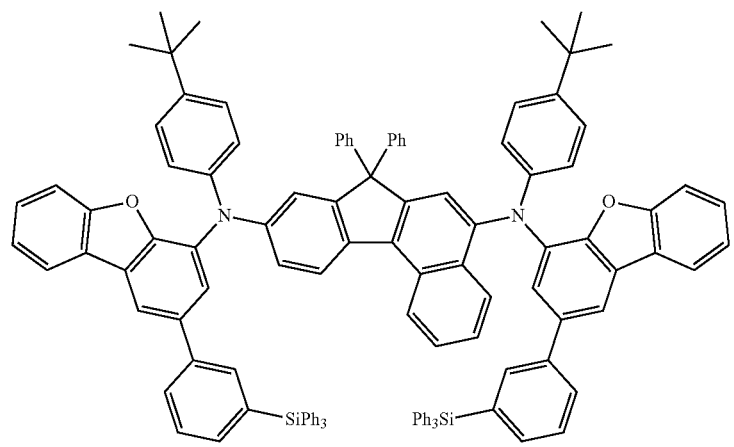
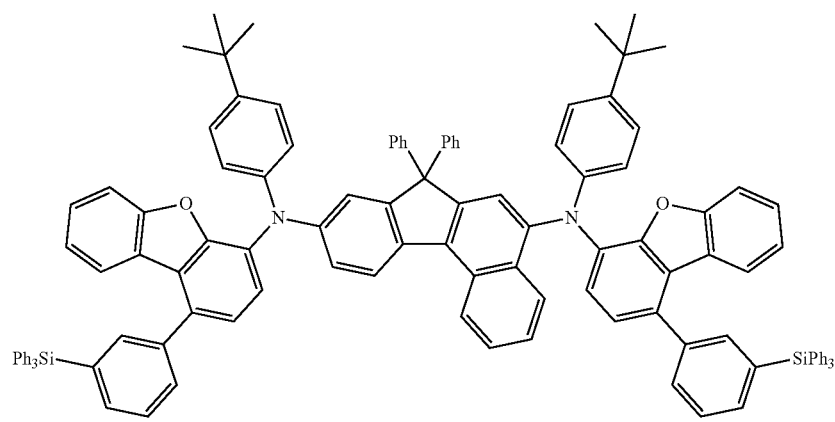
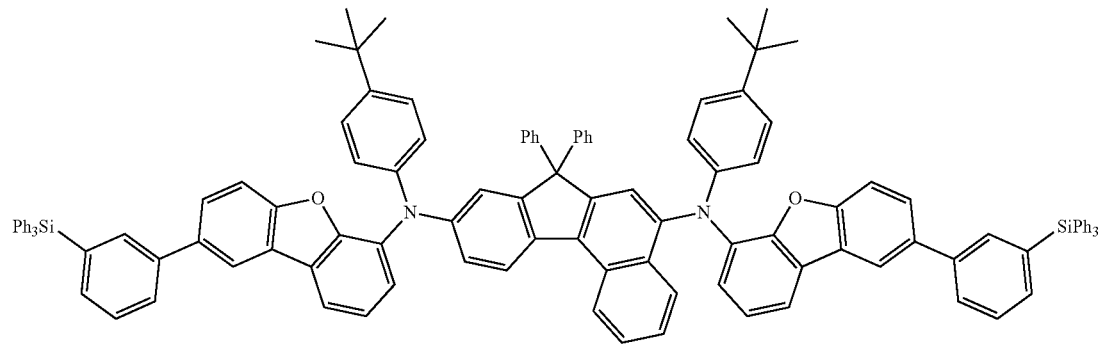

-continued
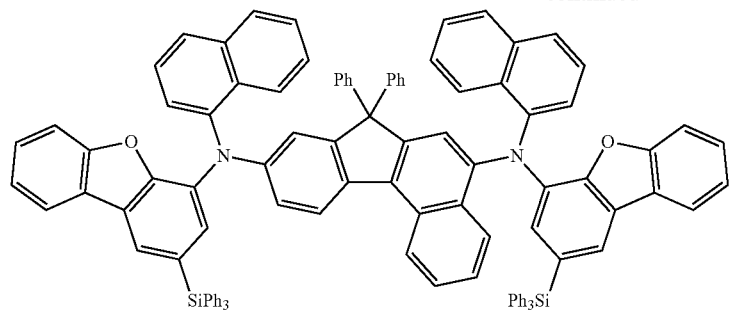
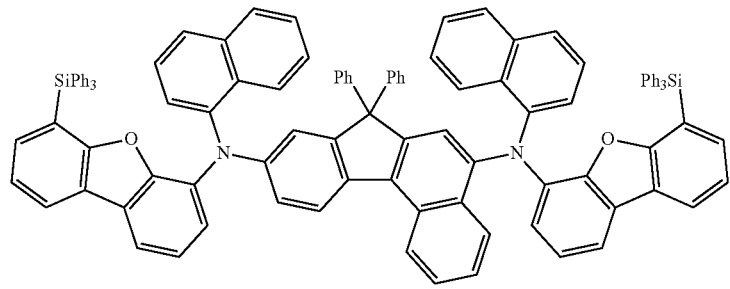
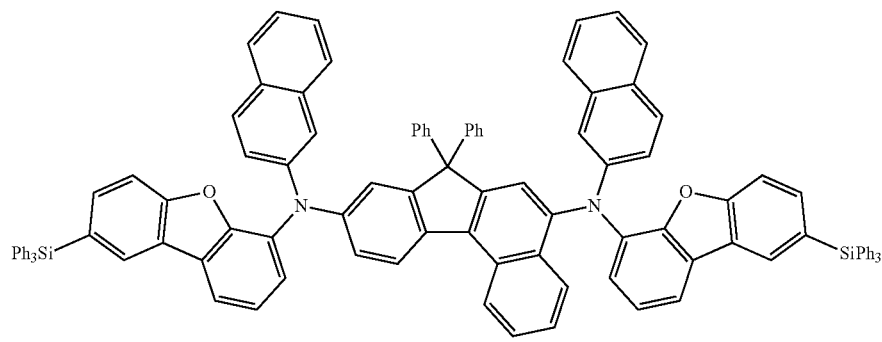
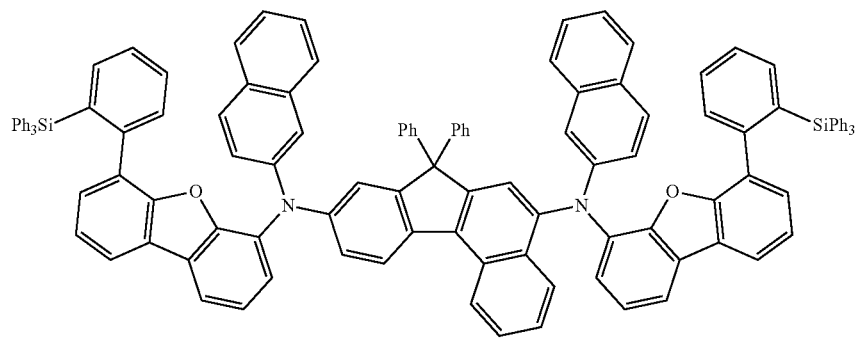
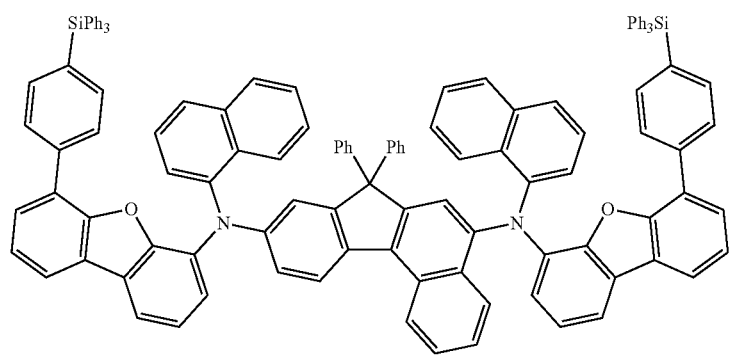

-continued
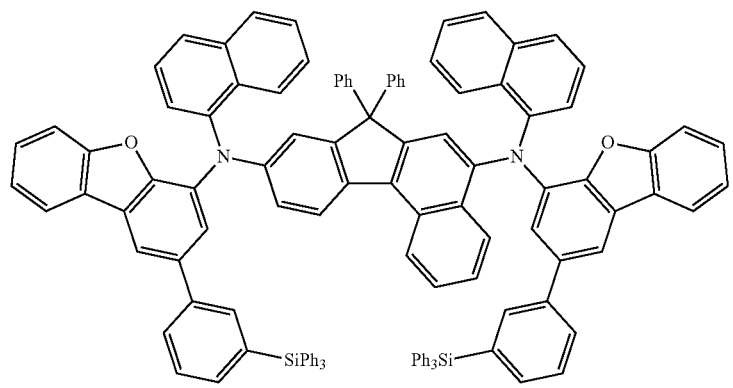
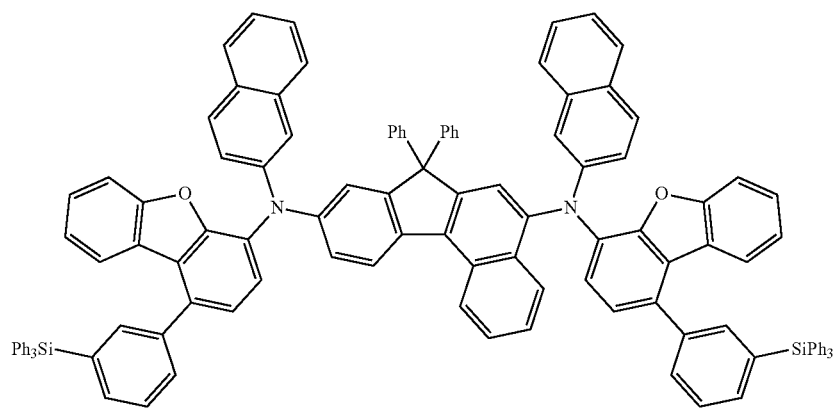
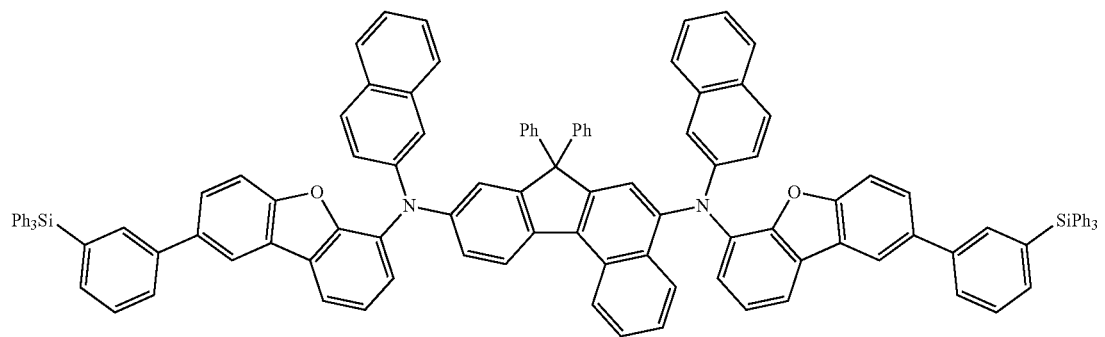
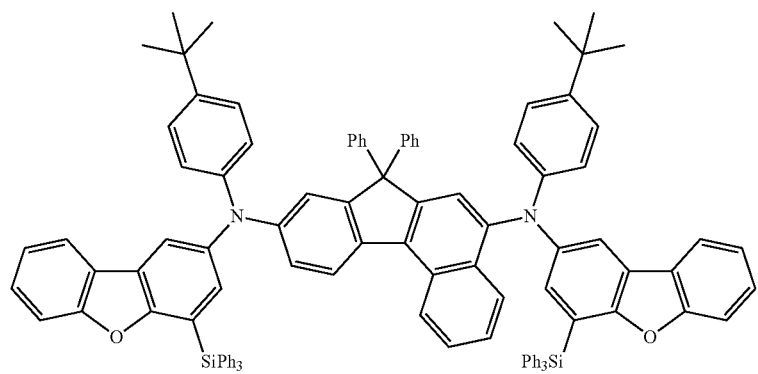

-continued
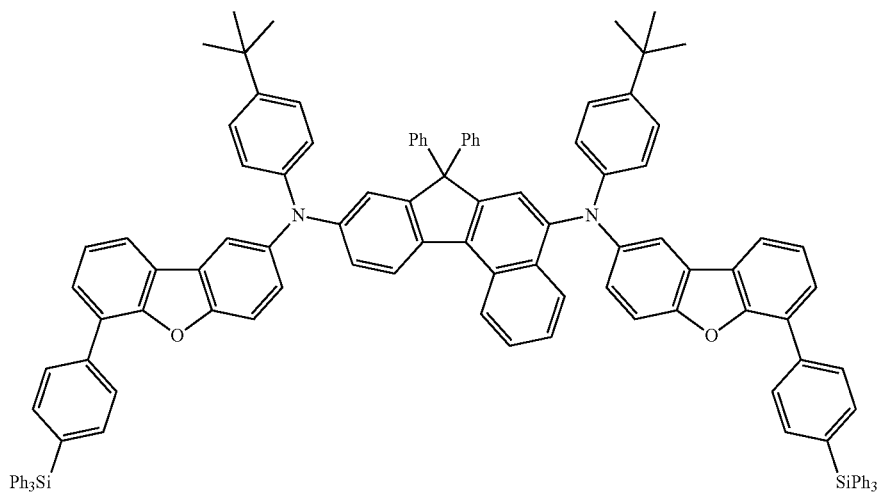
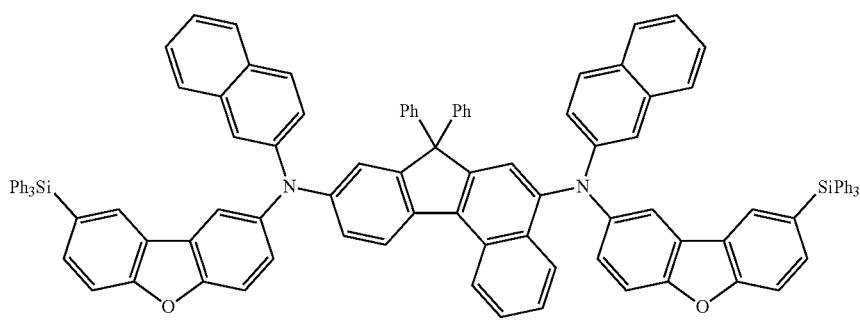
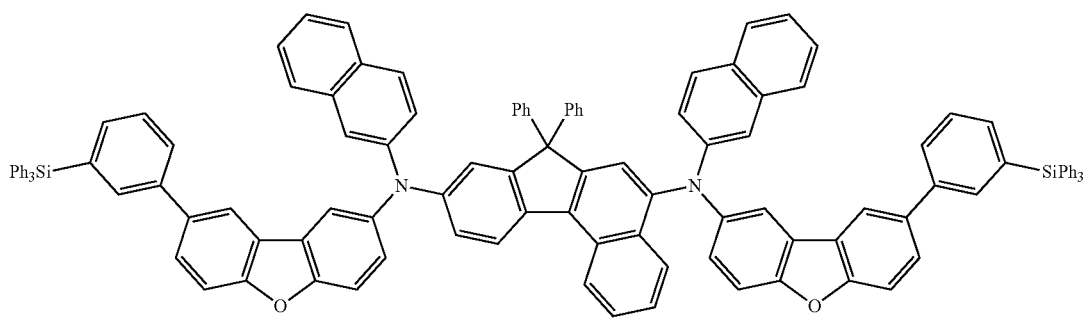
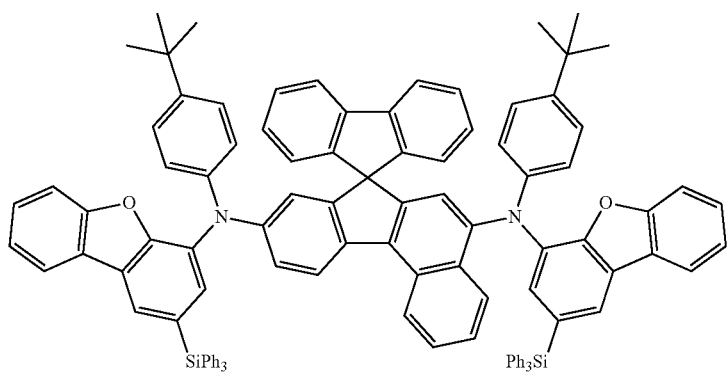

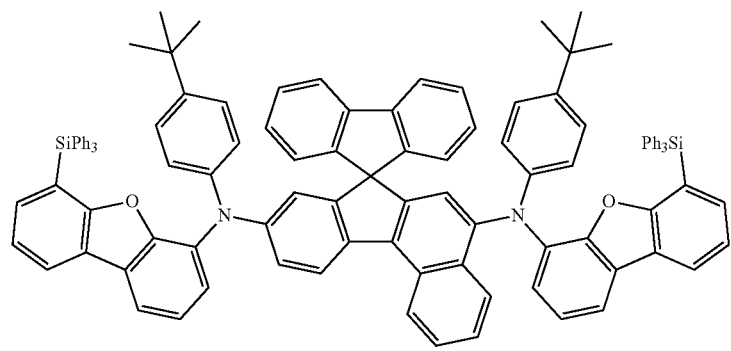
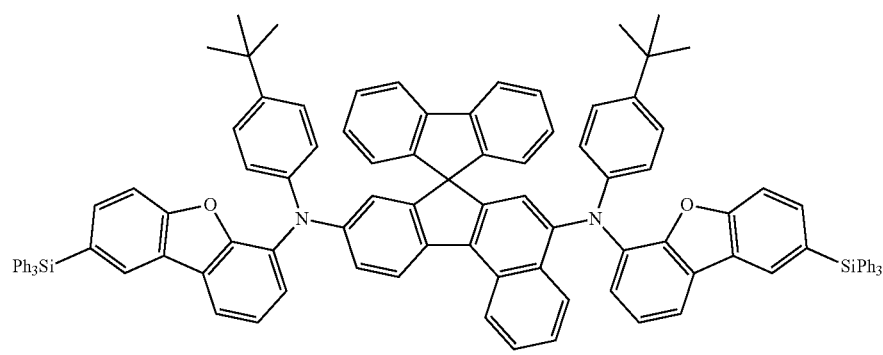
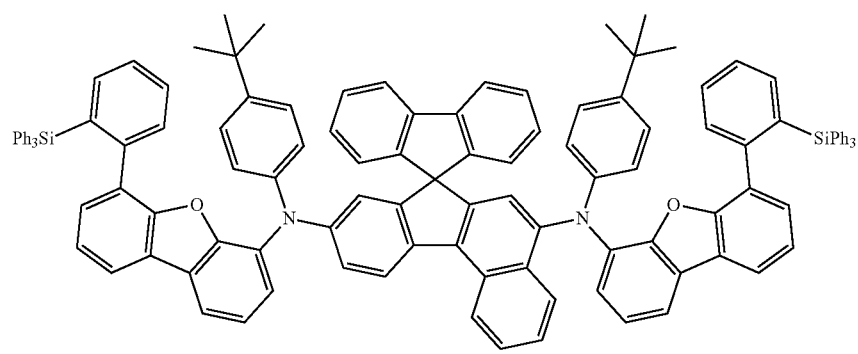
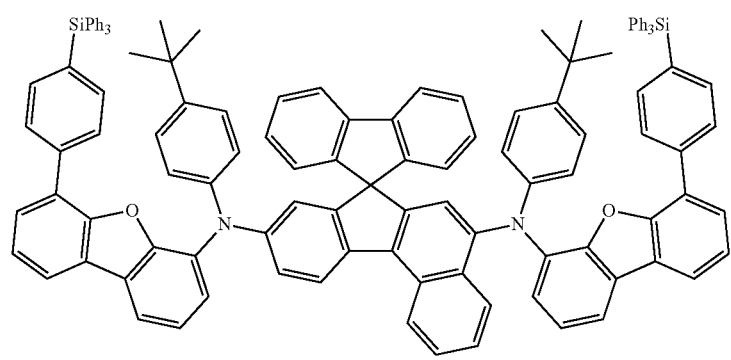

-continued
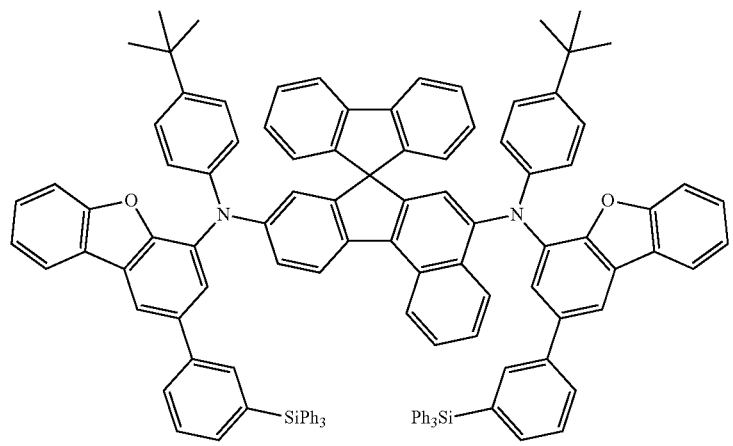
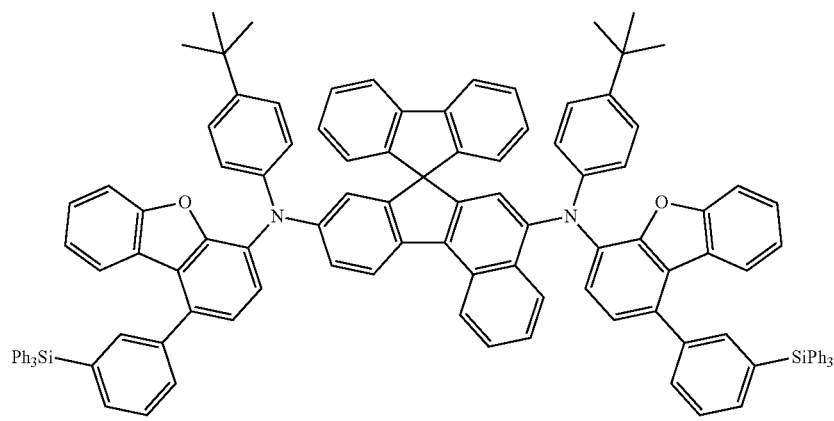
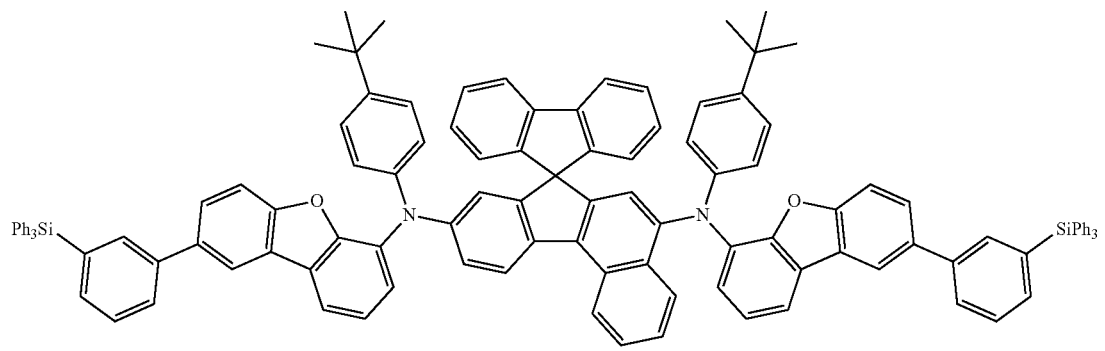
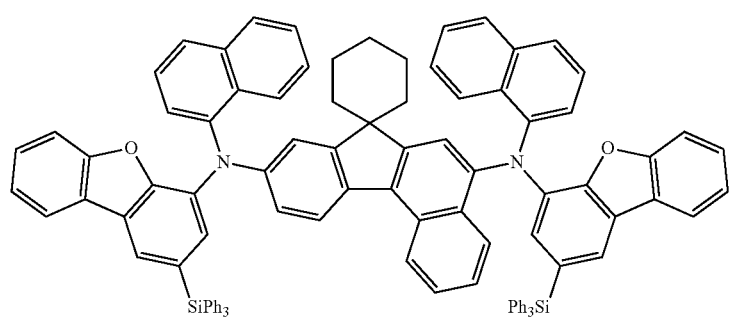

-continued
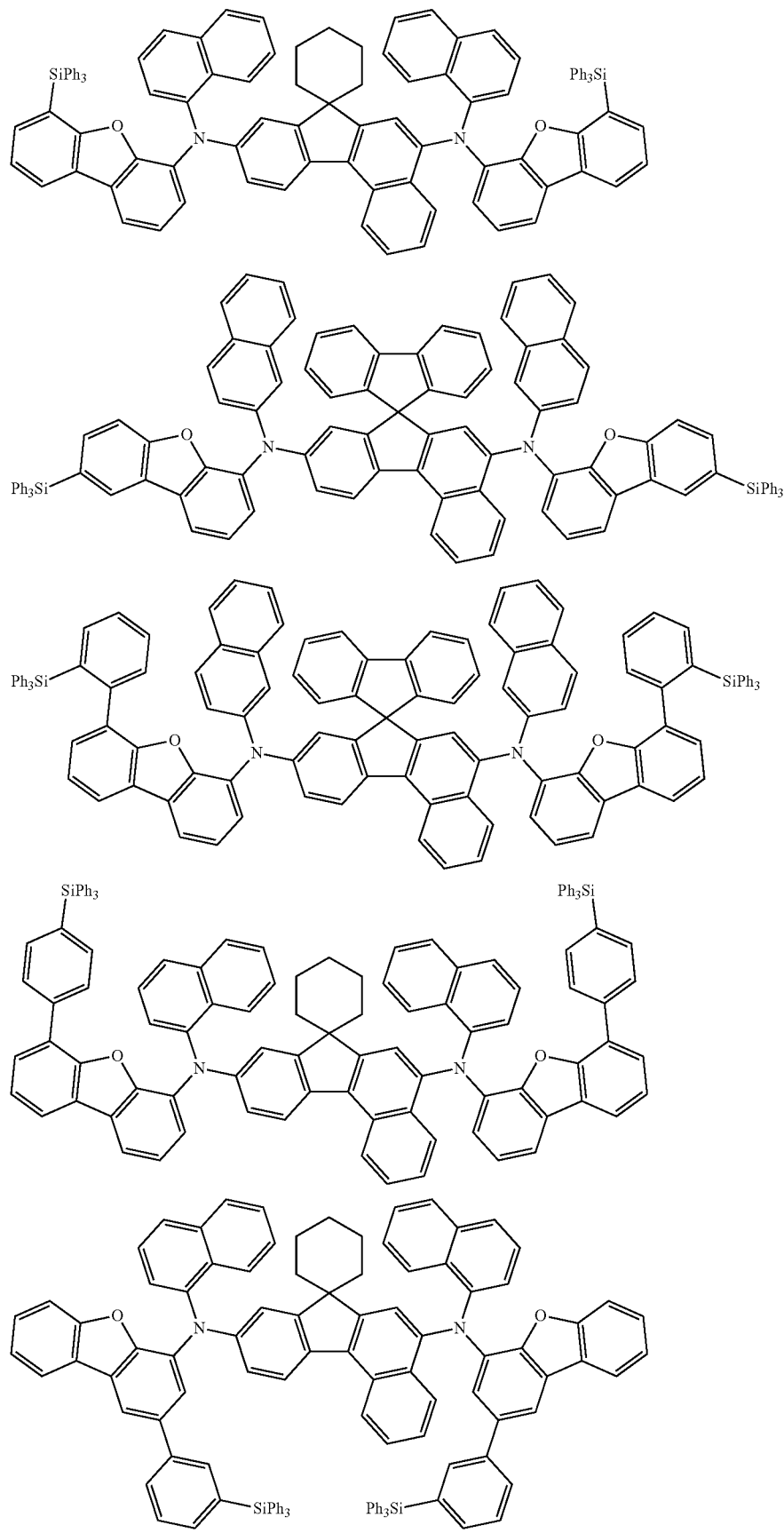

-continued
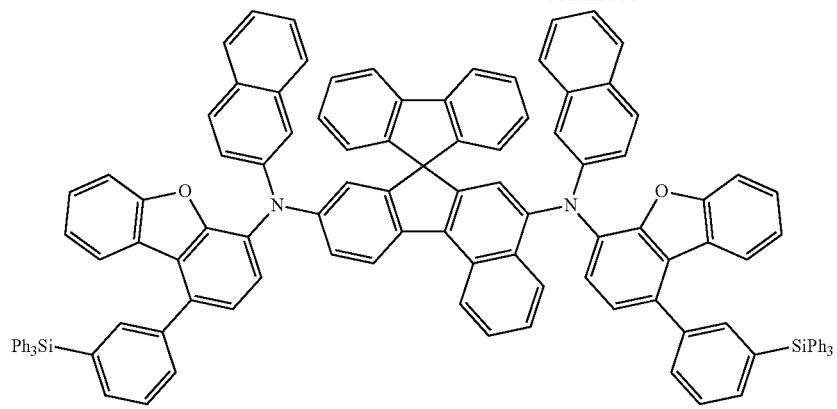
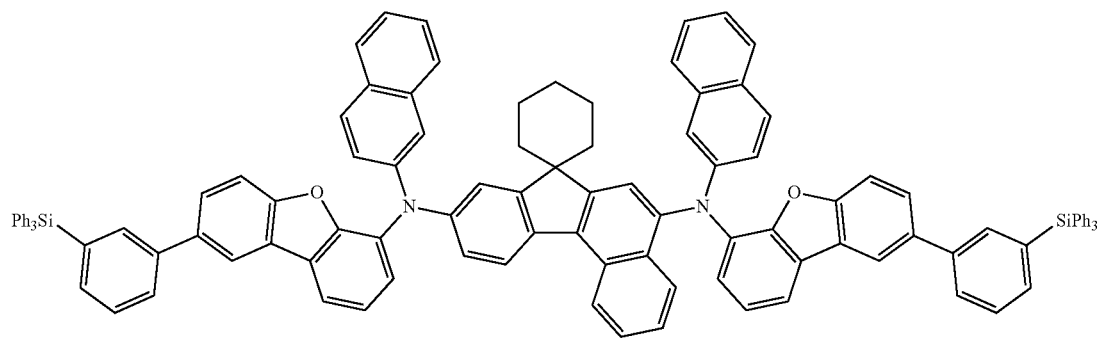
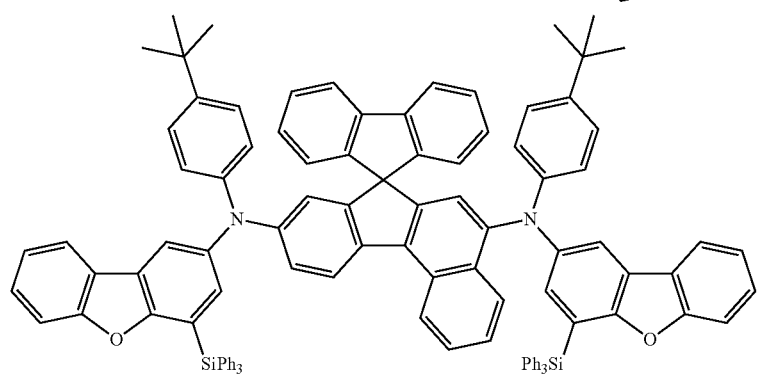
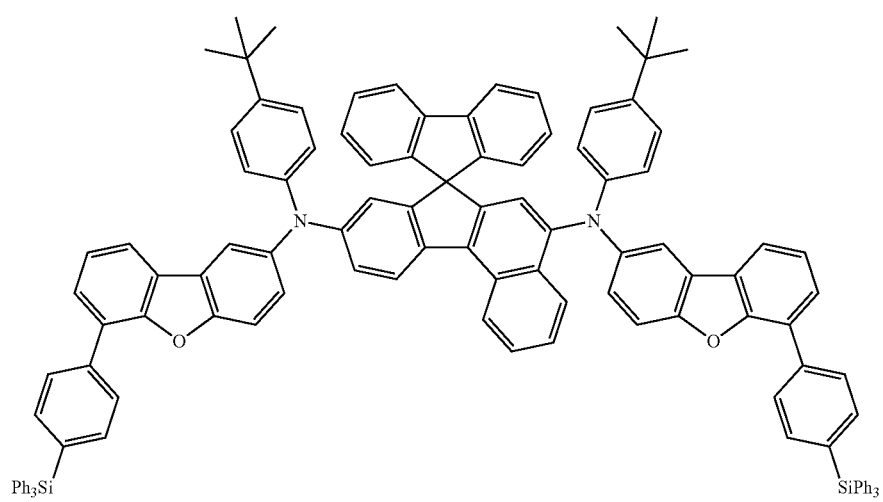

-continued
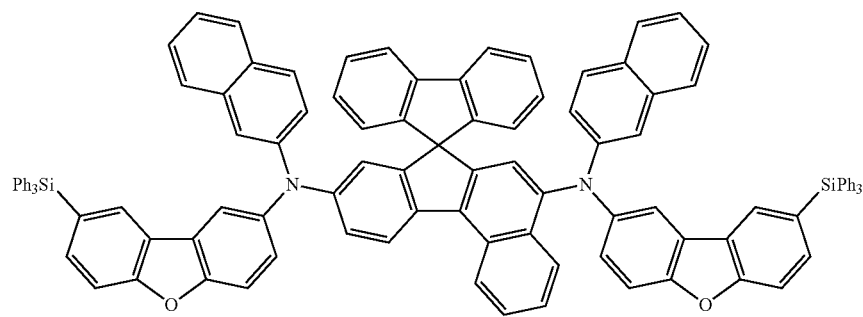
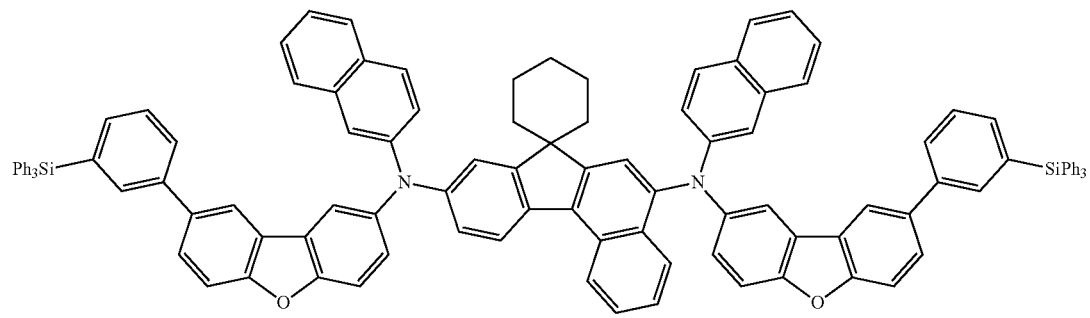
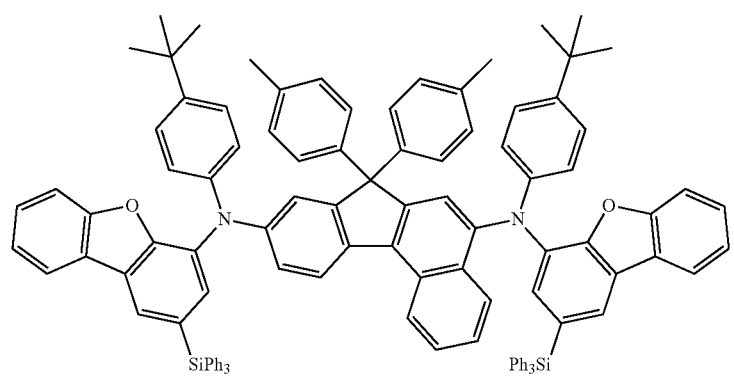
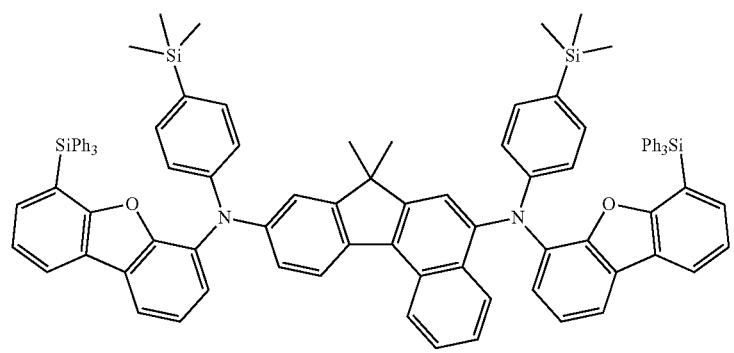
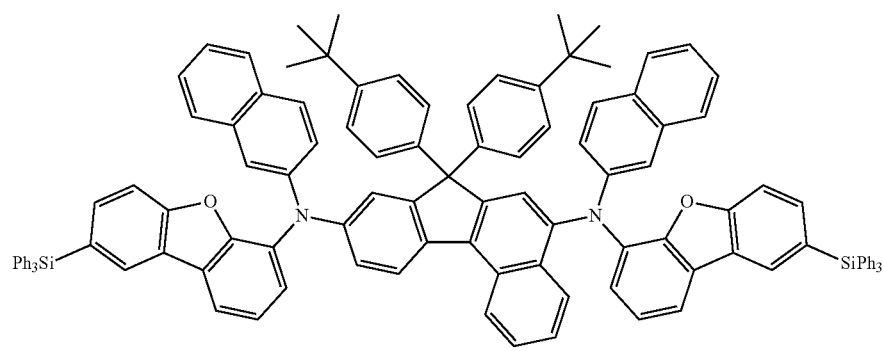

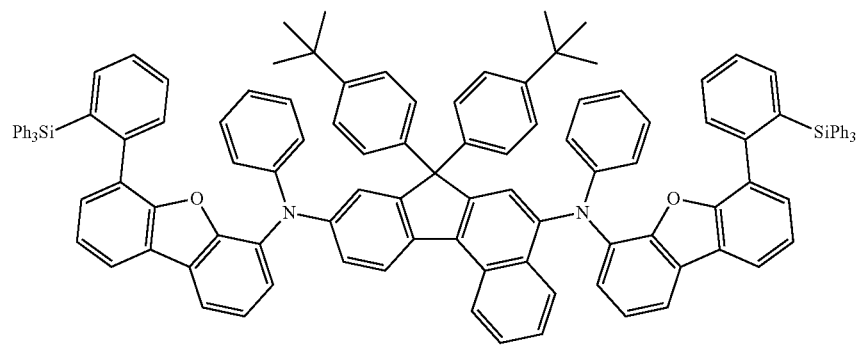
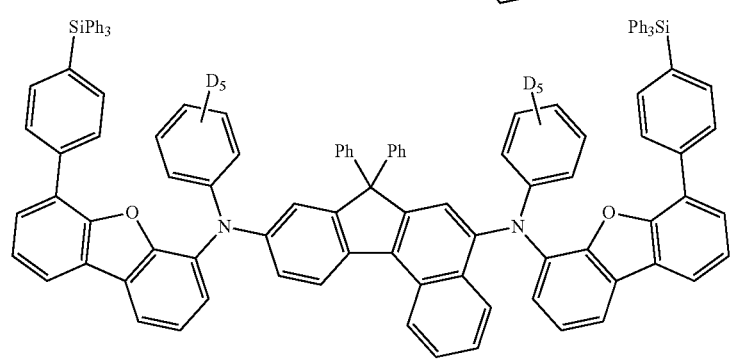
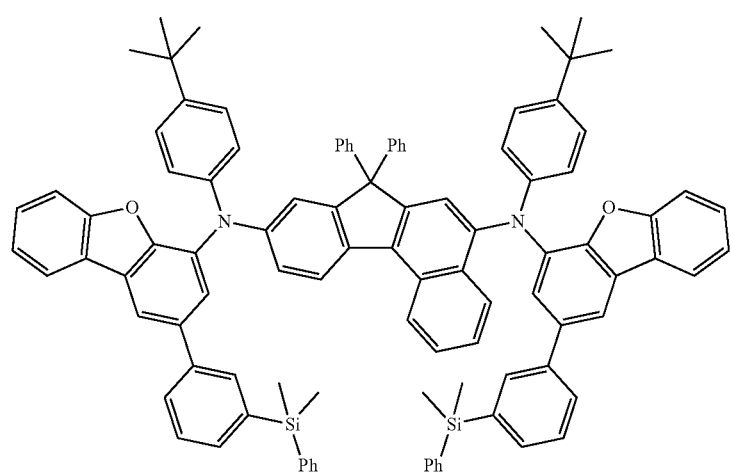
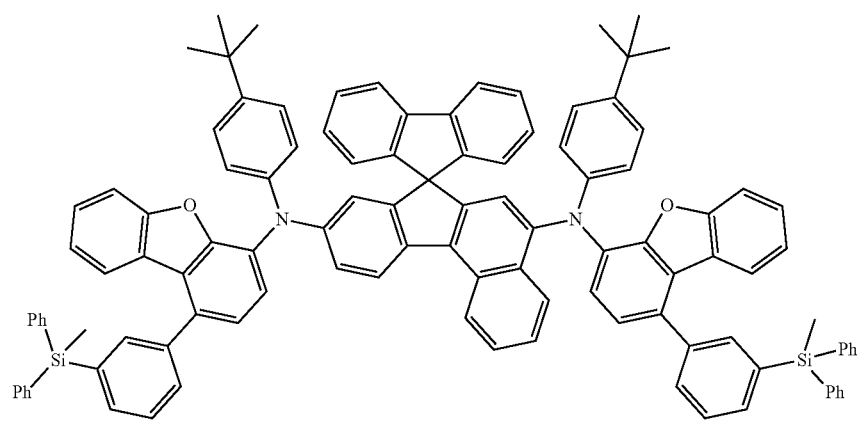

-continued
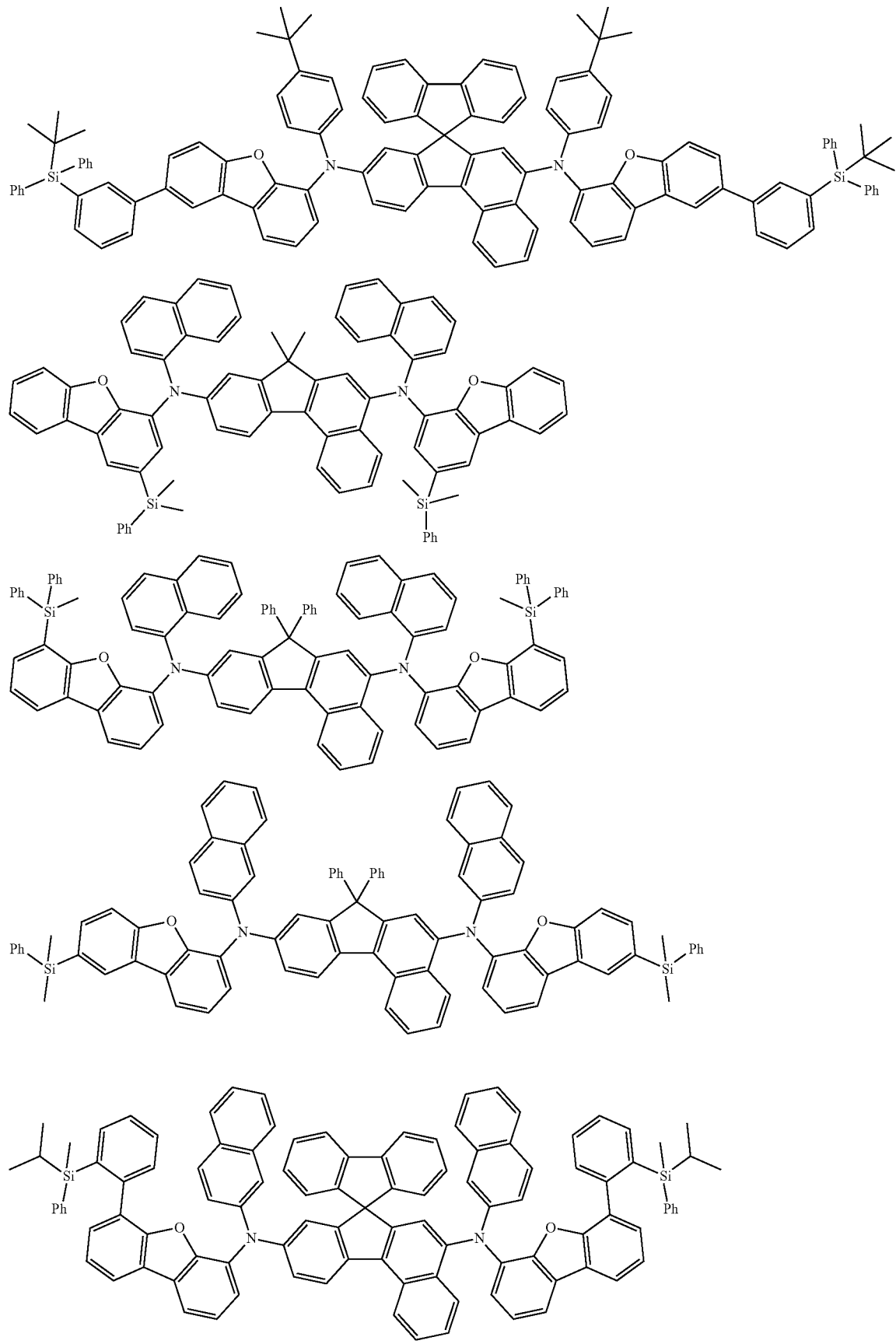

-continued
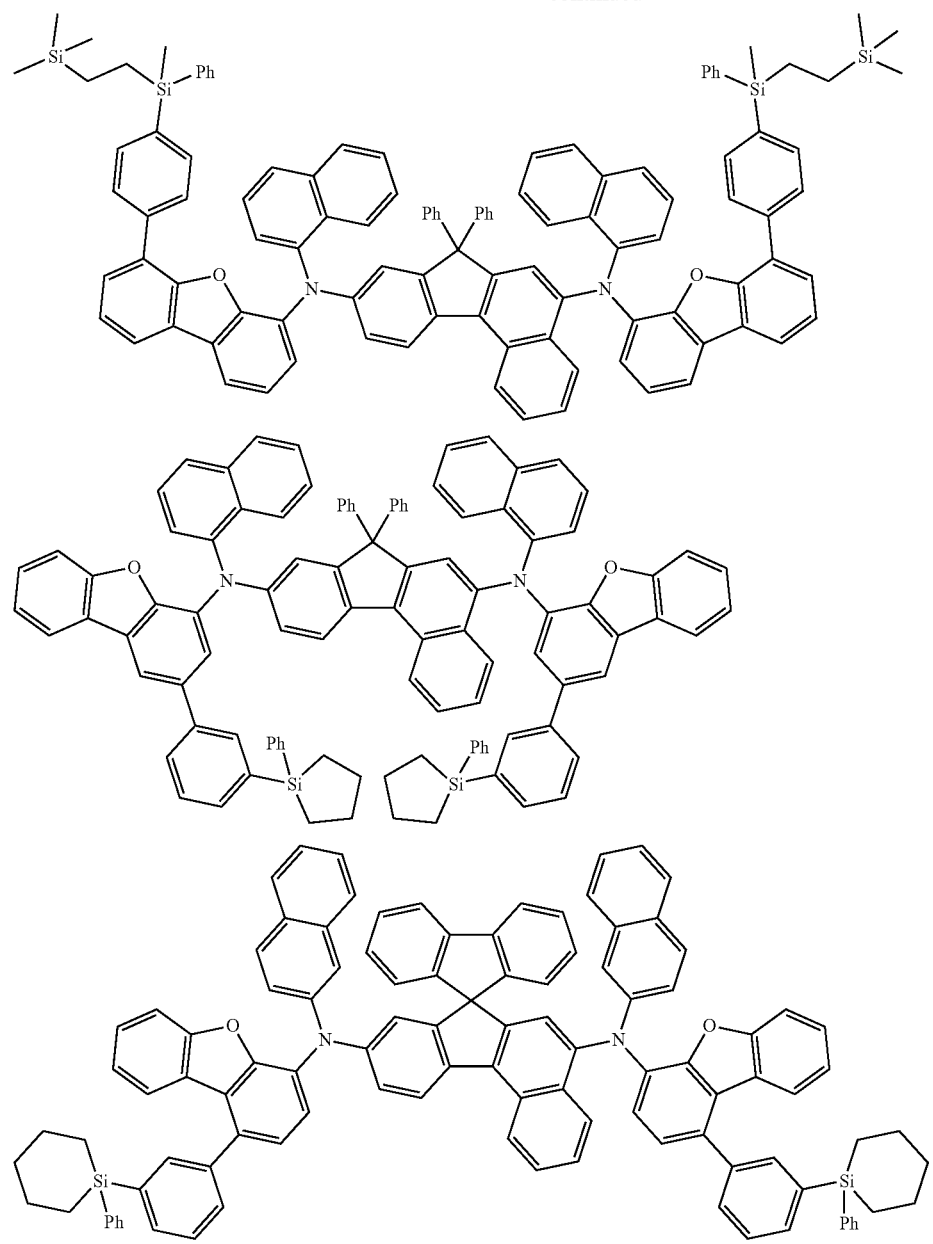
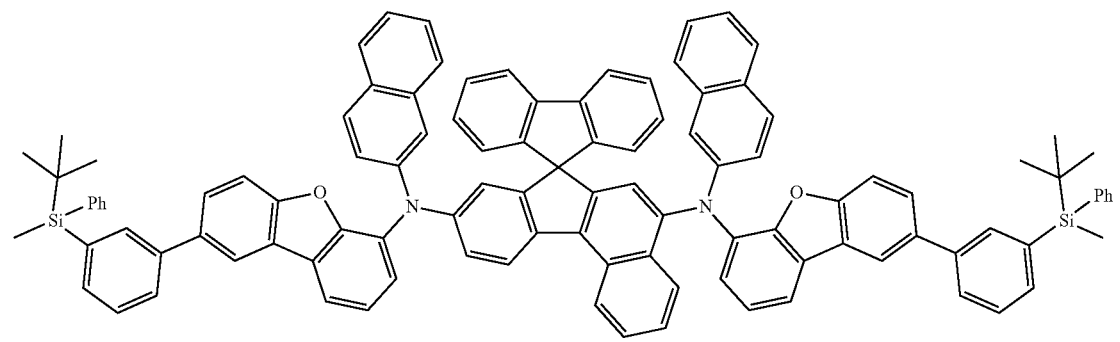

-continued
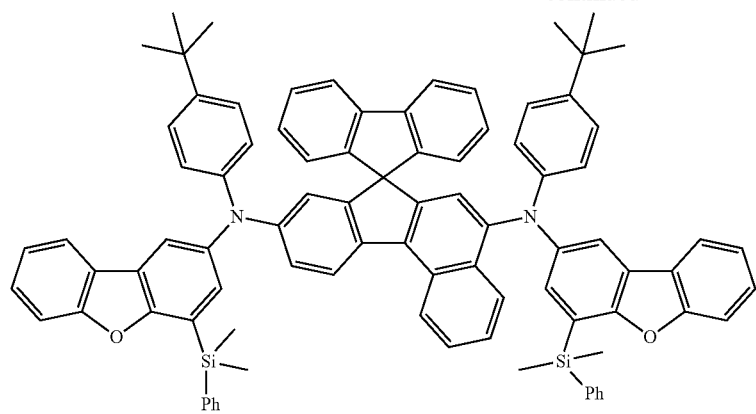
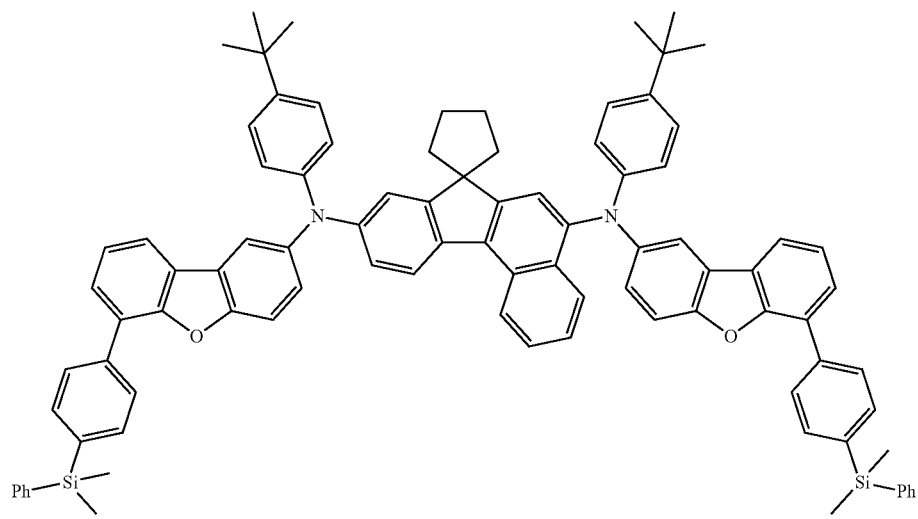
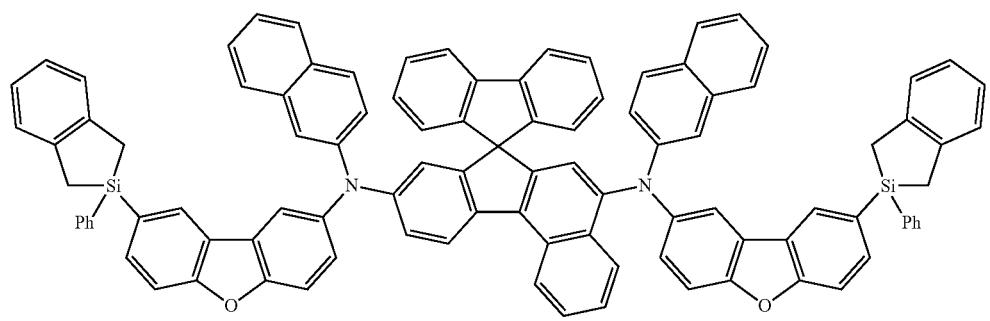
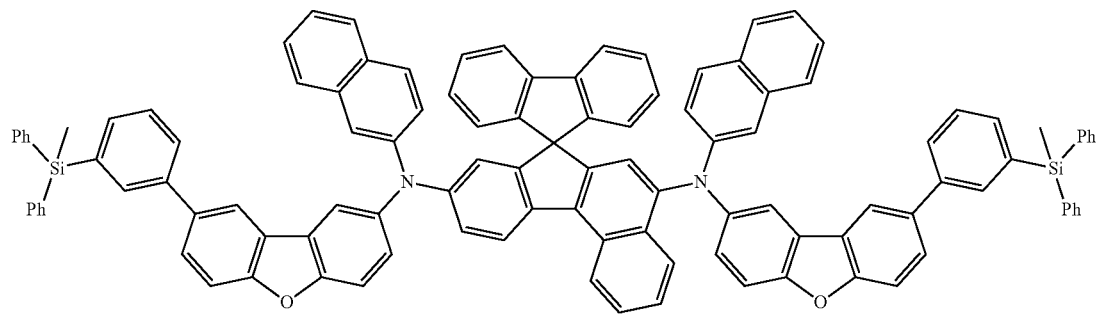

Meanwhile, the compound represented by the Chemical Formula 1 may be prepared by a preparation method as shown in the following Reaction Formula 1:

[Reaction Formula 1]

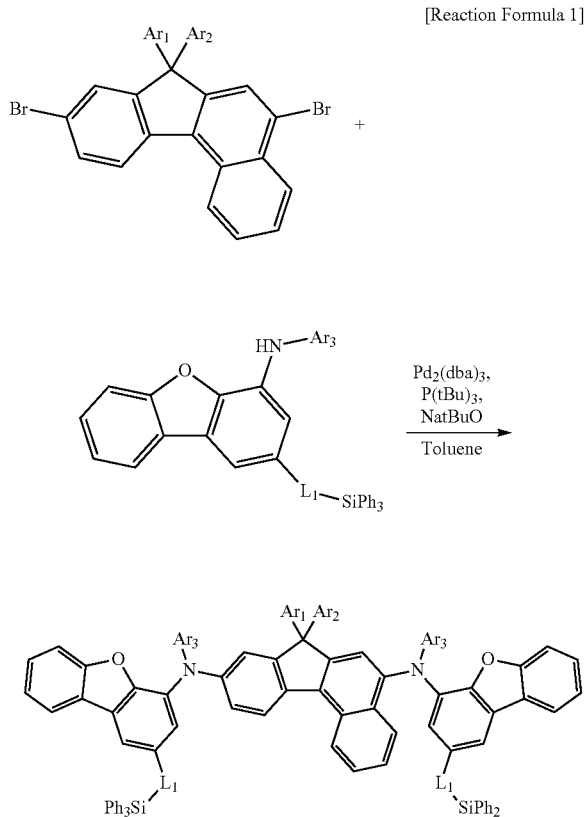

The Reaction Formula 1 is a Suzuki coupling reaction, it is preferable that each reaction is conducted in the presence of a palladium catalyst and base, and a reactor for the Suzuki coupling reaction may be modified according to the knowledge in the art. The preparation method will be explained in detail in Preparation Examples below.

And, there is provided an organic light emitting device comprising the compound represented by the above Chemical Formula 1. For example, there is provided an organic light emitting device comprising a first electrode; a second electrode opposite to the first electrode; and one or more organic material layers between the first electrode and the second electrode, wherein one or more of the organic material layers comprise the compound represented by the Chemical Formula 1.

The compound represented by the Chemical Formula 1 has improved solubility through the introduction of the bulky structure of a silane group, and thus, has increased solution processability. Thus, an organic light emitting device comprising the compound represented by the Chemical Formula 1 may have improved efficiency and lifetime.

And, when a silane group is introduced, glass transition temperature of the material increases, and thus, stability of the material increases, and when a film is manufactured, stability of the film also increases. Thus, it can be anticipated that an organic light emitting device comprising the compound represented by the Chemical Formula 1 has high efficiency and long lifetime.

The organic material layers of the organic light emitting device of the present disclosure may have a monolayer structure, but it may have a multilayer structure wherein two or more organic material layers are stacked. For example, the organic light emitting device of the present disclosure may have a structure comprising a hole injection layer, a hole transport layer, a light emission layer, an electron transport layer, an electron injection layer, and the like as organic material layers. However, the structure of the organic light emitting device is not limited thereto, and it may have fewer number of organic material layers.

And, the organic material layers may comprise a hole injection layer, a hole transport layer, or a layer simultaneously performing functions for hole injection and transport, and the hole injection layer, hole transport layer, or layer simultaneously performing functions for hole injection and transport may comprise a compound represented by the Chemical Formula 1.

And, the organic material layers may comprise a light emission layer, and the light emission layer may comprise a compound represented by the Chemical Formula 1. Wherein, the compound represented by the Chemical Formula 1 may be used as dopant in the light emission layer, and more specifically, the compound represented by the Chemical Formula 1 may be used as dopant in the light emission layer of blue organic light emitting devices.

And, the organic material layers may comprise an electron transport layer or an electron injection layer, and the electron transport layer or electron injection layer may comprise a compound represented by the Chemical Formula 1.

And, the electron transport layer, electron injection layer or layer simultaneously functioning for electron transport or electron injection may comprise a compound represented by the Chemical Formula 1.

And, the organic material layer may comprise a light emission layer and an electron transport layer, and the electron transport layer may comprise a compound represented by the Chemical Formula 1.

And, preferably, the light emission layer may further comprise a compound represented by the following Chemical Formula 3:

[Chemical Formula 3]

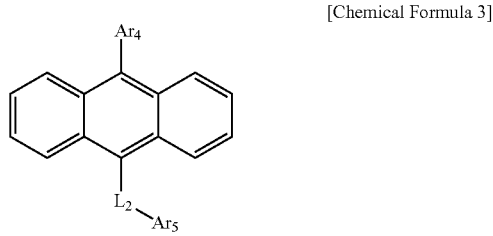

in the Chemical Formula 3, $L_2$ is a single bond; or substituted or unsubstituted $C_{6-60}$ arylene, $Ar_4$ and $Ar_5$ are each independently, substituted or unsubstituted $C_{6-60}$ aryl; or substituted or unsubstituted $C_{5-60}$ heteroaryl comprising one or more heteroatoms selected from the group consisting of N, O and S.

Wherein, the compound represented by the Chemical Formula 3 may be used as host material in the light emission layer, and more specifically, the compound represented by the Chemical Formula 3 may be used as host in the light emission layer of blue organic light emitting devices.

Preferably, $L_2$ may be a single bond; or phenylene.

Preferably, $Ar_4$ and $Ar_5$ may be each independently, one selected from the group consisting of the followings:
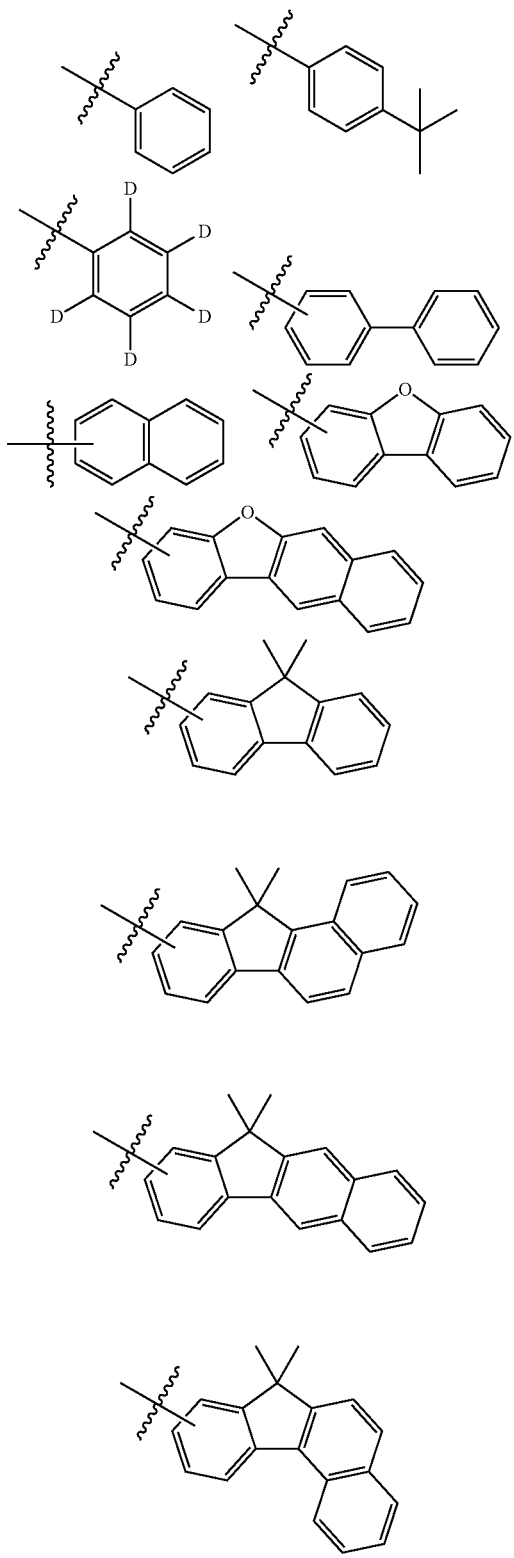
For example, the compound represented by the Chemical Formula 3 may be selected from the group consisting of the following compounds:
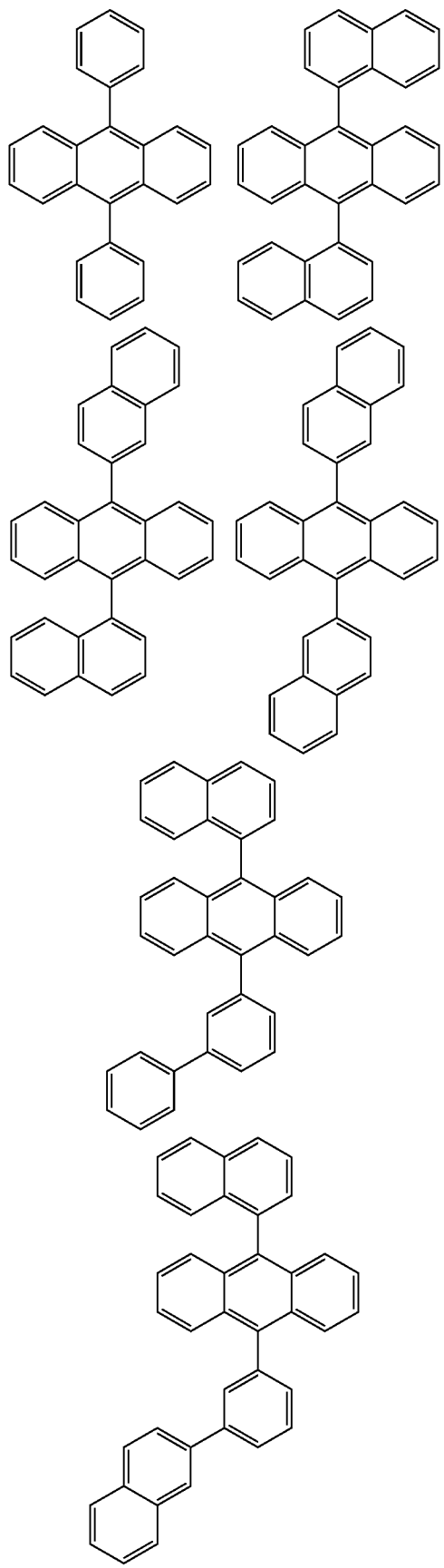

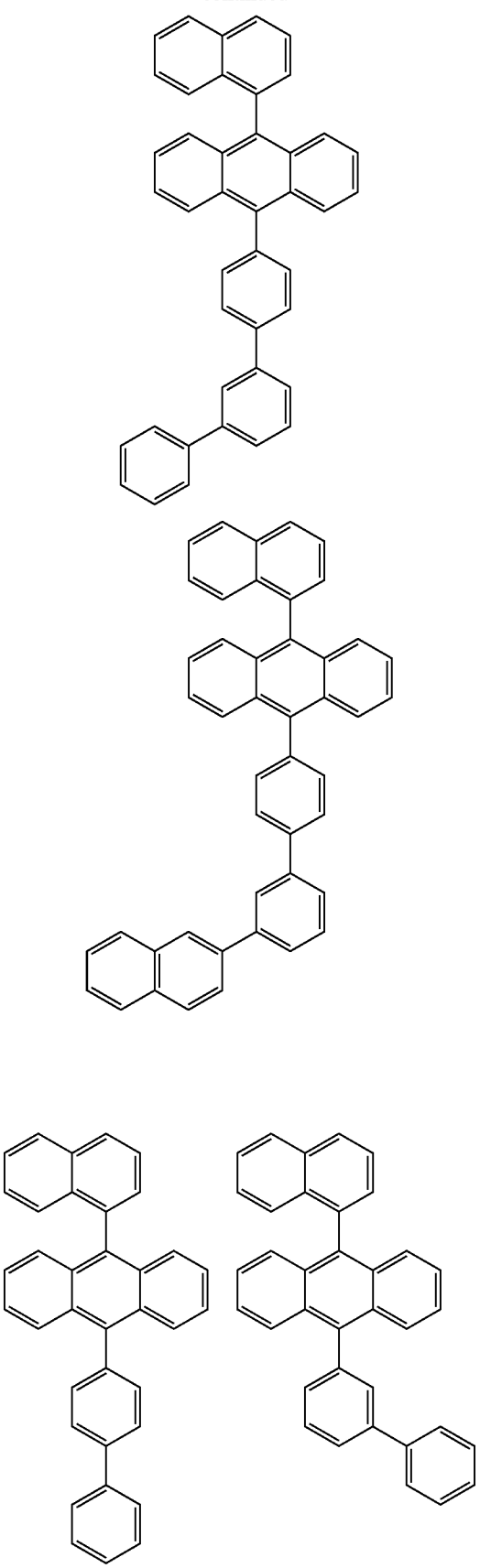
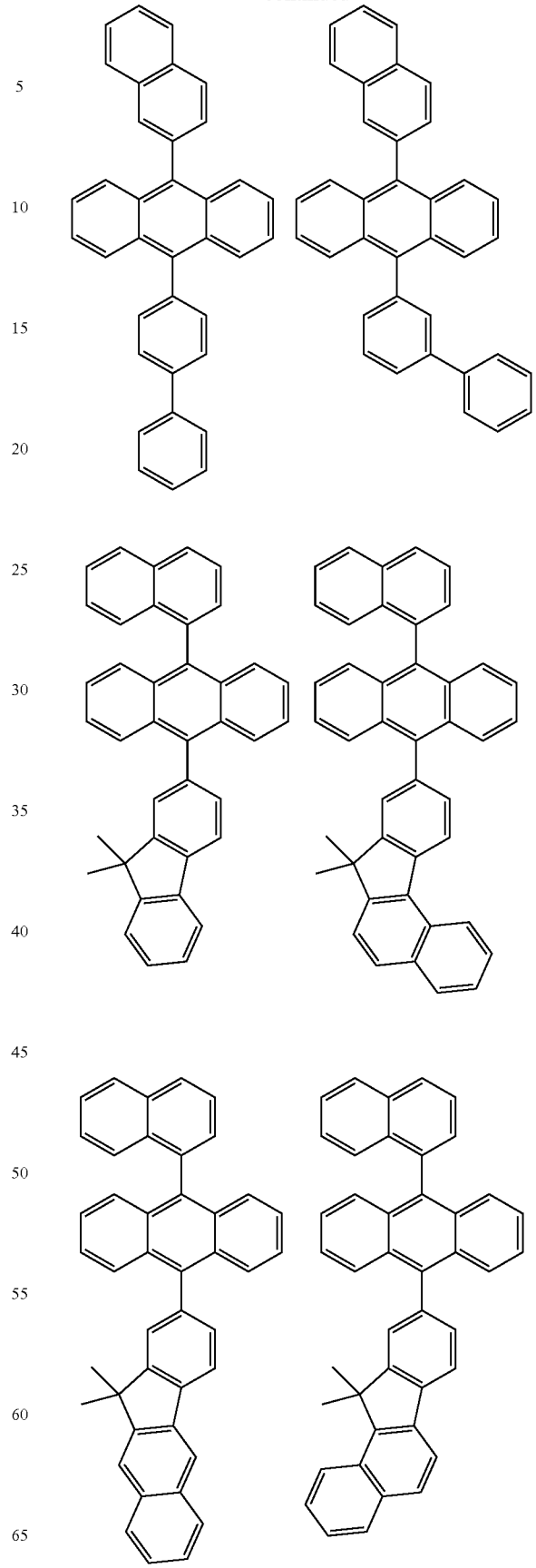

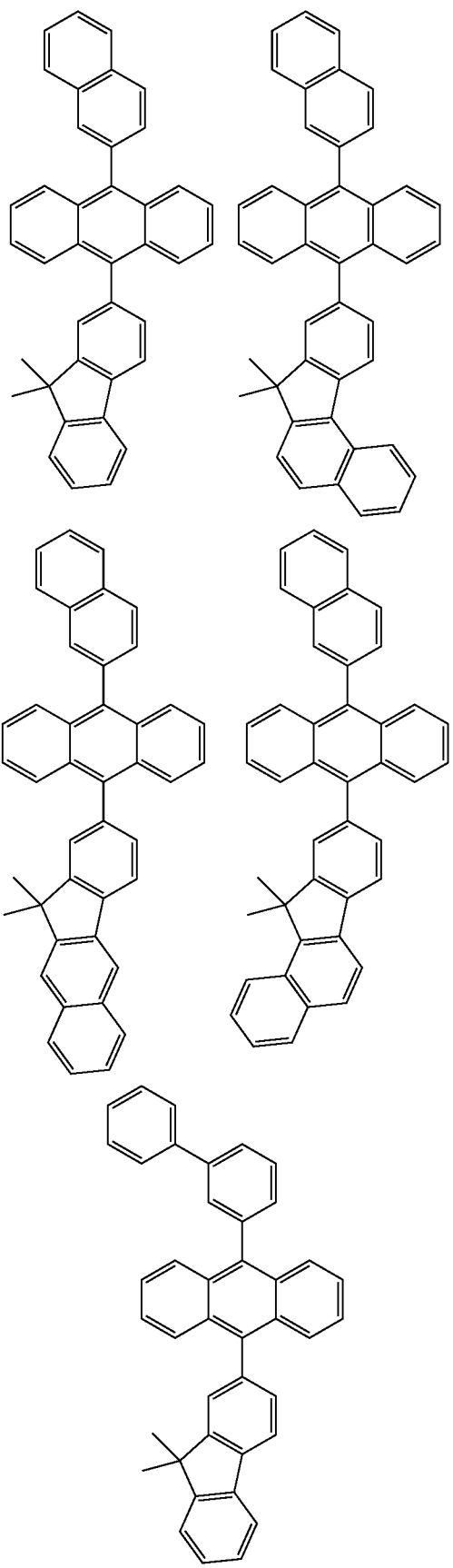
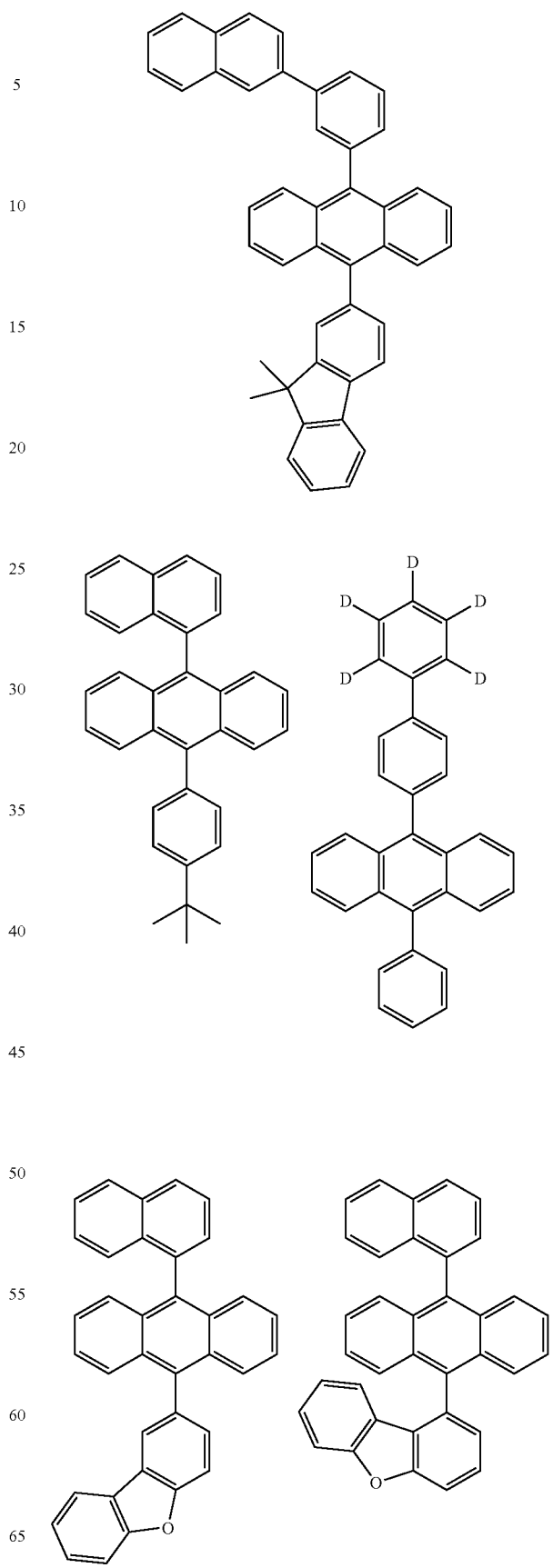

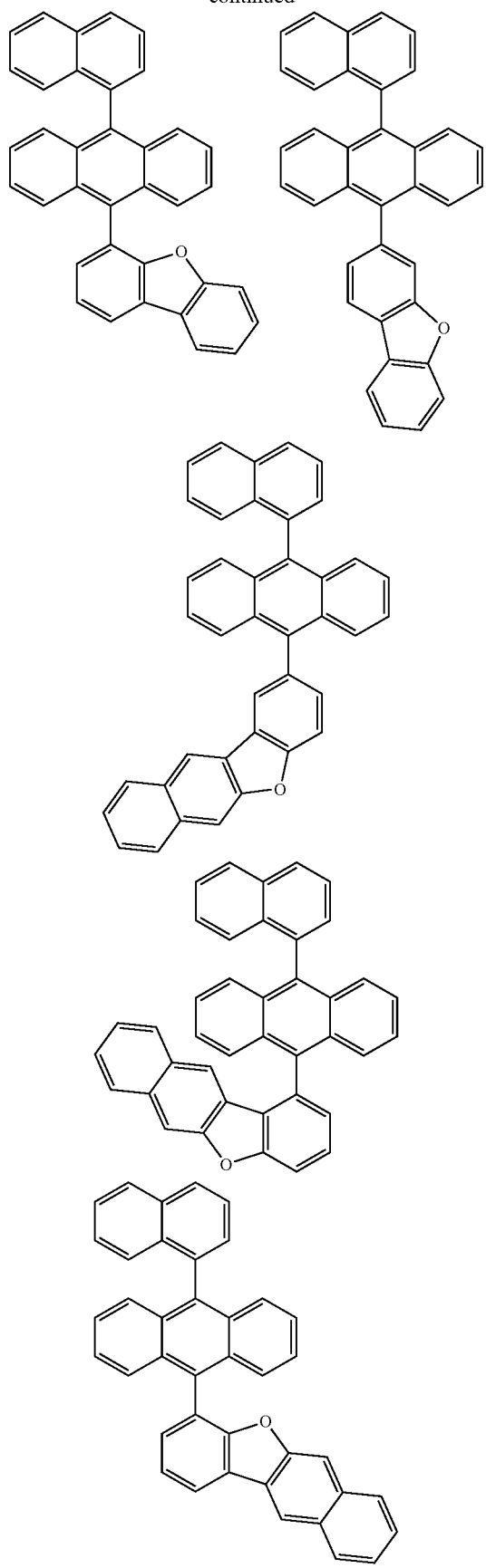
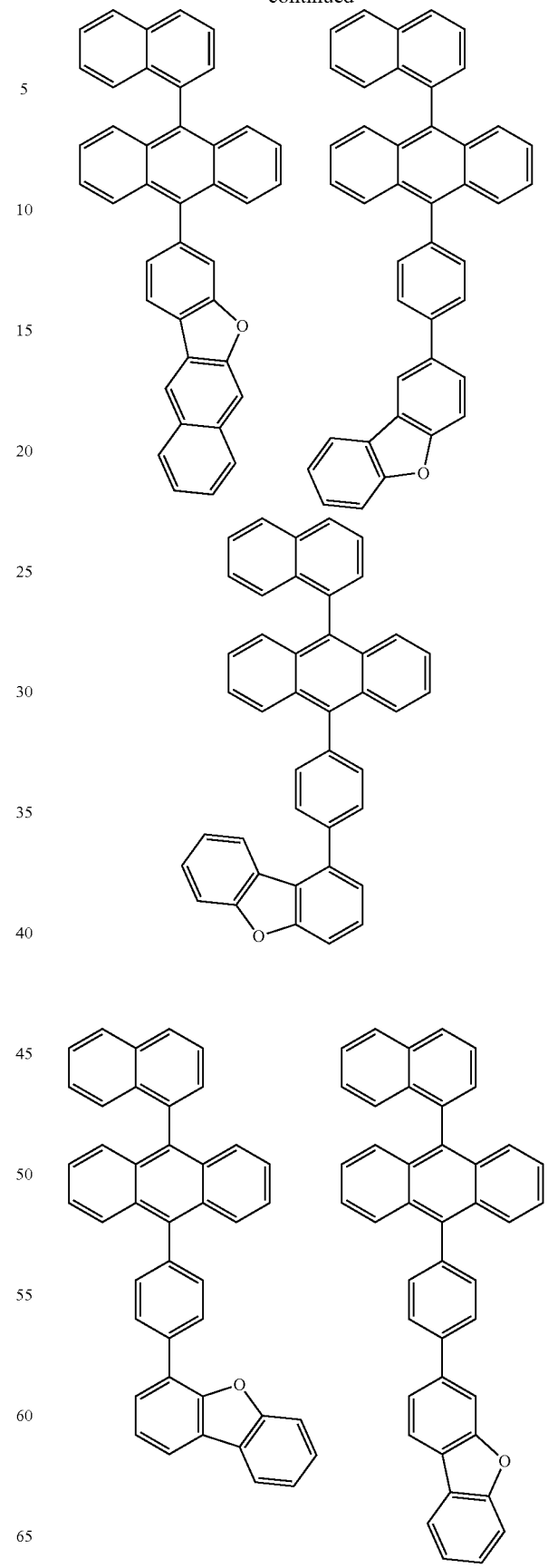

57
-continued
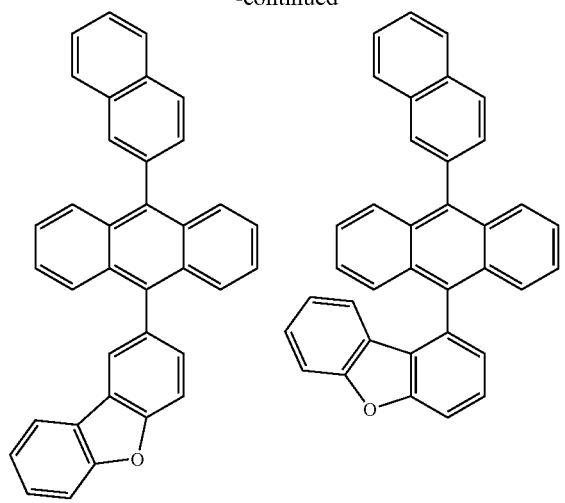
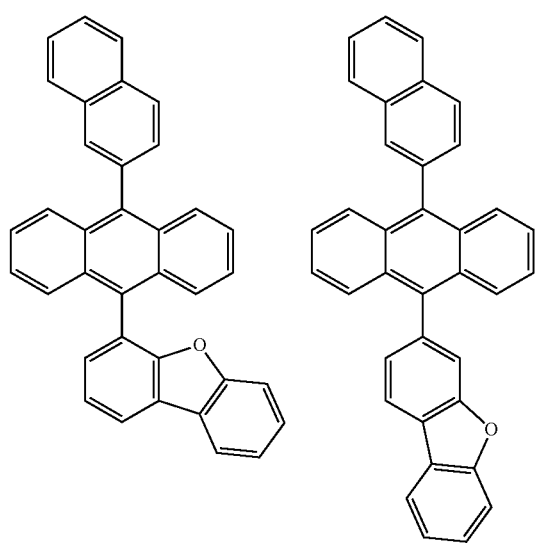
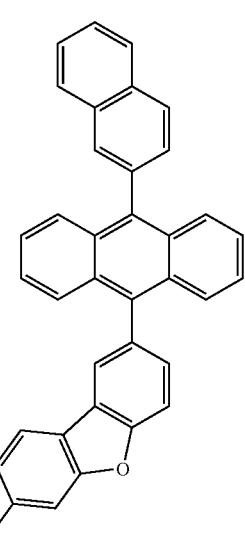
58
-continued
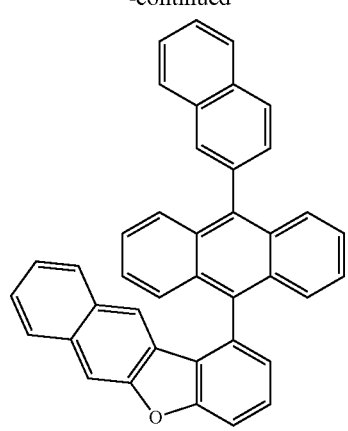
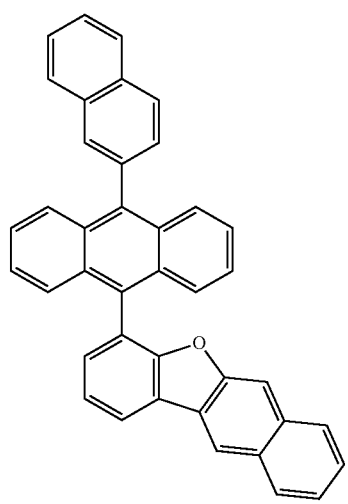
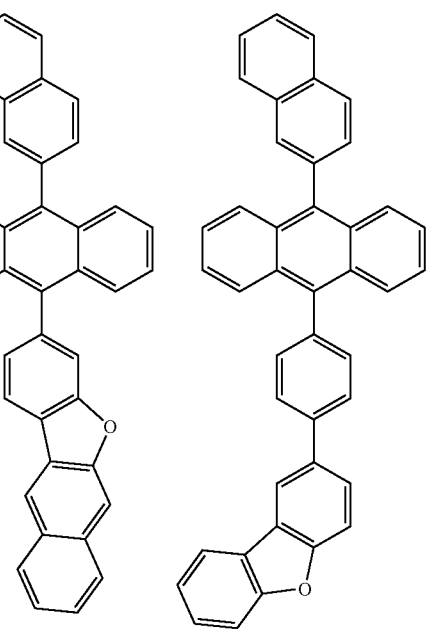

-continued

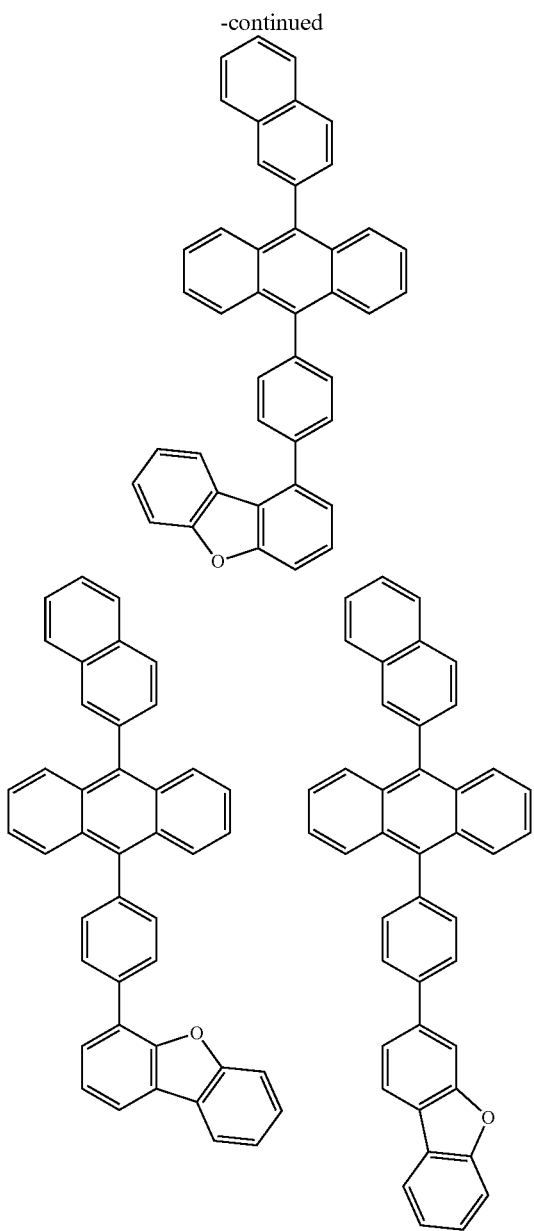

The organic light emitting device according to the present disclosure may be an organic light emitting device of a normal type wherein an anode, one or more organic material layers and a cathode are sequentially stacked on a substrate. And, the organic light emitting device according to the present disclosure may be an organic light emitting device of an inverted type wherein a cathode, one or more organic material layers and an anode are sequentially stacked on a substrate. For example, the structures of the organic light emitting device according to one embodiment of the present disclosure are shown in FIGS. 1 and 2.

FIG. 1 shows the example of an organic light emitting device consisting of a substrate (1), an anode (2), a light emission layer (3), and a cathode (4). In this structure, a compound represented by the Chemical Formula 1 may included in the light emission layer. And, in the light emission layer, a compound represented by the Chemical Formula 3 may be further included.

FIG. 2 shows the example of an organic light emitting device consisting of a substrate (1), an anode (2), a hole injection layer (5), a hole transport layer (6), a light emission layer (7), an electron transport layer (8) and a cathode (4). In this structure, a compound represented by the Chemical Formula 1 may be included in one or more layers of the hole injection layer, hole transport layer, light emission layer and electron transport layer.

The organic light emitting device according to the present disclosure may be prepared using materials and methods known in the art, except that one or more of the organic material layers comprise a compound represented by the Chemical Formula 1. And, in case the organic light emitting device comprises plural organic material layers, the organic material layers may be formed of the same or different materials.

For example, the organic light emitting device according to the present disclosure may be manufactured by sequentially stacking a first electrode, an organic material layer and a second electrode. Wherein, using PVD (physical Vapor Deposition) such as sputtering or e-beam evaporation, metal or conductive metal oxide or alloy thereof may be deposited on a substrate to form an anode, and organic material layers comprising a hole injection layer, a hole transport layer, a light emission layer and an electron transport layer may be formed thereon, and then, material that can be used as a cathode may be deposited thereon. Besides, an organic light emitting device may be manufactured by sequentially depositing cathode material, organic material layers and anode material on a substrate.

And, the compound represented by the Chemical Formula 1 may be formed as organic material layers by solution coating as well as vacuum deposition, when manufacturing an organic light emitting device. Particularly, since the compound represented by the Chemical Formula 1 has excellent solubility in solvents used for solution coating, it is easy to apply solution coating. Wherein, the solution coating means spin coating, dip coating, doctor blading, inkjet printing, screen printing, spray, roll coating, and the like, but is not limited thereto.

Thus, there is provided a coating composition comprising a compound represented by the Chemical Formula 1 and a solvent.

The solvent is not specifically limited as long as it can dissolve or disperse the compounds according to the present disclosure, and for example, chlorine-containing solvents such as chloroform, methylene chloride, 1,2-dichloroethane, 1,1,2-trichloroethane, chlorobenzene, o-dichlorobenzene, and the like; ether-based solvents such as tetrahydrofuran, dioxane, and the like; aromatic hydrocarbon-based solvent such as toluene, xylene, trimethylbenzene, mesitylene, and the like; aliphatic hydrocarbon-based solvent such as cyclohexane, methylcyclohexane, n-pentane, n-hexane, n-heptane, n-octane, n-nonane, n-decane, and the like; ketone-based solvent such as acetone, methylethylketone, cyclohexanone, and the like; ester-based solvents such as ethyl acetate, butyl acetate, ethylcellosolve acetate, and the like; polyhydric alcohols and derivatives thereof such as ethyleneglycol, ethyleneglycol monobutylether, ethyleneglycol monoethylether, ethyleneglycol monomethylether, dimethoxyethane, propyleneglycol, diethoxymethane, triethyleneglycol monoethylether, glycerin, 1,2-hexanediol, and the like; alcohol-based solvents such as methanol, ethanol, propanol, isopropanol, cyclohexanol, and the like; sulfoxide-based solvents such as methyl sulfoxide, and the like; amide-based solvent such as N-methyl-2-pyrrolidone, N,N-dimethylformamide, and the like; benzoate-based solvents such as butyl benzoate, methyl-2-methoxybenzoate, and the like; tetralin; 3-phenoxy-toluene, and the like may be mentioned. And, one kind of the above described solvents may be used alone or two or more kinds thereof may be mixed and used.

And, the viscosity of the coating composition is preferably 1 cP to 10 cP, and within this range, it is easy to coat. And, the concentration of the compound according to the present disclosure in the coating composition may be preferably 0.1 wt/v % to 20 wt/v %.

According to the present disclosure, there is also provided a method for forming functional layers using the above explained coating composition. Specifically, the method comprises the steps of coating the above explained coating composition by a solution process; and heat treating the coated coating composition.

In the heat treatment step, heat treatment temperature may be preferably 150 to 230° C. And, heat treatment time is 1 minute to 3 hours, more preferably 10 minutes to 1 hour. And, it is preferable that the heat treatment is conducted under inert gas atmosphere such as argon, nitrogen, and the like.

Besides, the organic light emitting device may be manufactured by sequentially depositing cathode material, organic material layers, and anode material on a substrate (WO 2003/012890). However, the manufacturing method is not limited thereto.

For example, the first electrode may be an anode and the second electrode may be a cathode, or the first electrode may be a cathode and the second electrode may be an anode.

As the anode material, materials having large work function is preferable so as to facilitate hole injection into organic material layers. Specific examples of the anode materials may include metal such as vanadium, chrome, copper, zinc, gold or alloy thereof; metal oxide such as zinc oxide, indium oxide, indium tin oxide (ITO), or indium zinc oxide (IZO); combinations of metal and oxide such as $ZnO:Al$ or $SnO_2:Sb$; conductive polymer such as poly(3-methylthiophene), poly[3,4-(ethylene-1,2-dioxy)thiophene] (PEDOT), polypyrrole and polyaniline, but are not limited thereto.

As the cathode material, materials having small work function is preferable so as to facilitate electron injection into organic material layers. Specific examples of the cathode materials may include metal such as magnesium calcium sodium potassium, titanium, indium, yttrium, lithium, gadolinium, aluminum, silver, tin and lead, or alloys thereof; multilayered materials such as LiF/Al or $LiO_2/Al$, but are not limited thereto.

The hole injection layer is a layer in which holes are injected from an electrode, and as the hole injection materials, compounds that have a capability of transporting holes, and thus, have hole injection effect from an anode and excellent hole injection effect for a light emission layer or light emission material, prevent movement of excitons generated in the light emission layer to an electron injection layer or electron injection material, and have excellent thin film forming capability may be preferably used. It is preferable that HOMO (highest occupied molecular orbital) of the hole injection material is between the work function of anode material and HOMO of the surrounding organic material layer. Specific examples of the hole injection materials may include metal porphyrin, oligothiophene, arylamin-based organic material, hexanitrile hexaazatriphenylene-based organic material, quinacridone-based organic material, perylene-based organic material, anthraquinone and polyaniline, and polythiophene-based conductive polymer, and the like, but are not limited thereto.

The hole transport layer is a layer that receives holes from the hole injection layer and transports the holes to a light emission layer, and as the hole transport materials, materials that can receive holes from an anode or a hole injection layer and transfer to a light emission layer, and have high hole mobility are preferable. Specific examples may include arylamine-based organic material, conductive polymer, and block copolymer simultaneously comprising conjugated parts and non-conjugated parts, but are not limited thereto.

As the light emission materials, materials that can receive holes and electrons respectively from a hole transport layer and an electron transport layer and bind them, thereby emitting light of visible light region, and have good quantum efficiency for fluorescene or phosphorescence may be preferably used. Specific examples may include 8-hydroxyquinoline aluminum complex ($Alq_3$); carbazole-based compounds; dimerized styryl compounds; BAlq; 10-hydroxybenzo quinoline-metal compounds; benzoxazole, benzthiazole and benzimidazole-based compounds; poly(p-phenylenevinylene)(PPV)-based polymer; spiro compounds; polyfluorene, rubrene, and the like, but are not limited thereto.

The light emission layer may comprise host material and dopant material. The host material may include condensed aromatic ring derivatives or heterocycle-containing compounds, and the like. Specifically, the condensed aromatic ring derivatives may include anthracene derivatives, pyrene derivatives, naphthalene derivatives, pentacene derivatives, phenanthrene derivatives, fluoranthene compounds, and the like, and the heterocycle-containing compounds may include carbazole derivatives, dibenzofuran derivatives, ladder type furan compounds, pyrimidine derivatives, and the like, but are not limited thereto.

The dopant material may include aromatic amine derivatives, styrylamine compounds, boron complex, fluoranthene compounds, metal complex, and the like. Specifically, the aromatic amine derivative may be a condensed aromatic ring derivative having substituted or unsubstituted arylamino group, such as pyrene, anthracene, chrysene, periflanthene having an arylamino group, and the like, and the styrylamine compound may be a compound in which substituted or unsubstituted arylamine is substituted with at least one arylvinyl group, and is unsubstituted or substituted with one or two or more substituents selected from the group consisting of an aryl group, a silyl group, an alkyl group, a cycloalkyl group, and an arylamino group. Specifically, styrylamine, styryldiamine, styryltriamine, styryltetraamine, and the like may be mentioned, but not limited thereto. And, the metal complex may include iridium complex, platinum complex, and the like, but is not limited thereto.

The electron transport layer is a layer that receives electrons from the electron injection layer and transports the electrons to the light emission layer, and as the electron transport materials, materials that can receive electrons from a cathode and transfer to the light emission layer, and have high electron mobility are appropriate. Specific examples thereof may include Al complex of 8-hydroxyquinoline; $Alq_3$ containing complex; organic radical compounds; hydroxyflavone-metal complex, and the like, but are not limited thereto. The electron transport layer may be used together with any desired cathode material, as used according to the prior art. Particularly, examples of appropriate cathode materials are common materials that have low work function and are followed by an aluminum layer or a silver layer. Specifically, cerium, barium, ytterbium and samarium may be mentioned, and in each case, an aluminum layer or a silver layer is followed.

The electron injection layer is a layer in which electrons are injected from an electrode, and as the electron injection materials, materials that have capability of transporting electrons, have electron injection effect from a cathode and excellent electron injection effect for a light emission layer or light emission material, prevent movement of exitons generated in a light emission layer to a hole injection layer, and have excellent capability of forming a thin film are preferable. Specifically, fluorenone, anthraquinodimethane, diphenoquinone, thiopyran dioxide, oxazole, oxadiazole, triazole, imidazole, perylene tetracarboxylic acid, fluorenylidene methane, anthrone, and the like and derivatives thereof, metal complex compounds and nitrogen-containing 5-membered ring derivatives, and the like may be mentioned, but are not limited thereto.

As the metal complex compounds, 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like may be mentioned, but are not limited thereto.

The organic light emitting device according to the present disclosure may be a top emission type, a bottom emission type or a dual emission type according to materials used.

And, the compound represented by the Chemical Formula 1 may be also included in organic solar cells or organic transistors, as well as organic light emitting devices.

Preparation of the compound represented by the Chemical Formula 1 and an organic light emitting device comprising the same will be explained in detail in Examples below. However, the following Examples are presented only as the illustrations of the invention, and the scope of the invention is not limited thereby.

Preparation Example 1

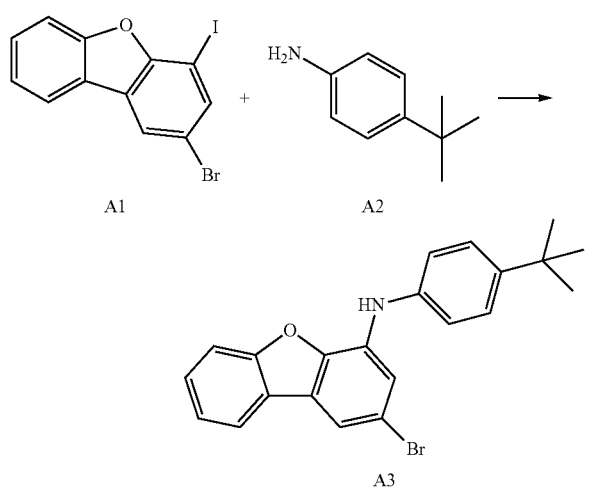

A compound A1 (11.2 g, 30 mmol), a compound A2 (4.48 g, 30 mmol), Pd$_2$dba$_3$ (1.37 g, 1.5 mmol), BINAP (2.8 g, 4.5 mmol), and NatBuO (4.32 g, 45 mmol) were dissolved in toluene (240 ml), and then, stirred at 80° C. for 15 hours. The reaction solution was cooled to a room temperature, distilled water was introduced, an organic layer was separated in a separatory funnel, and moisture was removed with MgSO$_4$, and then, the solvent was removed under reduced pressure. The obtained material was subjected to column chromatography using dichloromethane hexane to separate and purify a compound A3 (9.1 g, 77%). MS: [M+H]+=394

Preparation Example 2

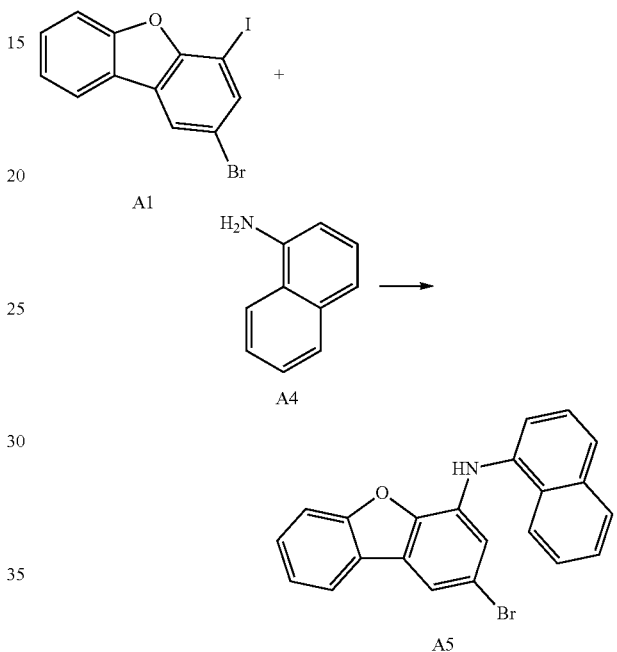

A compound A5 was prepared by the same method as the Preparation Example 1, except that a compound A4 was used instead of the compound A2. MS: [M+H]+=388

Preparation Example 3

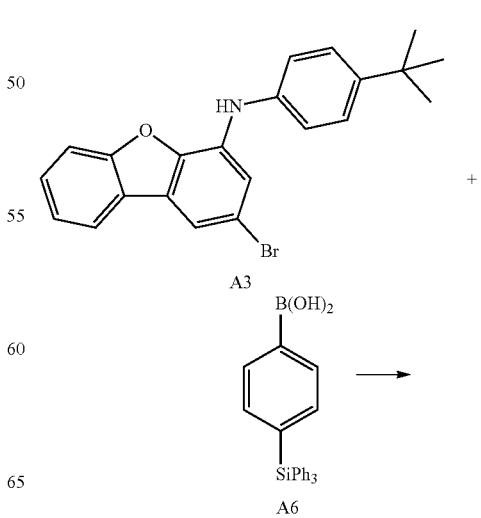

-continued

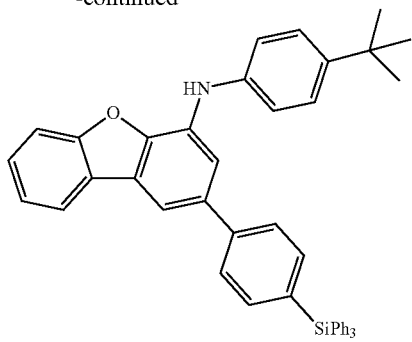

B1

A compound A3 (2 g, 5 mmol), a compound A6 (2.85 g, 7.5 mmol), Pd(PPh$_3$)$_4$ (289 mg, 0.25 mmol) and K$_2$CO$_3$ (2.07 g, 15 mmol) were dissolved in toluene (50 ml) and distilled water (20 ml), and then, stirred at 90° C. for 15 hours. After separating an organic layer, moisture was removed with MgSO$_4$, and then, the solvents was removed under reduced pressure. The obtained material was subjected to column chromatography using dichloromethane hexane to separate and purify a compound B1 (1.8 g, 55%). MS: [M+H]+=650

Preparation Example 4

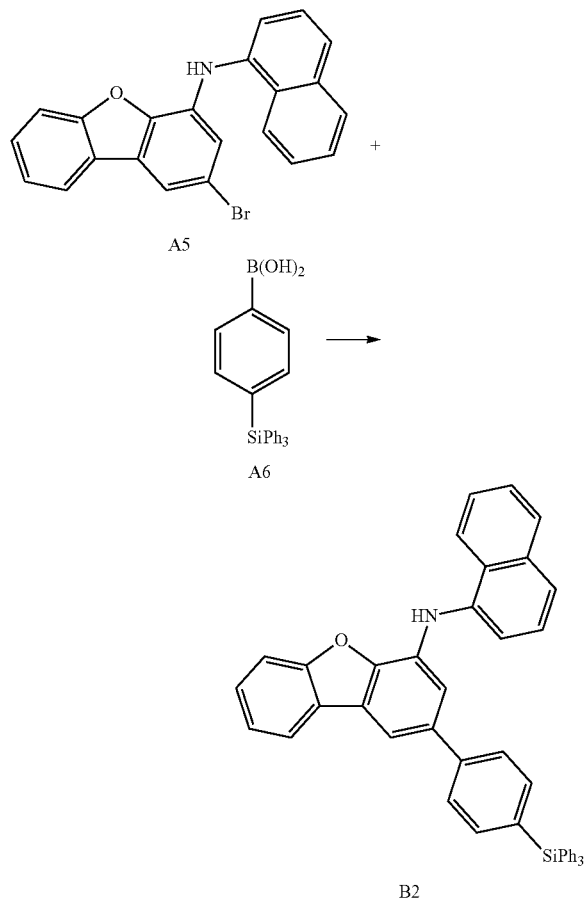

A compound B2 was prepared by the same method as the Preparation Example 3, except that a compound A5 was used instead of the compound A3. MS: [M+H]+=644

Example 1

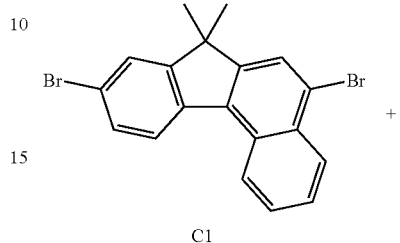

C1

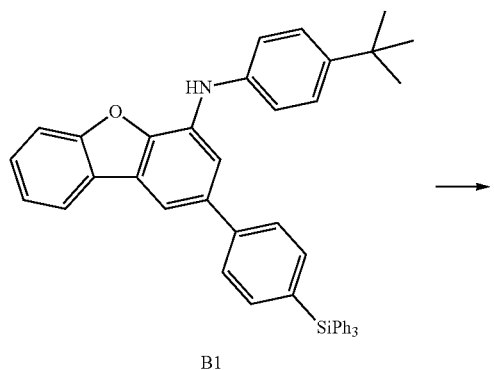

B1

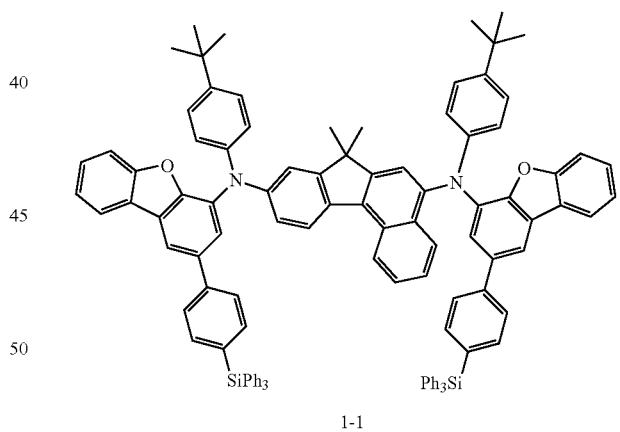

1-1

A compound C1 (1 g, 2.48 mmol), a compound B1 (3.55 g, 5.47 mmol), Pd$_2$(dba)$_3$ (110 mg, 0.12 mmol), P(tBu)$_3$ (73 mg, 0.36 mmol) and NatBuO (0.79 g, 8.21 mmol) were dissolved in toluene (25 ml), and then, stirred at 100° C. for 15 hours. The reaction solution was cooled to a room temperature, distilled water was introduced, an organic layer was separated in a separatory funnel, and moisture was removed with MgSO4, and then, the solvent was removed under reduced pressure. The obtained material was subjected to column chromatography using dichloromethane hexane to separate and purify a compound 1-1 (2.3 g, 60%). MS: [M+H]+=1540

Example 2
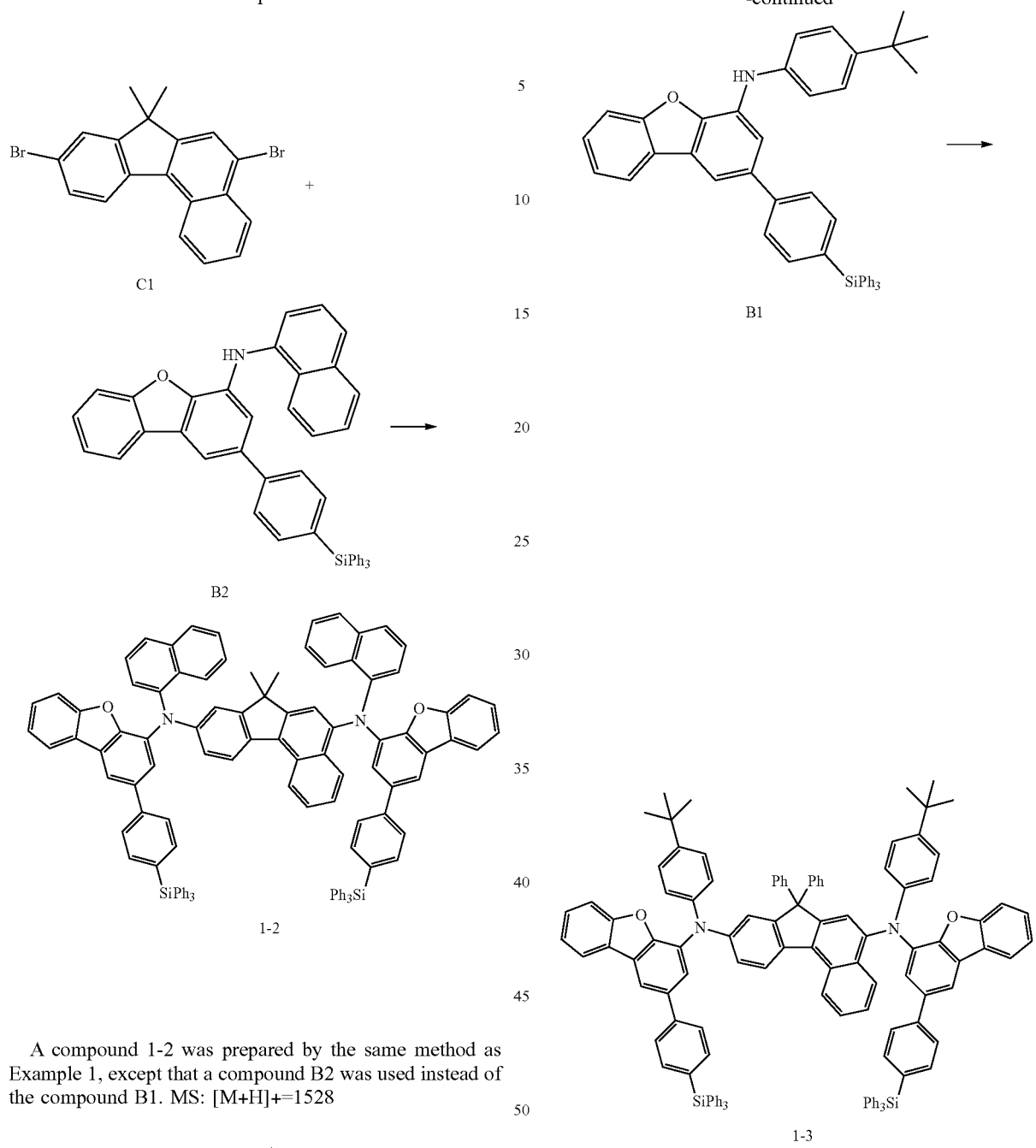
A compound 1-2 was prepared by the same method as Example 1, except that a compound B2 was used instead of the compound B1. MS: [M+H]+=1528
Example 3
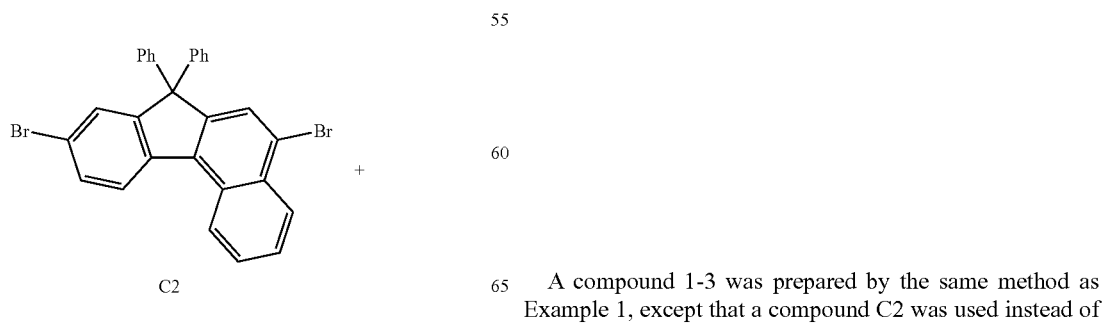
A compound 1-3 was prepared by the same method as Example 1, except that a compound C2 was used instead of the compound C1. MS: [M+H]+=1664

Example 4
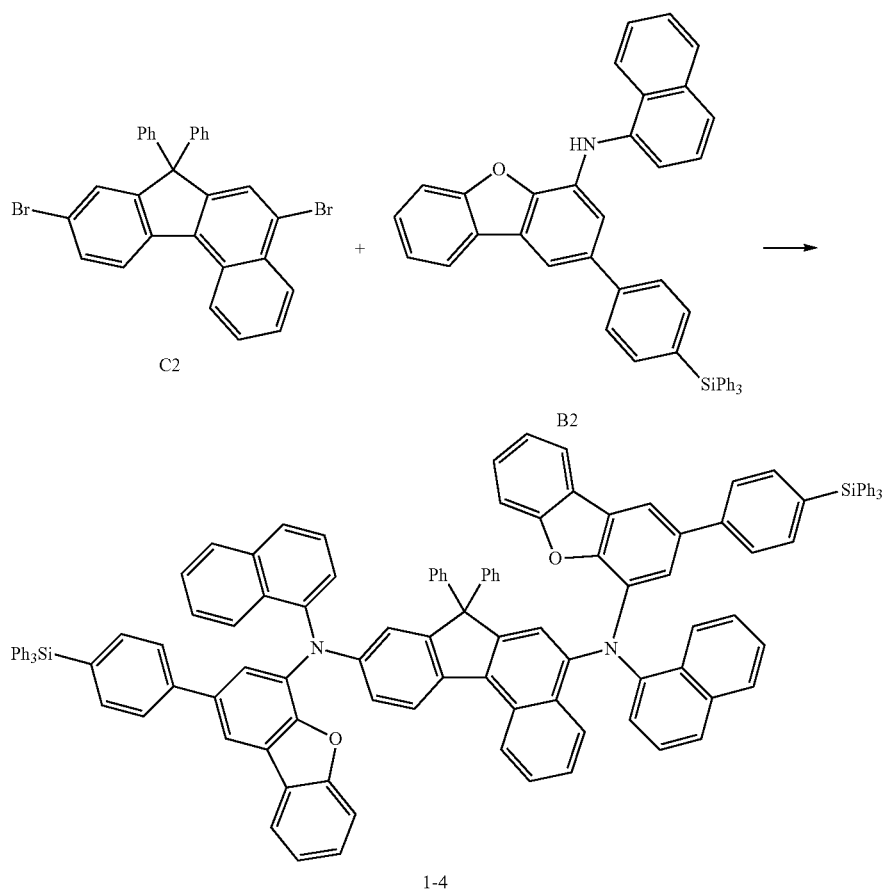
A compound 1-4 was prepared by the same method as Example 3, except that a compound B2 was used instead of the compound B1. MS: [M+H]+=1652
Preparation Example 5
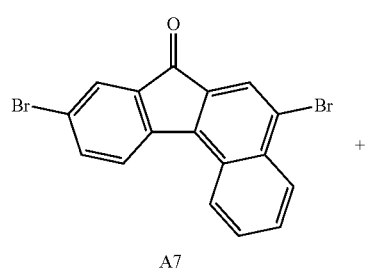
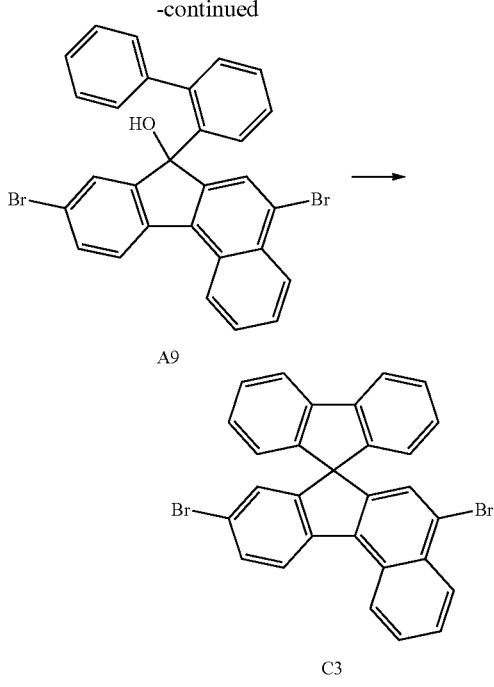

A compound A8 (2.33 g, 10 mmol) was dissolved in tetrahydrofuran (100 mL), and cooled to −78° C. To the cooled reaction solution, 2.5M normal butyllithium (4.4 mL, 11 mmol) was added dropwise and stirred for 1 hour. And then, a compound A7 (3.88 g, 10 mmol) was introduced and stirred at a room temperature. After the reaction was completed, a sodium bicarbonate aqueous solution was introduced to terminate the reaction, and then, extracted with ethyl acetate and water. An organic layer was separated, moisture was removed with MgSO₄, and then, the solvents was removed under reduced pressure. The obtained material was recrystallized with ethyl acetate and hexane to obtain a compound A9. To the compound A9, acetic acid (50 mL) and sulfuric acid (0.05 mL) were introduced, and the reaction solution was stirred under reflux for 2 hours. After the reaction was completed, solid was filtered and washed with water and ethanol, and then, recrystallized with ethyl acetate and hexane to obtain a compound C3 (2.7 g, 52%).

Example 5

A compound 1-5 was prepared by the same method as Example 1, except that a compound C3 was used instead of the compound C1. MS: [M+H]+=1662

Example 6

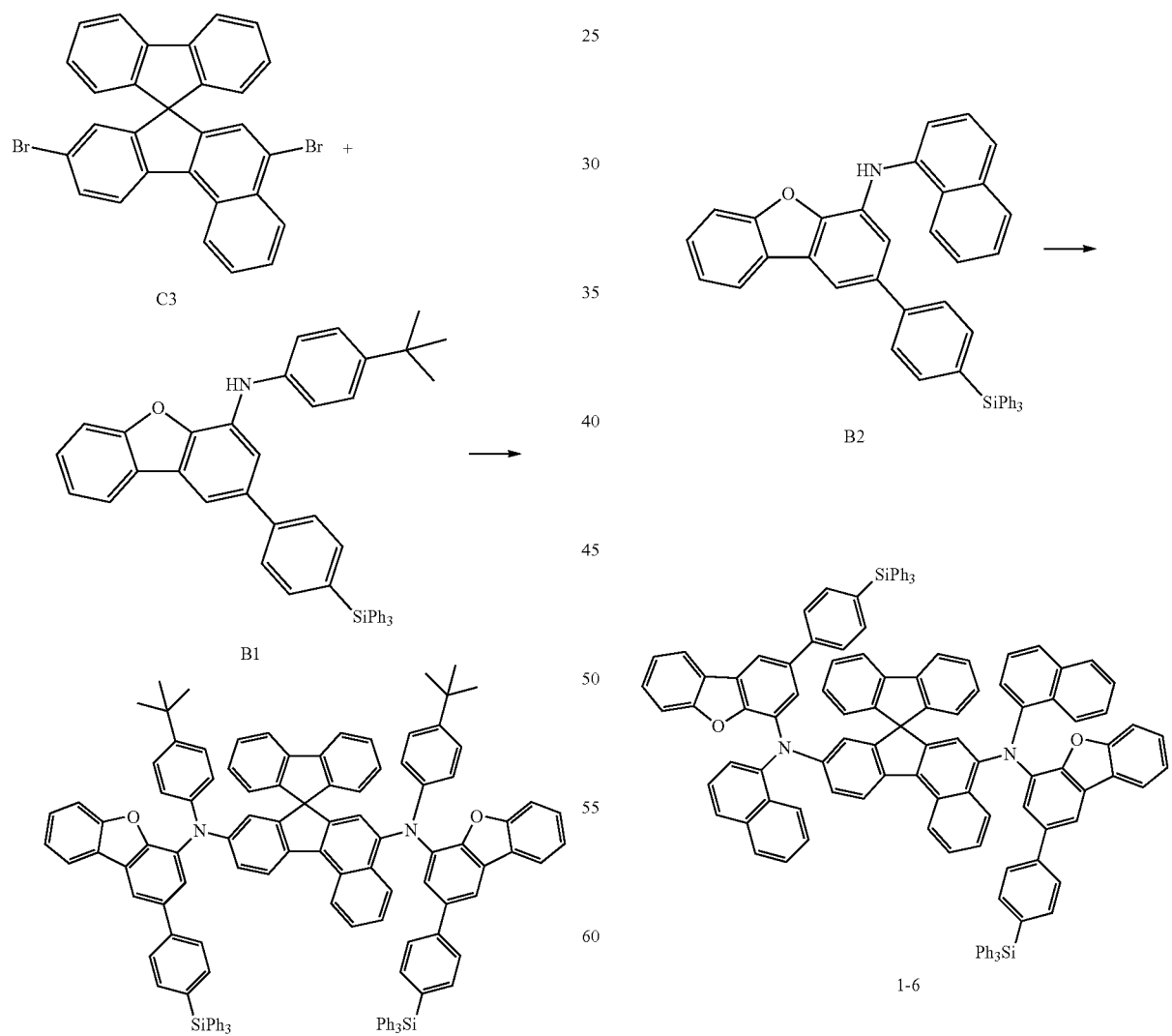

A compound 1-6 was prepared by the same method as Example 5, except that a compound B2 was used instead of the compound B1. MS: [M+H]+=1650

Example 7

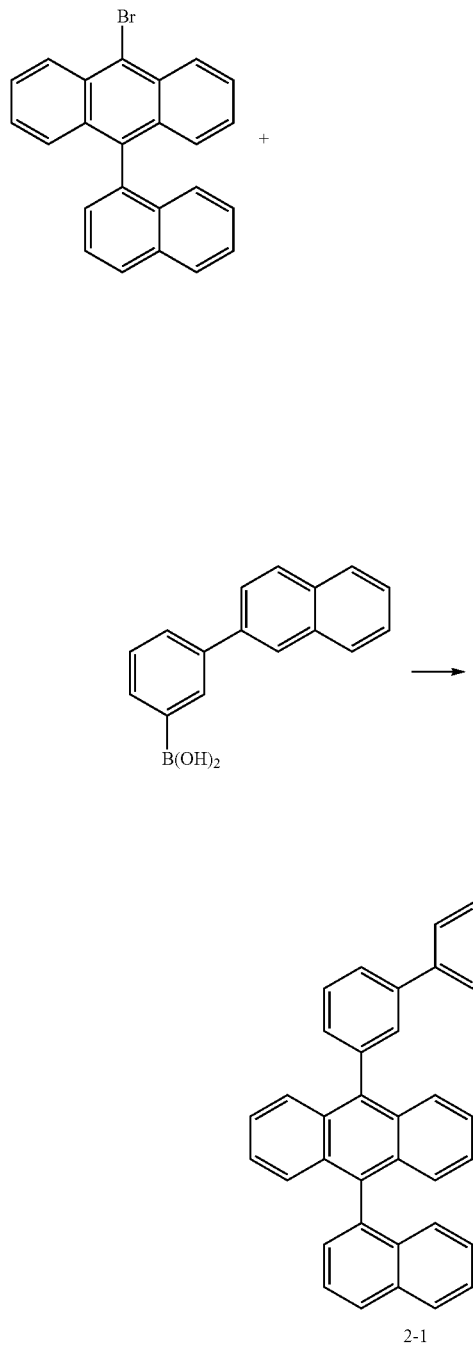

9-bromo-10-(naphthalene-1-yl)anthracene (1.92 g, 5 mmol), ((3-(naphthalene-2-yl)phenyl)boronic acid (1.86 g, 7.5 mmol), Pd(PPh$_3$)$_4$ (0.58 g, 0.5 mmol) and K$_2$CO$_3$ (2.07 g, 15 mmol) were dissolved in toluene (60 ml) and distilled water (20 ml), and then, stirred at 90° C. for 15 hours. After an organic layer was separated, moisture was removed with MgSO$_4$, and then, the solvents was removed under reduced pressure. The obtained material was subjected to column chromatography using dichloromethane hexane to separate and purify a compound 2-1. MS: [M+H]+=507

Example 8

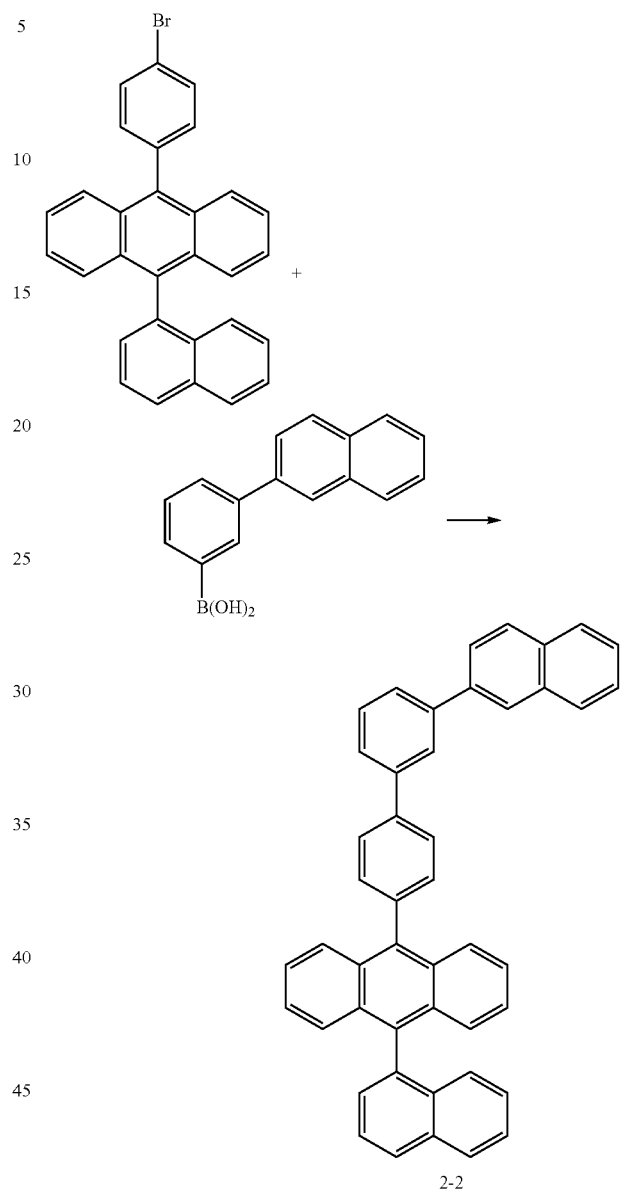

A compound 2-2 was prepared by the same method as Example 7, except that 9-(4-bromophenyl)-10-(naphthalene-1-yl)anthracene (2.3 g, 5 mmol) was used instead of 9-bromo-10-(naphthalene-1-yl)anthracene. MS: [M+H]+=583

Experimental Example 1

A glass substrate coated with an ITO (indium tin oxide) thin film to a thickness of 50 nm was put in distilled water in which detergent was dissolved, and ultrasonically cleaned. Wherein, detergent from Fischer Co. was used, and distilled water filtered twice with a filter (product from Millipore Co.) was used. After washing ITO for 30 minutes, ultrasonic cleaning was progressed with distilled water twice for 10 minutes. After cleaning with distilled water was finished, ultrasonic cleaning was progressed with isopropyl alcohol, acetone, and methanol solvents, and dried and then, transferred to a plasma cleaner. And, the substrate was cleaned using oxygen plasma for 5 minutes, and then, transferred to a vacuum deposition device.

On the prepared ITO transparent electrode, an aqueous dispersion of electrically conductive polymer and sulfonic acid polymer was spin coated at 1000 rpm for 60 seconds, baked at 80° C. for 2 minutes, and baked at 120° C. for 15 minutes to form a hole injection layer. On the hole injection layer, a triarylamine polymer solution was spin coated and baked to form a hole transport layer. On the hole transport layer, a 2 wt % toluene solution of the above described compound 2-1 and compound 1-1 at a weight ratio of 95:5 was spin coated at 5000 rpm, baked at 80° C. for 2 minutes, and baked at 120° C. for 30 minutes to form a light emission layer. It was dried at 130° C. for 10 minutes under nitrogen atmosphere, and then, lithium fluoride (LiF) was deposited to a film thickness of about 1 nm, and finally, aluminum was deposited to a thin thickness of 100 nm, thus forming a cathode. In this process, while maintaining deposition speeds of lithium fluoride at 0.3 Å/sec, and aluminum at 2 Å/sec, and maintaining degree of vacuum at $2\times10^{-7}\sim5\times10^{-6}$ torr during deposition, an organic light emitting device was manufactured.

Device structure: ITO (50 nm)/HIL (40 nm)/HTL (20 nm)/EML (55 nm)/LiF (1 nm)/Al (100 nm)

Experimental Examples 2 to 12

Organic light emitting devices were manufactured by the same method as Experimental Example 1, except that the compounds used for the manufacture of light emission layers were changed as shown in the following Table 1.

Comparative Experimental Examples 1 to 4

Organic light emitting devices were manufactured by the same method as Experimental Example 1, except that the compounds used for the manufacture of light emission layers were changed as shown in the following Table 1.

The structures of BD1 and BD2 are as follows.

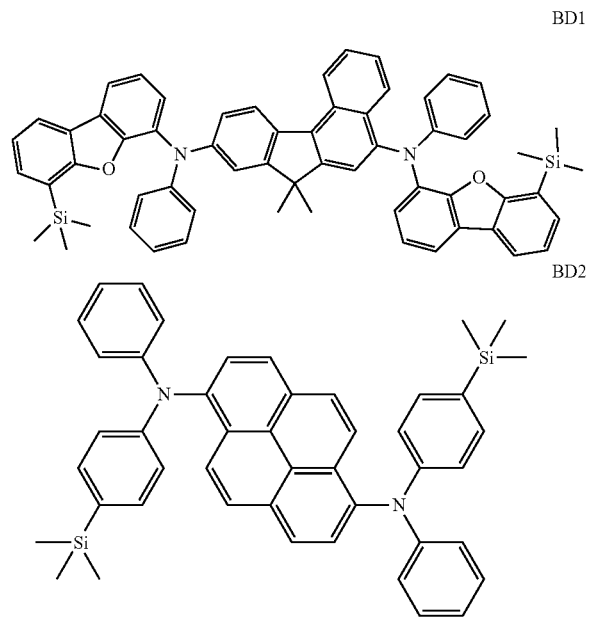

For the organic light emitting devices manufactured in Experimental Examples 1 to 12 and Comparative Experimental Examples 1 to 4, driving voltage at the current density of 10 mA/cm$^2$, current efficiency and quantum efficiency were measured, and a time when luminance became 95% of the initial luminance, at the current density of 10 mA/cm$^2$, was measured, and the results were shown in the following Table 1.

TABLE 1

| | Light emission layer compound | | voltage (V) | Power efficiency (lm/W) | Luminous efficiency (cd/A) | Quantum efficiency (%) | life time (hr) |
|---|---|---|---|---|---|---|---|
| Experimental Example 1 | compound 2-1 | compound 1-1 | 4.35 | 3.43 | 4.74 | 5.83 | 144 |
| Experimental Example 2 | compound 2-2 | compound 1-1 | 4.56 | 3.98 | 5.78 | 6.50 | 132 |
| Experimental Example 3 | compound 2-1 | compound 1-2 | 4.60 | 4.40 | 6.44 | 6.24 | 154 |
| Experimental Example 4 | compound 2-2 | compound 1-2 | 4.39 | 3.31 | 4.62 | 5.74 | 165 |
| Experimental Example 5 | compound 2-1 | compound 1-3 | 4.53 | 3.33 | 4.81 | 5.81 | 157 |
| Experimental Example 6 | compound 2-2 | compound 1-3 | 4.22 | 3.81 | 5.11 | 5.97 | 132 |
| Experimental Example 7 | compound 2-1 | compound 1-4 | 4.64 | 3.78 | 5.58 | 6.86 | 146 |
| Experimental Example 8 | compound 2-2 | compound 1-4 | 4.24 | 4.39 | 5.92 | 6.91 | 130 |
| Experimental Example 9 | compound 2-1 | compound 1-5 | 4.30 | 4.08 | 5.58 | 6.55 | 149 |
| Experimental Example 10 | compound 2-2 | compound 1-5 | 4.42 | 4.07 | 5.72 | 6.67 | 140 |
| Experimental Example 11 | compound 2-1 | compound 1-6 | 4.45 | 4.39 | 6.22 | 6.67 | 165 |
| Experimental Example 12 | compound 2-2 | compound 1-6 | 4.41 | 4.49 | 6.30 | 6.89 | 174 |
| Comparative Experimental Example 1 | compound 2-1 | compound BD1 | 4.46 | 2.88 | 4.09 | 5.28 | 113 |
| Comparative Experimental Example 2 | compound 2-2 | compound BD1 | 4.46 | 3.30 | 4.69 | 5.45 | 121 |
| Comparative Experimental Example 3 | compound 2-1 | compound BD2 | 4.50 | 3.74 | 5.36 | 5.67 | 84 |
| Comparative Experimental Example 4 | compound 2-2 | compound BD2 | 4.44 | 2.94 | 4.15 | 5.06 | 100 |

As shown in the Table 1, it can be confirmed that organic light emitting devices using the compounds represented by the Chemical Formula 1 of the present disclosure as dopants of light emission layers exhibit excellent properties in terms of lifetime.

[DESCRIPTION OF SYMBOLS]

| | |
|---|---|
| 1: substrate | 2: anode |
| 3: light emission layer | 4: cathode |
| 5: hole injection layer | 6: hole transport layer |
| 7: light emission layer | 8: electron transport layer |

The invention claimed is:

1. A compound represented by the following Chemical Formula 1:

[Chemical Formula 1]

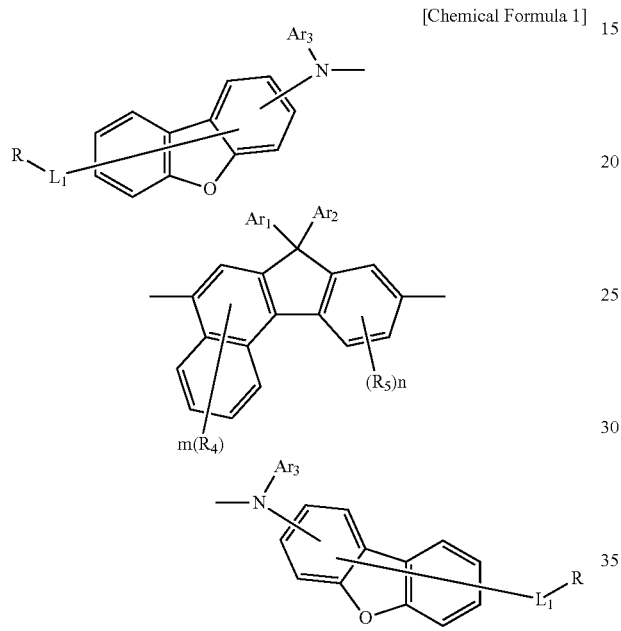

in the Chemical Formula 1,

R is $Si(R_1)(R_2)(R_3)$, $R_1$ to $R_3$ are each independently, hydrogen; deuterium; substituted or unsubstituted $C_{1-60}$ alkyl; or substituted or unsubstituted $C_{6-60}$ aryl; (tri($C_{1-60}$ alkyl)silyl)-($C_{1-10}$ alkylene)-; or (tri($C_{6-60}$ aryl)silyl)-($C_{1-10}$ alkylene)-, or $R_1$ and $R_2$ are linked to form a ring, provided that all of $R_1$ to $R_3$ are not substituted or unsubstituted $C_{1-60}$ alkyl, $L_1$ is a single bond; phenylene; or naphthalenediyl, m and n are each independently, an integer of 0 to 3, $R_4$ and $R_5$ are each independently, hydrogen; deuterium; halogen; cyano; substituted or unsubstituted $C_{1-60}$ alkyl; substituted or unsubstituted $C_{1-60}$ alkoxy; substituted or unsubstituted $C_{1-60}$ thioalkyl; substituted or unsubstituted $C_{3-60}$ cycloalkyl; substituted or unsubstituted $C_{6-60}$ aryl; or substituted or unsubstituted $C_{5-60}$ heteroaryl comprising one or more heteroatoms selected from the group consisting of N, O and S, $Ar_3$ is deuterium; $C_{1-10}$ alkyl; substituted or unsubstituted $C_{6-60}$ aryl; or substituted or unsubstituted $C_{5-60}$ heteroaryl comprising one or more heteroatoms selected from the group consisting of N, O and S, $Ar_1$ and $Ar_2$ are each independently, hydrogen; deuterium; substituted or unsubstituted $C_{1-60}$ alkyl; substituted or unsubstituted $C_{3-60}$ cycloalkyl; or substituted or unsubstituted $C_{6-60}$ aryl; or substituted or unsubstituted $C_{5-60}$ heteroaryl comprising one or more heteroatoms selected from the group consisting of N, O and S, or linked with each other to form $C_{3-60}$ cycloalkyl or a substituent represented by the following Chemical Formula 2,

[Chemical Formula 2]

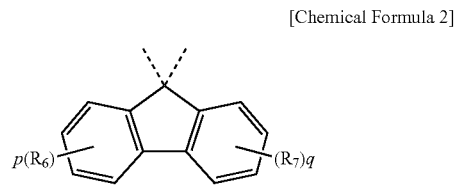

p and q are each independently, an integer of 0 to 4, $R_6$ and $R_7$ are each independently, hydrogen; deuterium; halogen; cyano; substituted or unsubstituted $C_{1-60}$ alkyl; substituted or unsubstituted $C_{1-60}$ alkoxy; substituted or unsubstituted $C_{1-60}$ thioalkyl; substituted or unsubstituted $C_{3-60}$ cycloalkyl; substituted or unsubstituted $C_{6-60}$ aryl; or substituted or unsubstituted $C_{5-60}$ heteroaryl comprising one or more heteroatoms selected from the group consisting of N, O and S.

2. The compound according to claim 1, wherein the Chemical Formula 1 is represented by any one of the following Chemical Formulas 1-1 to 1-5:

[Chemical Formula 1-1]

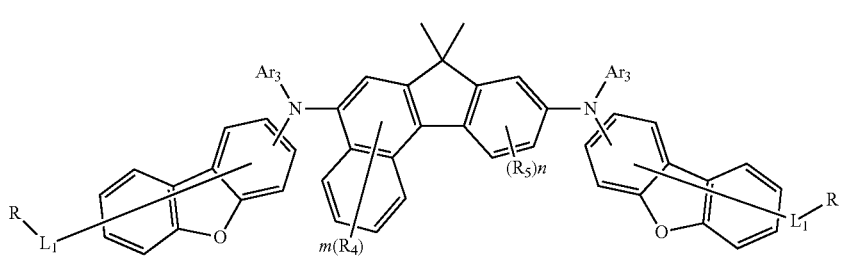

[Chemical Formula 1-2]

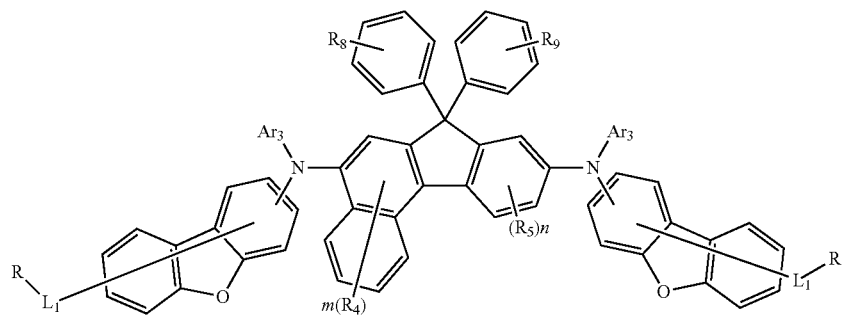

[Chemical Formula 1-3]

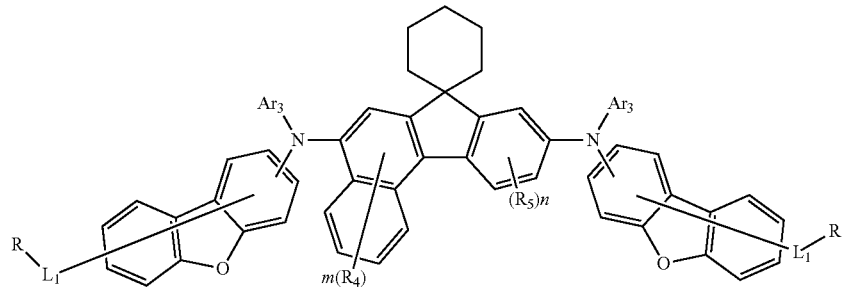

[Chemical Formula 1-4]

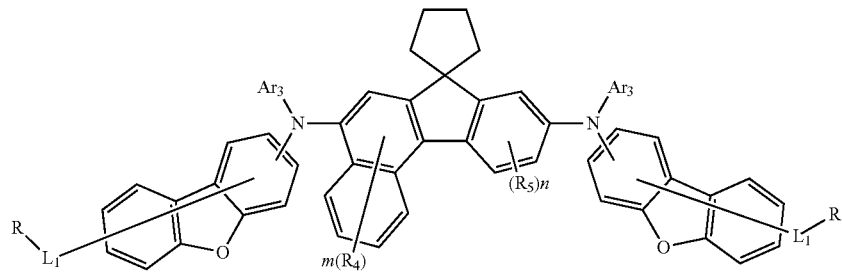

[Chemical Formula 1-5]

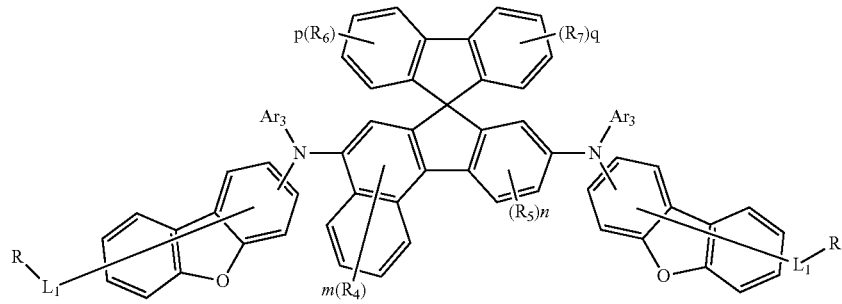

in the Chemical Formula 1-1 to 1-5, $R_8$ and $R_9$ are each independently, hydrogen; or substituted or unsubstituted $C_{1-60}$ alkyl, m, n, p, q, R, $R_4$ to $R_7$, $L_1$ and $Ar_3$ are as defined in claim 1.

3. The compound according to claim 1, wherein $R_1$ to $R_3$ are each independently, methyl; i-propyl; t-butyl; phenyl; or trimethylsilyl-ethylene.

4. The compound according to claim 1, wherein at least one of $R_1$ to $R_3$ is phenyl.

5. The compound according to claim 1, wherein $L_1$ is a single bond; or phenylene.

6. The compound according to claim 1, wherein both m and n are 0.

7. The compound according to claim 1, wherein $R_6$ and $R_7$ are each independently, hydrogen; or $C_{1-10}$ alkyl.

8. The compound according to claim 1, wherein Ara is deuterium; $C_{1-10}$ alkyl; or phenyl unsubstituted or substituted with tri($C_{1-5}$alkyl)silyl; or naphthyl.

9. The compound according to claim 1, wherein the compound represented by the Chemical Formula 1 is one selected from the group consisting of the following compounds:

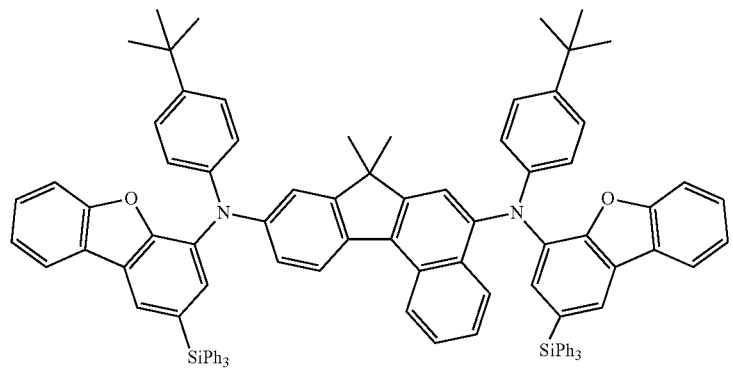
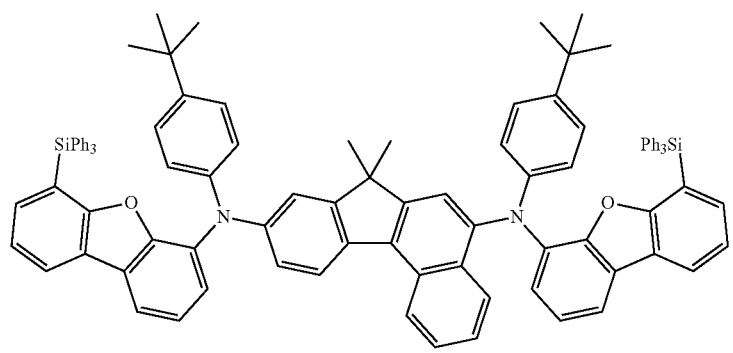
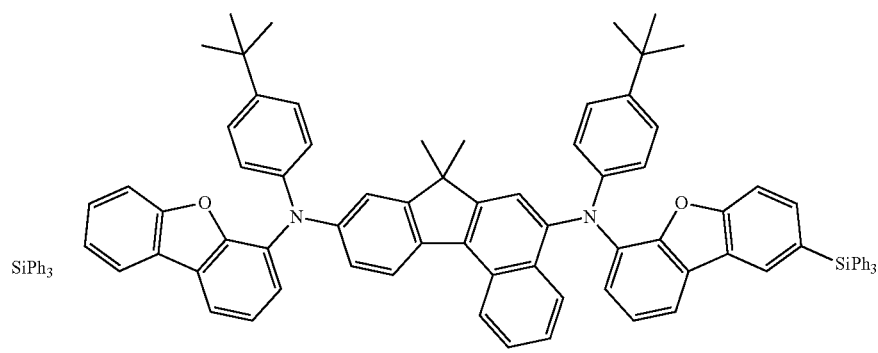
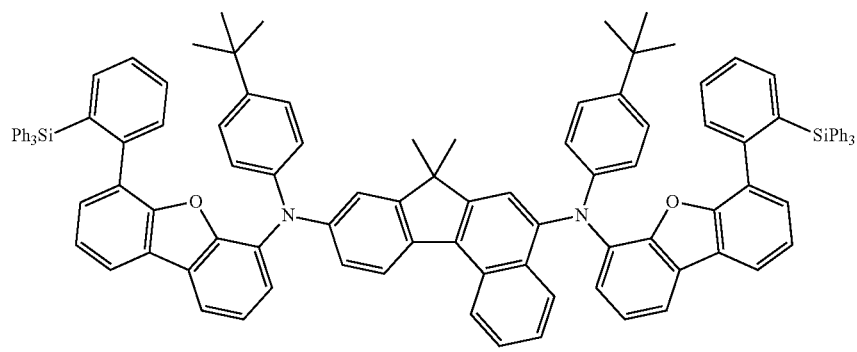

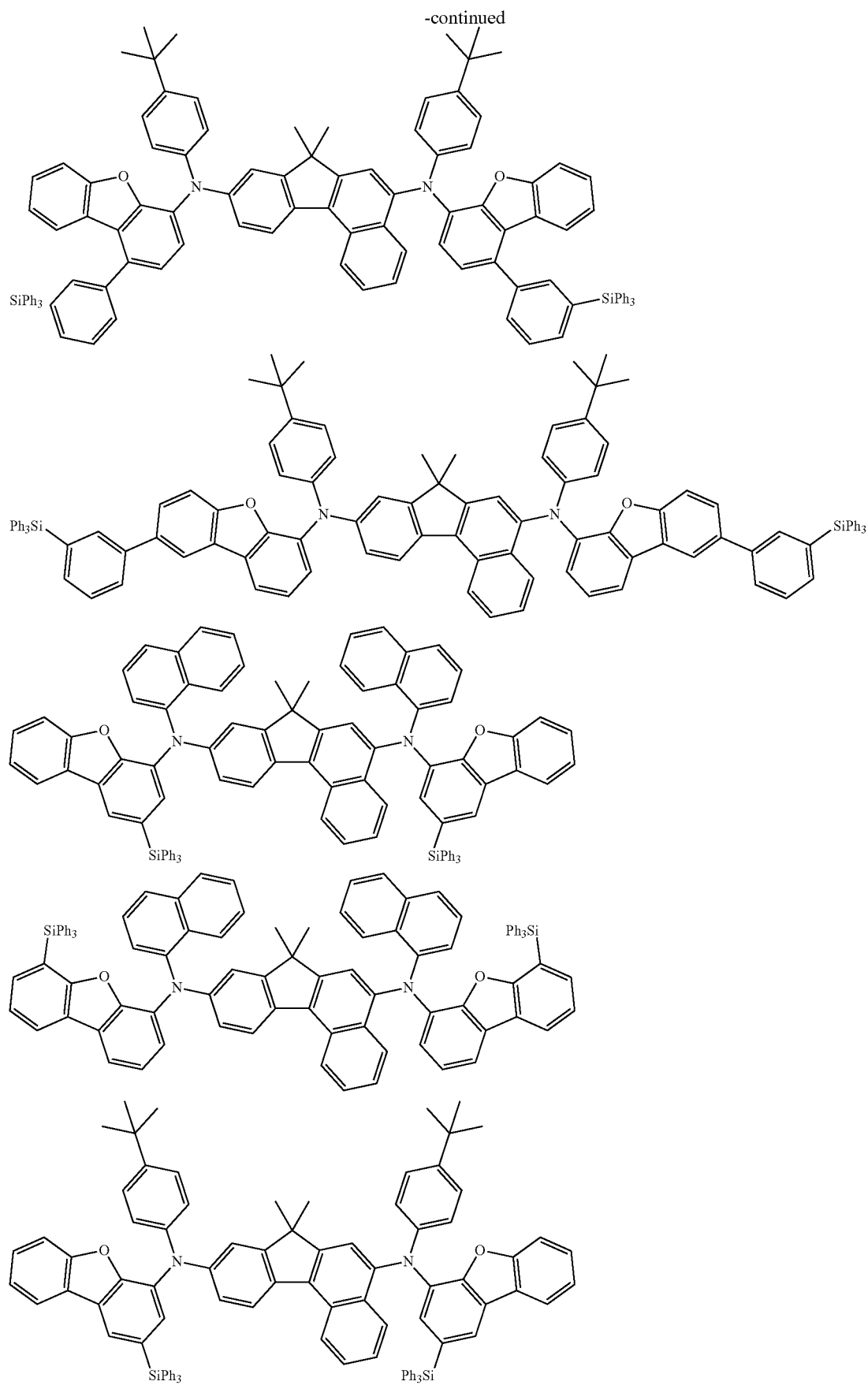

-continued
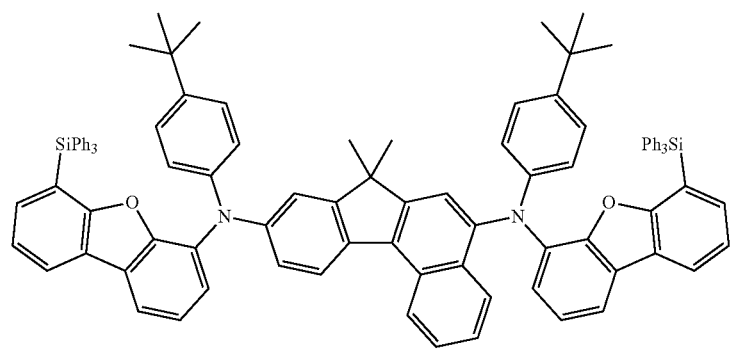
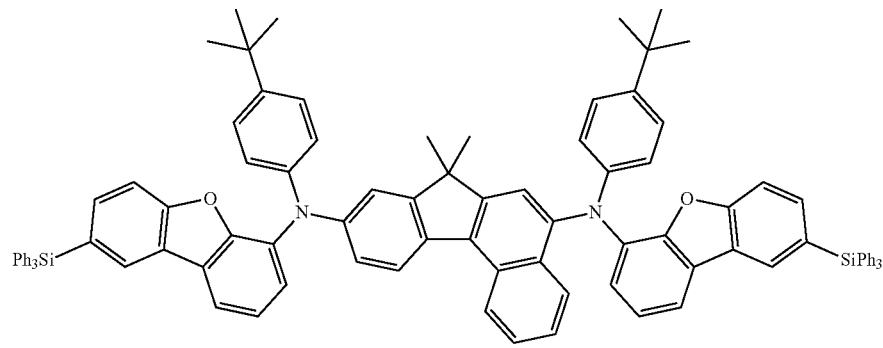
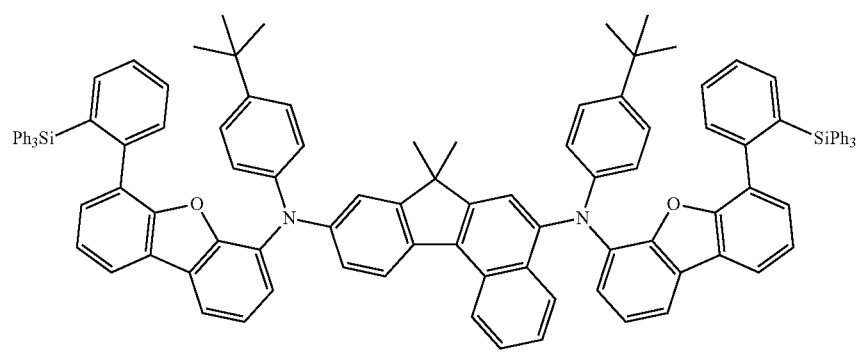
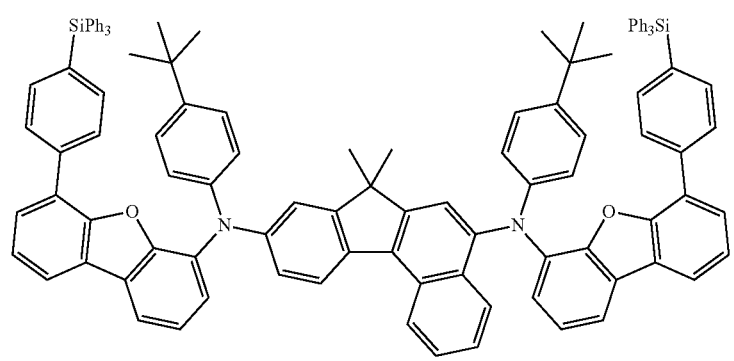

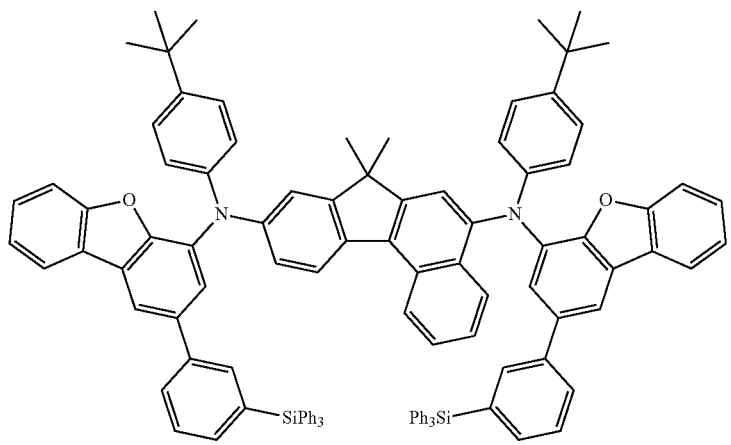
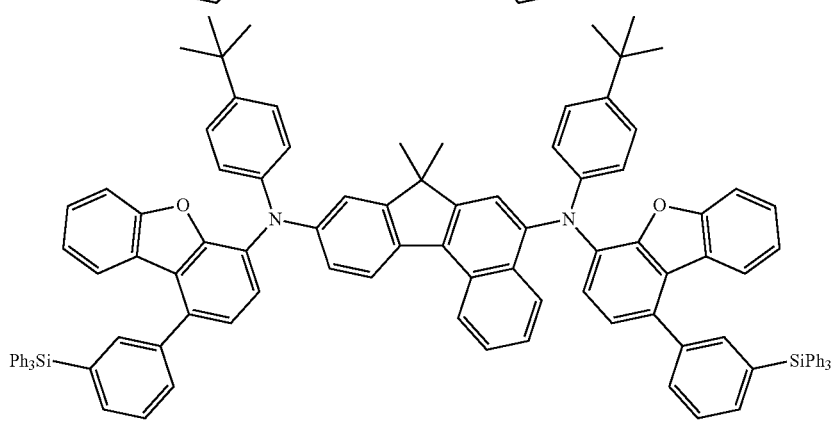
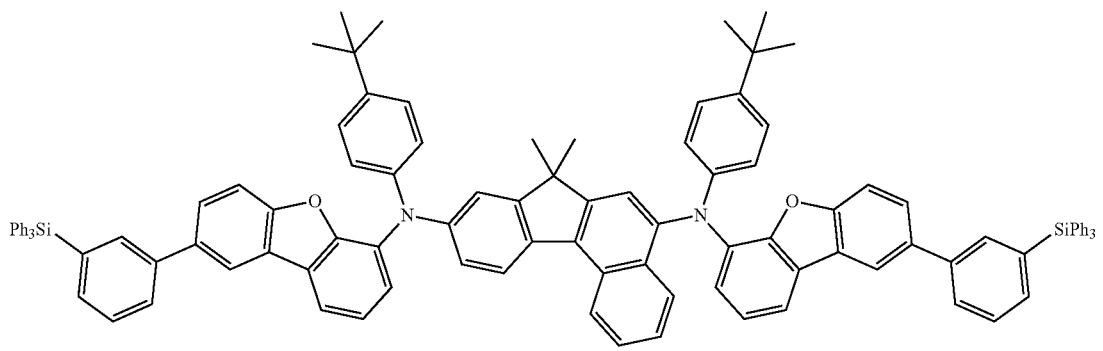
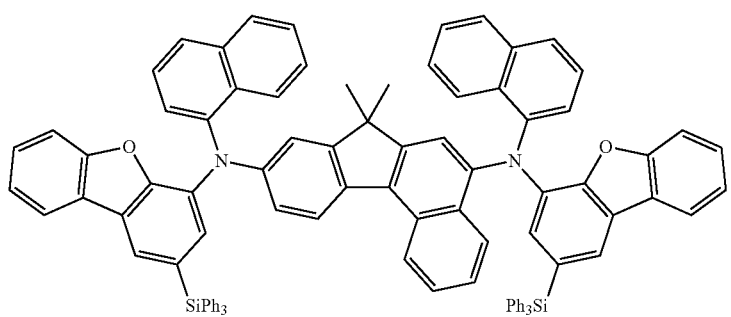

-continued
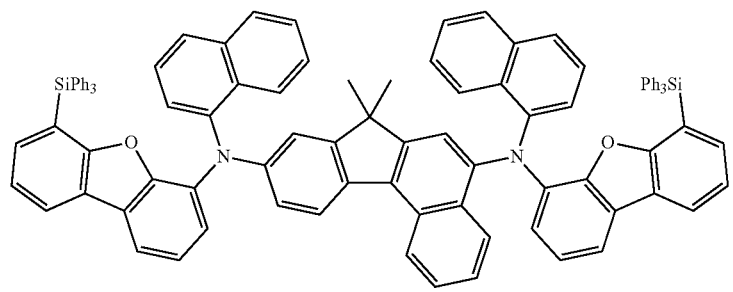
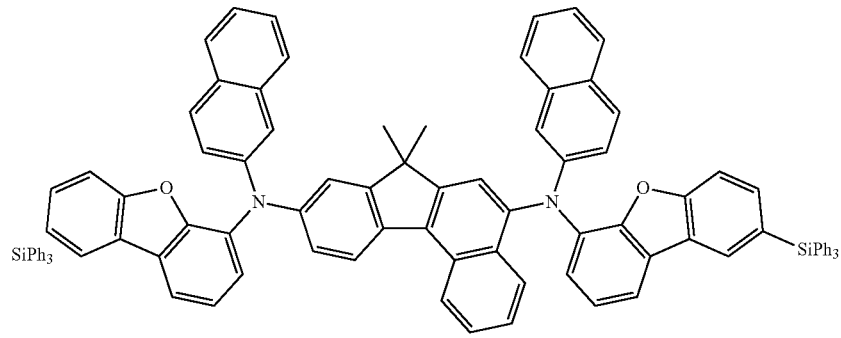
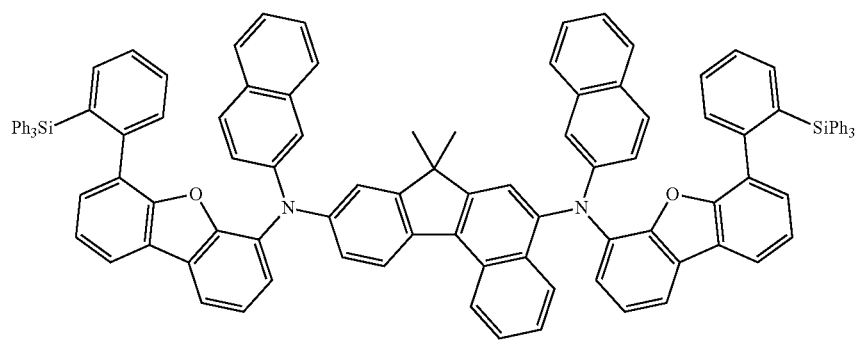
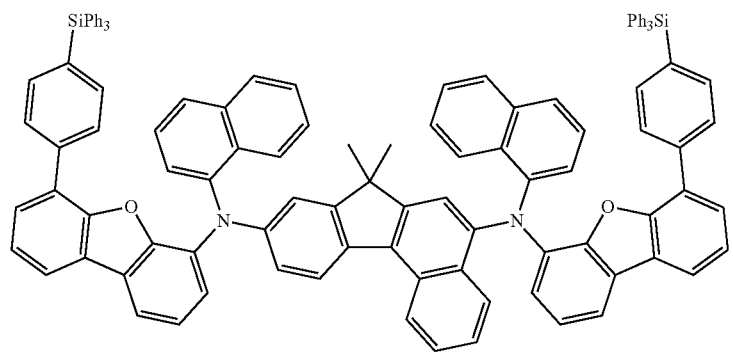
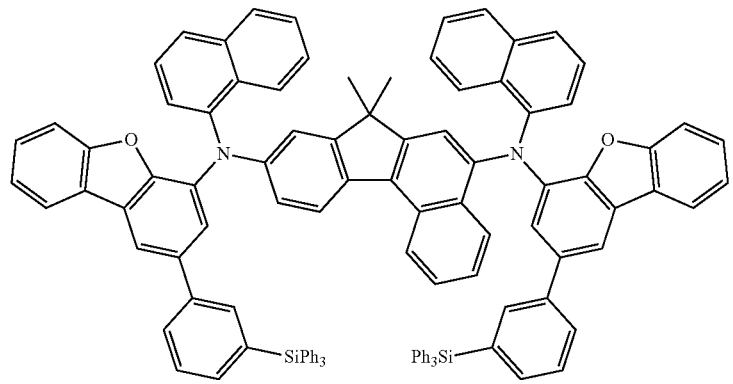

-continued
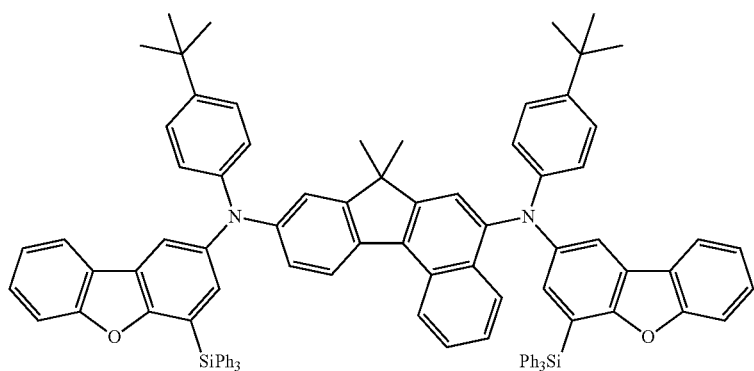
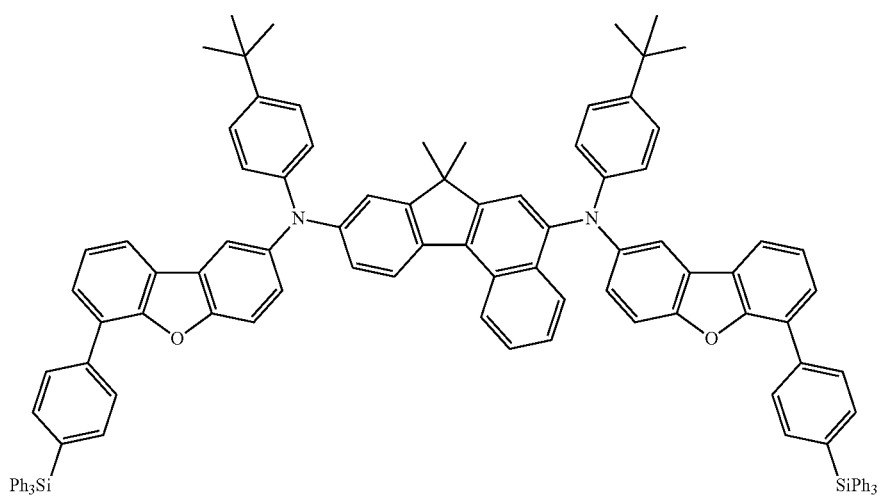
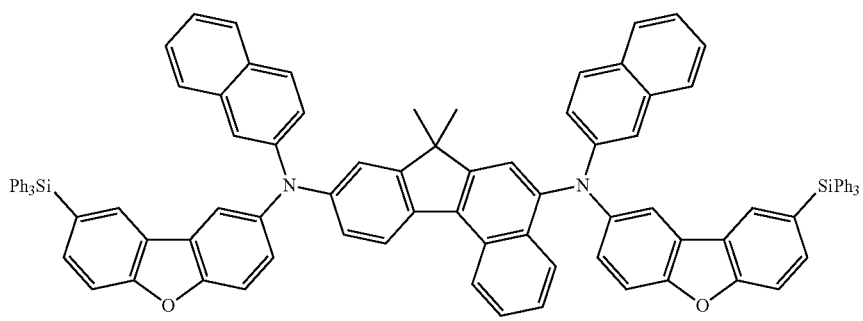
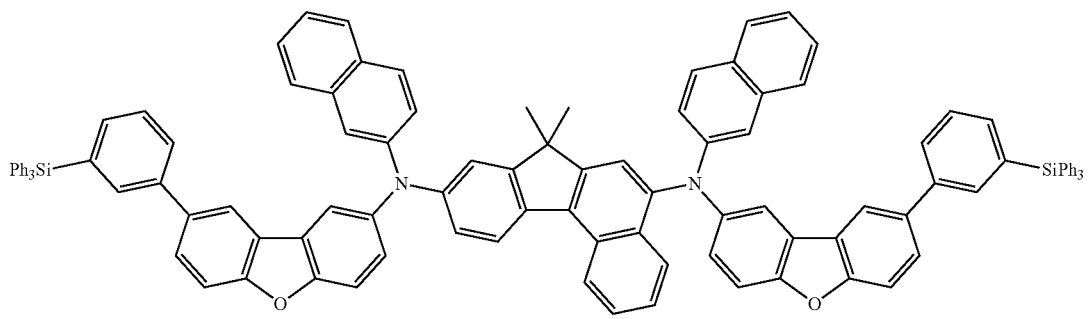

-continued
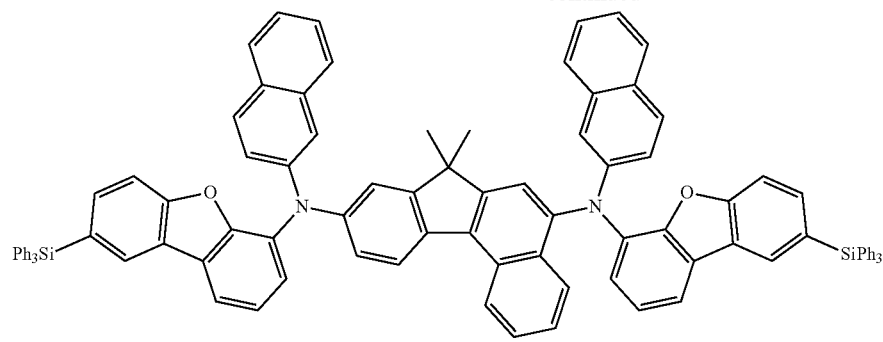
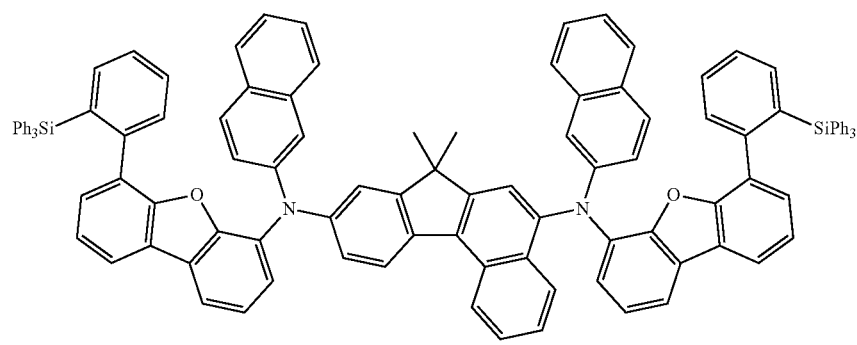
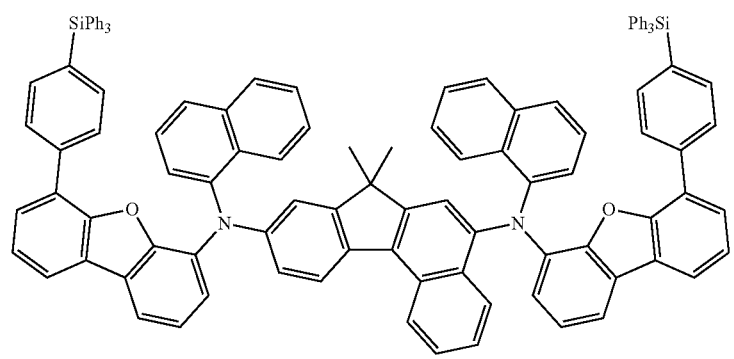
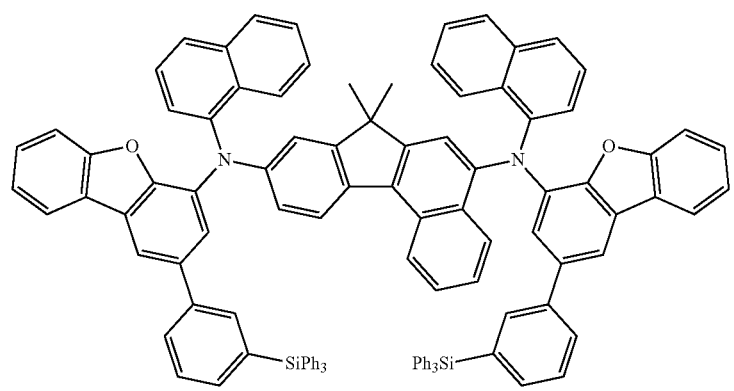

-continued
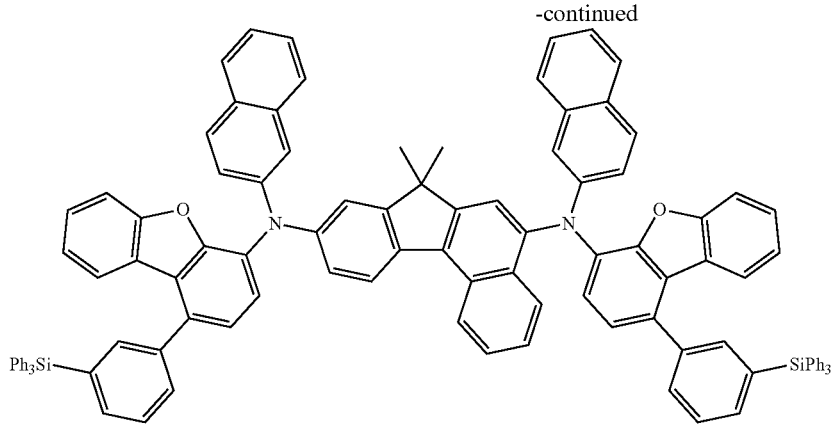
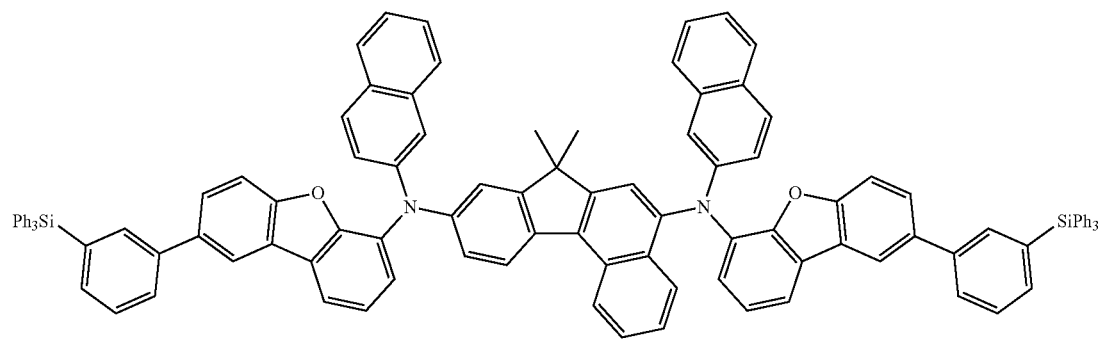
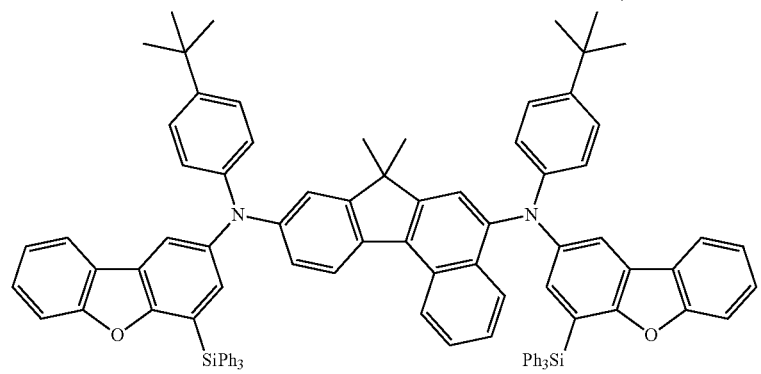
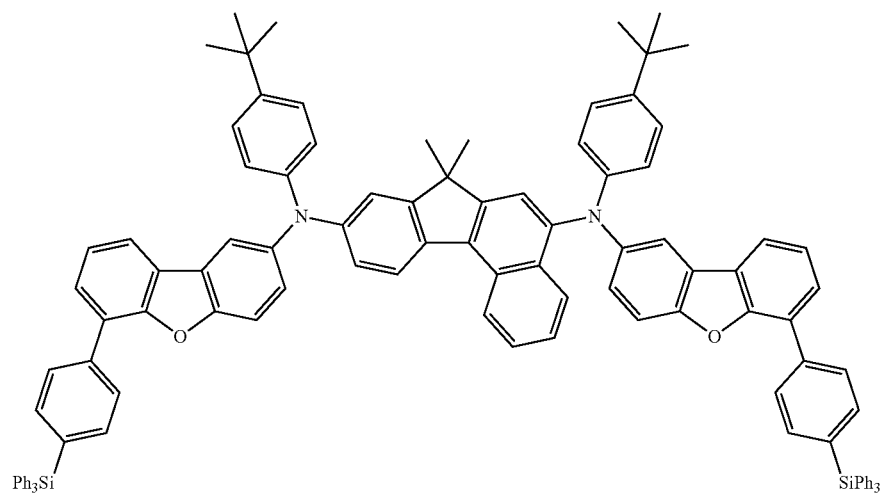

-continued
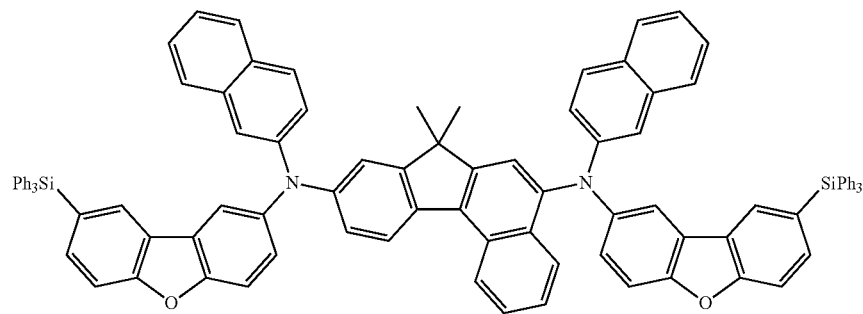
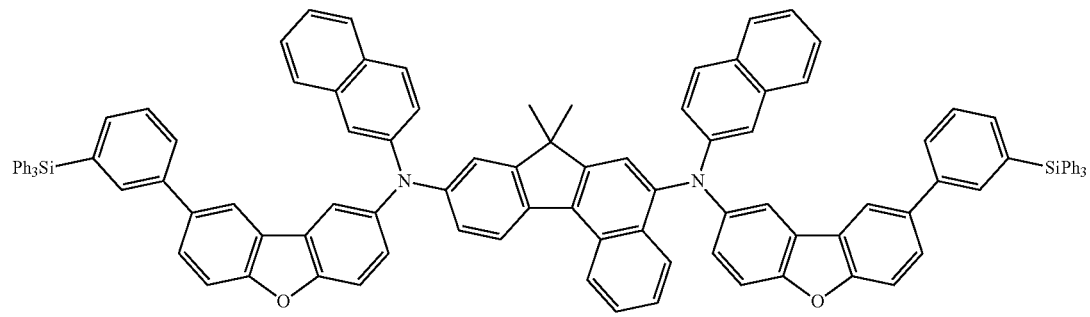
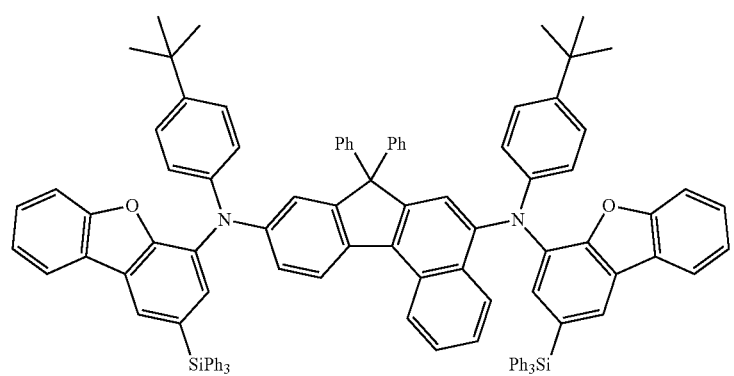
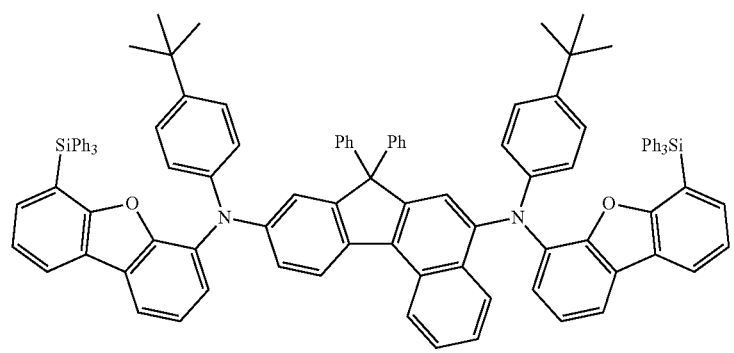
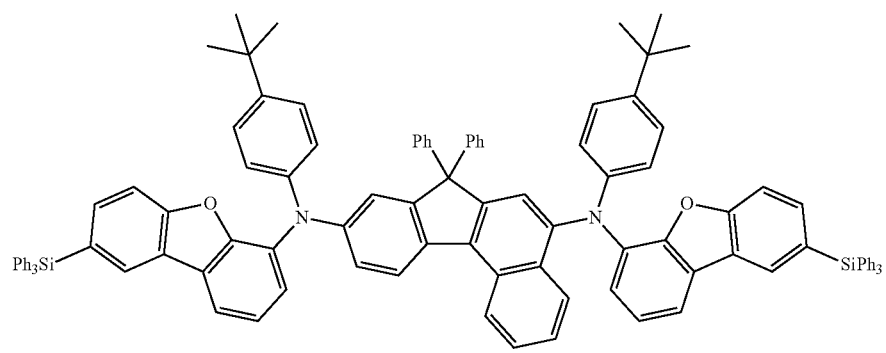

-continued
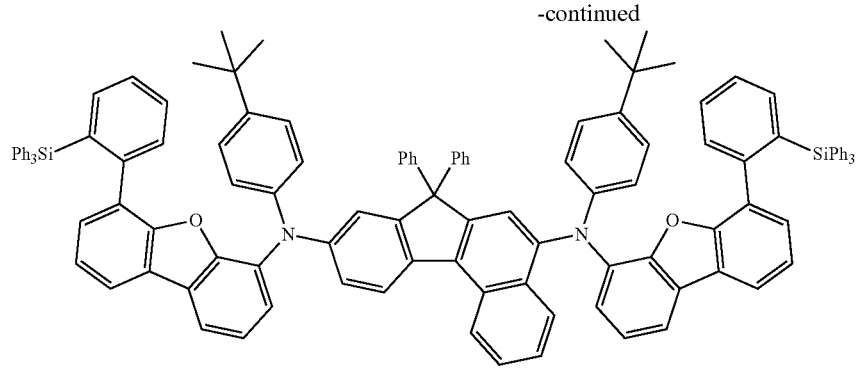
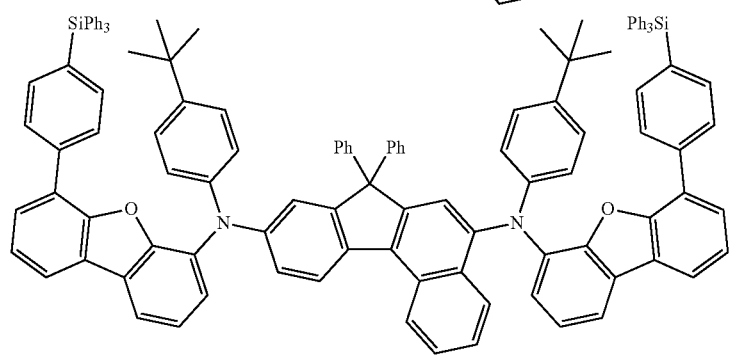
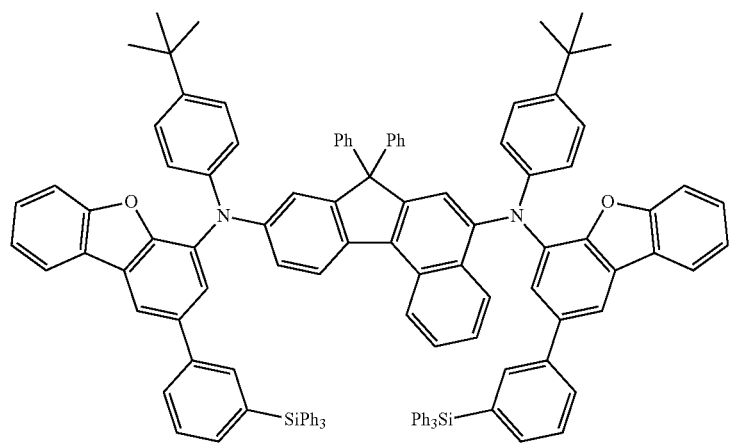
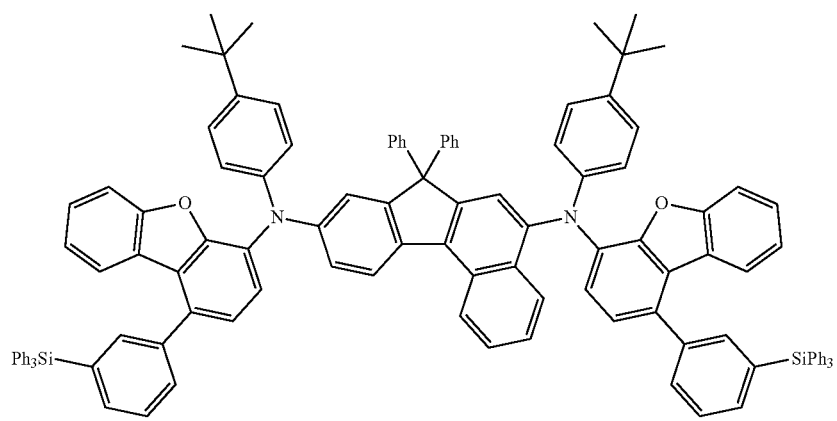

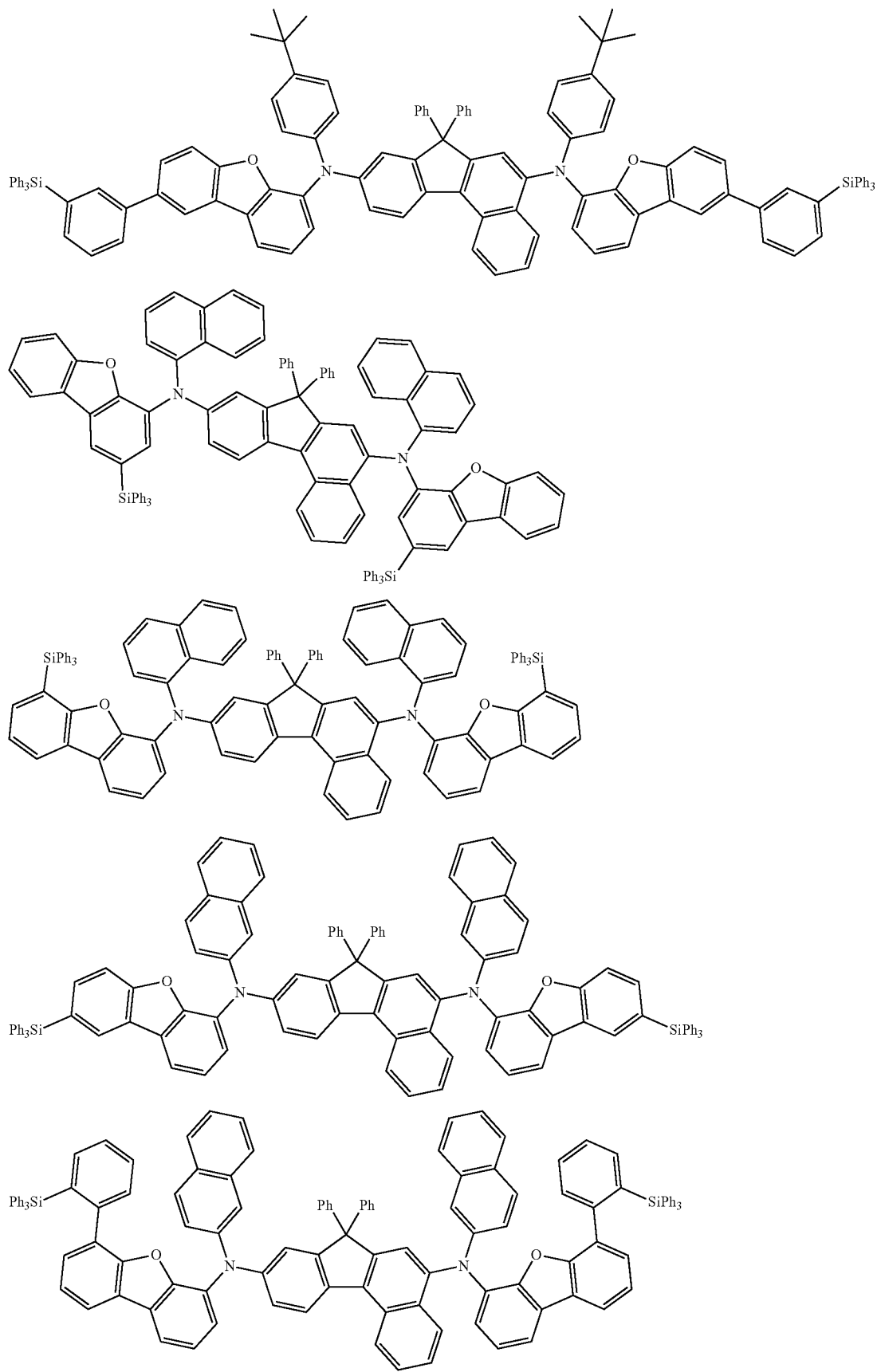

-continued
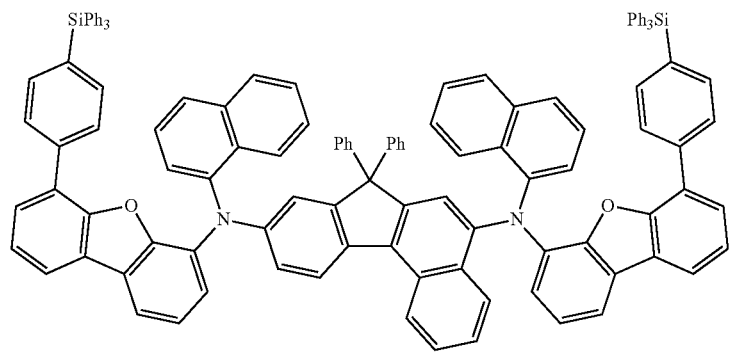
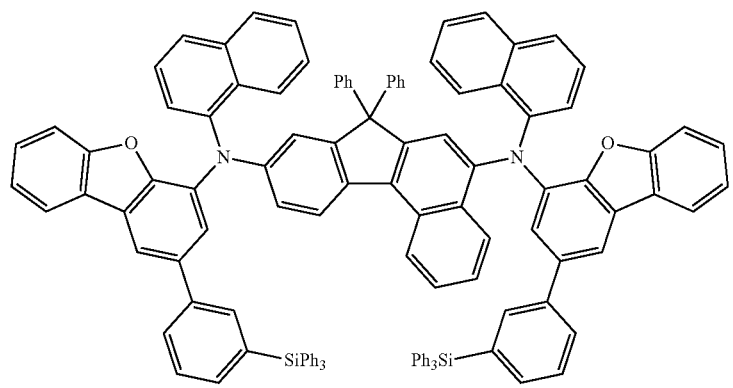
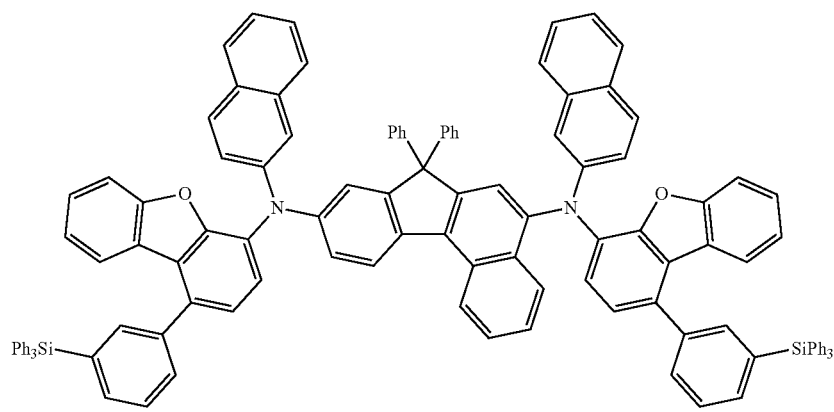
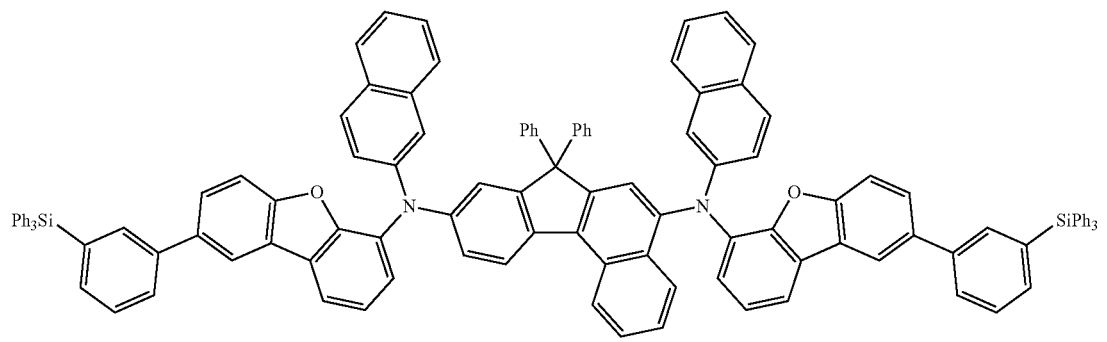

-continued
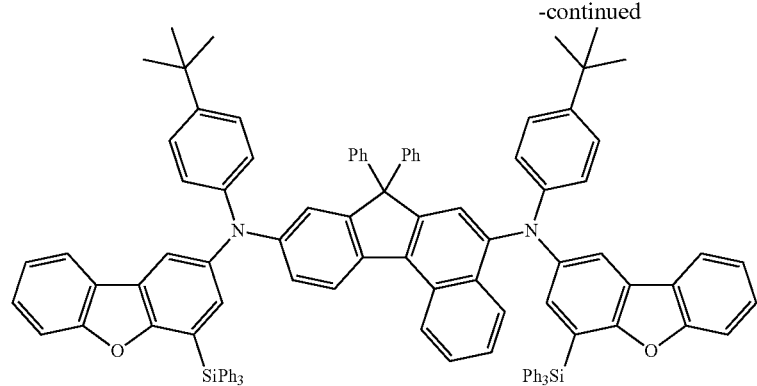
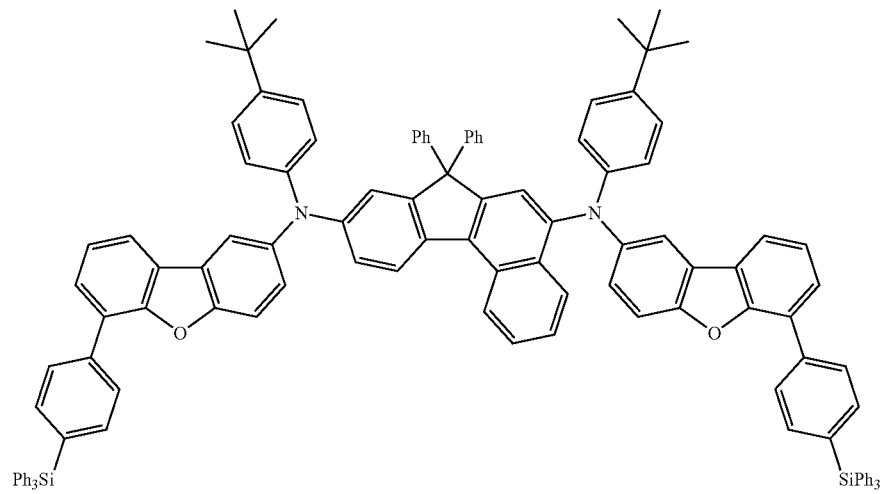
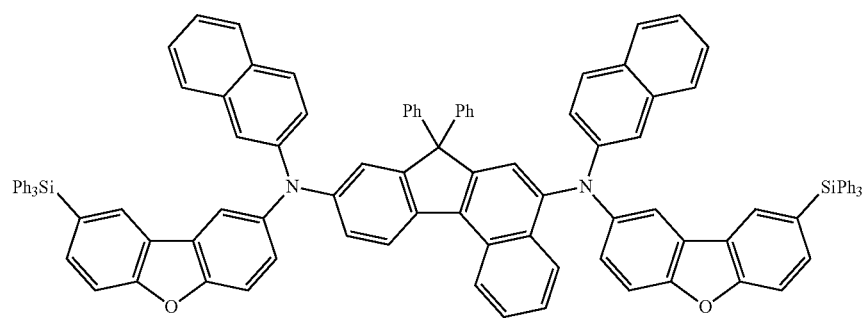
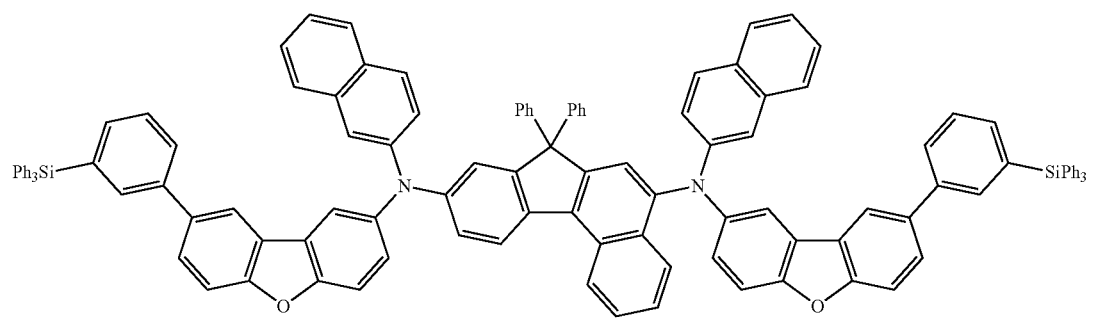

-continued
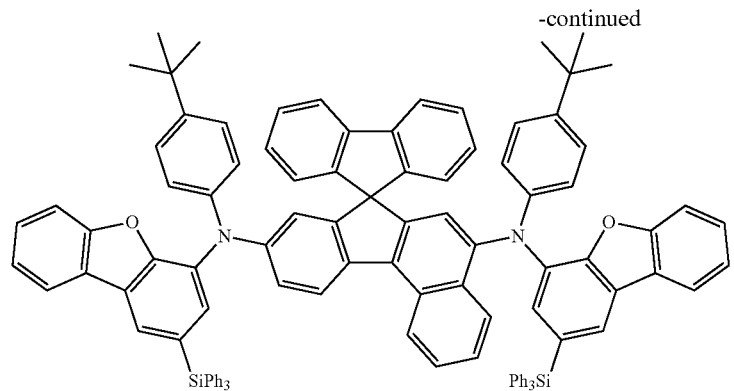
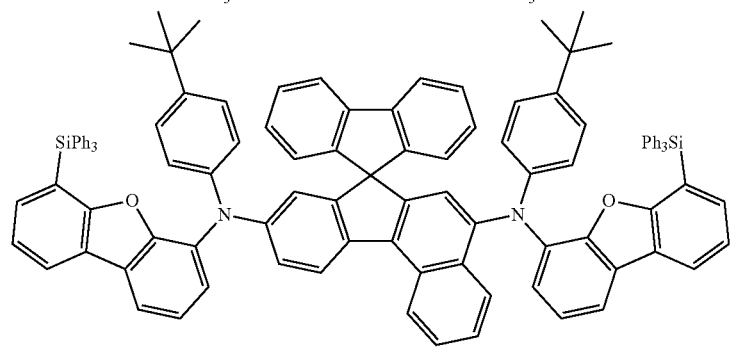
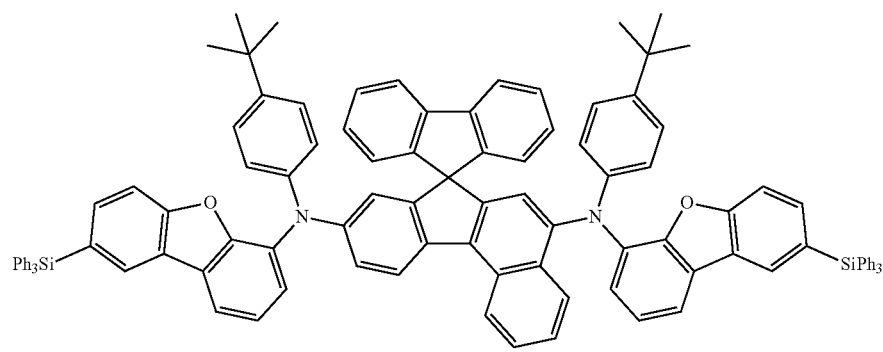
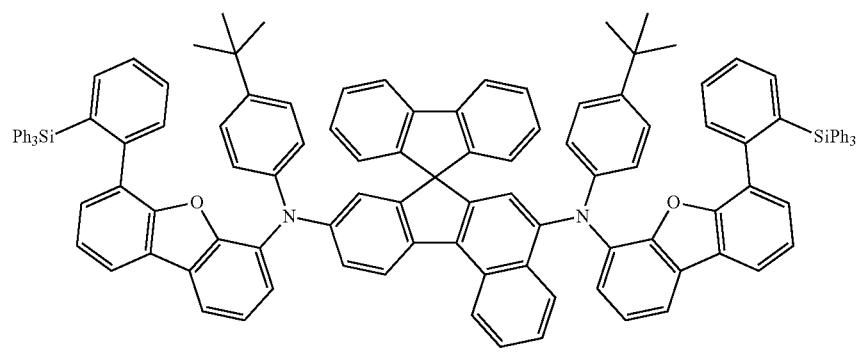

-continued
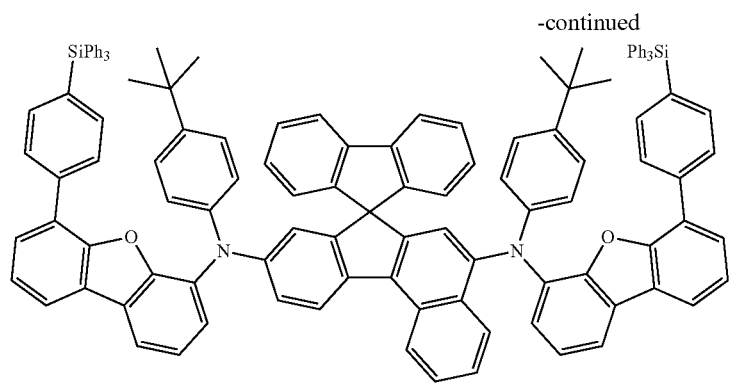
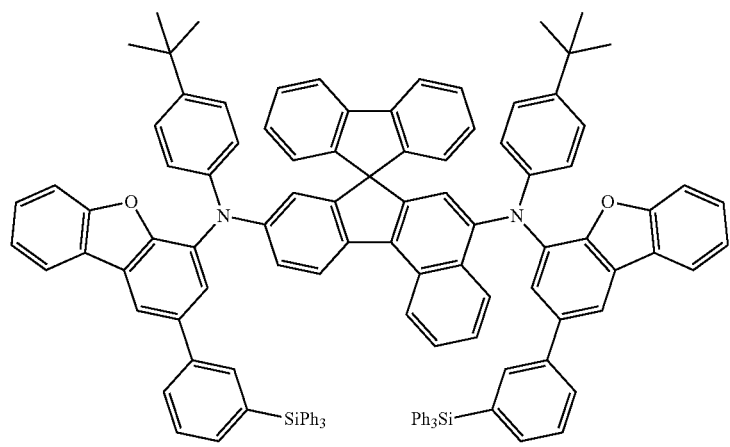
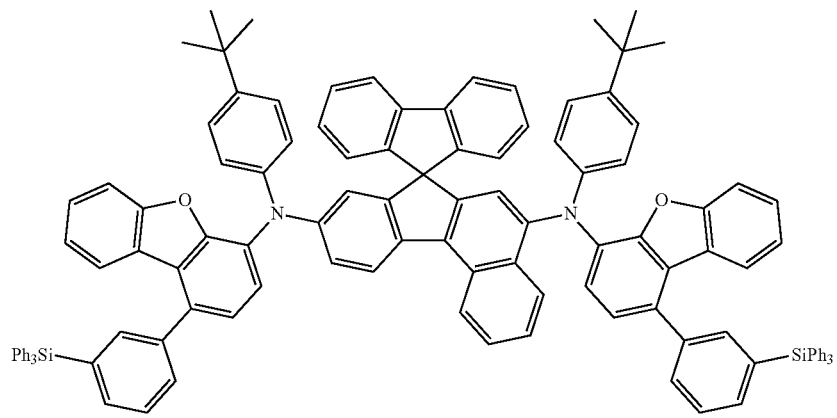
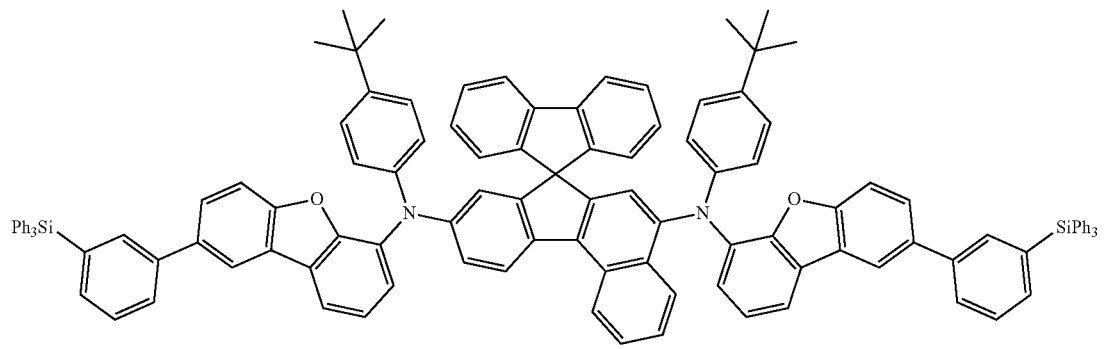

-continued
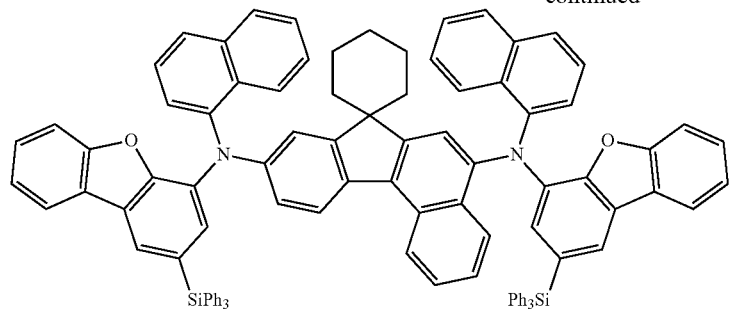
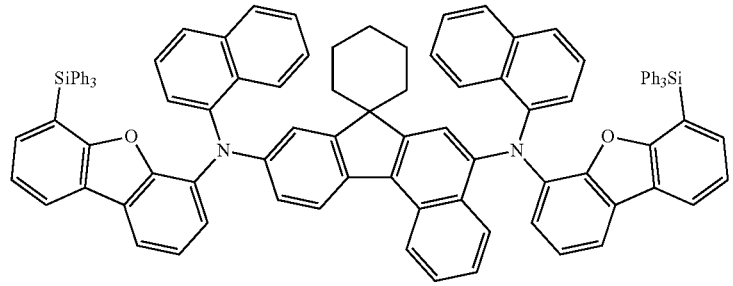
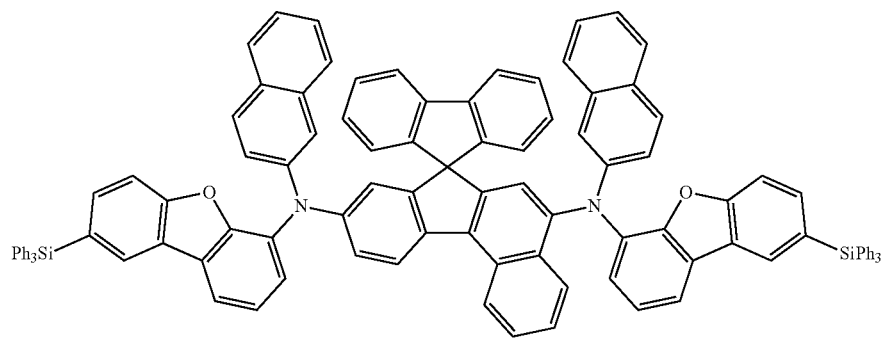
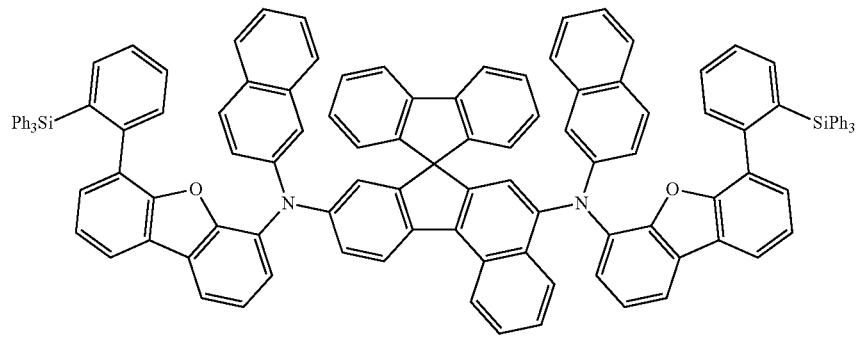
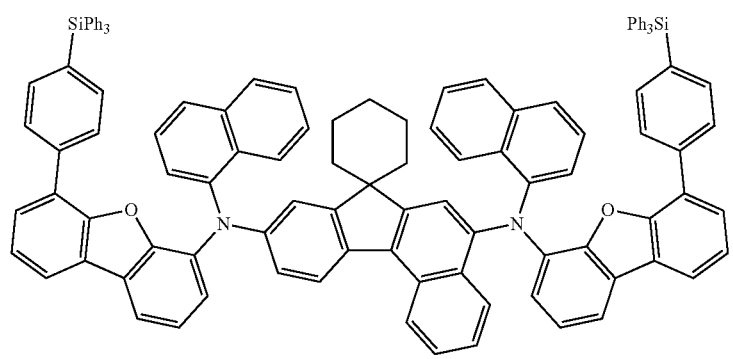

-continued
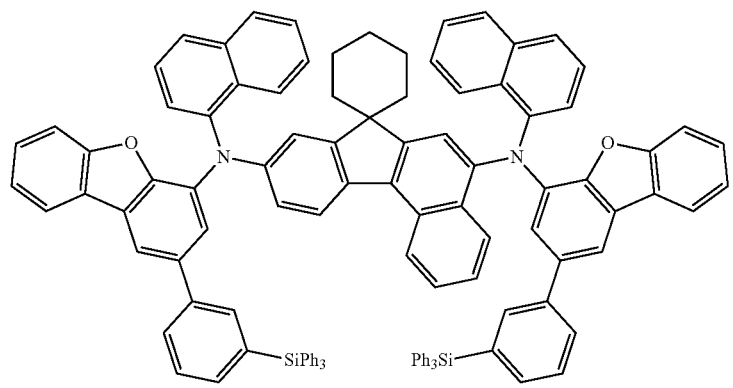
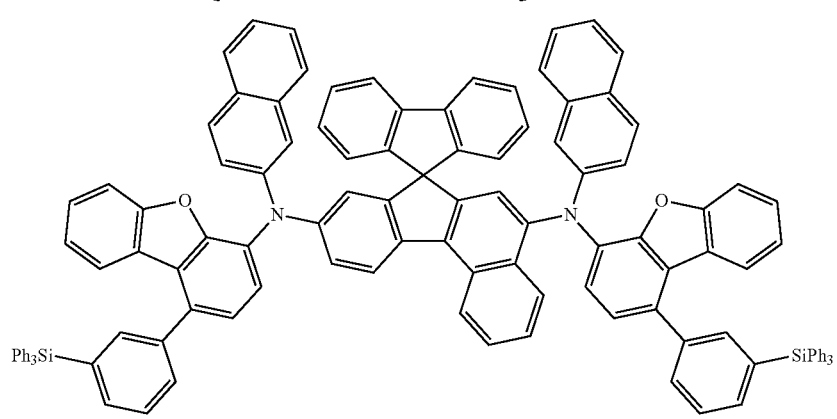
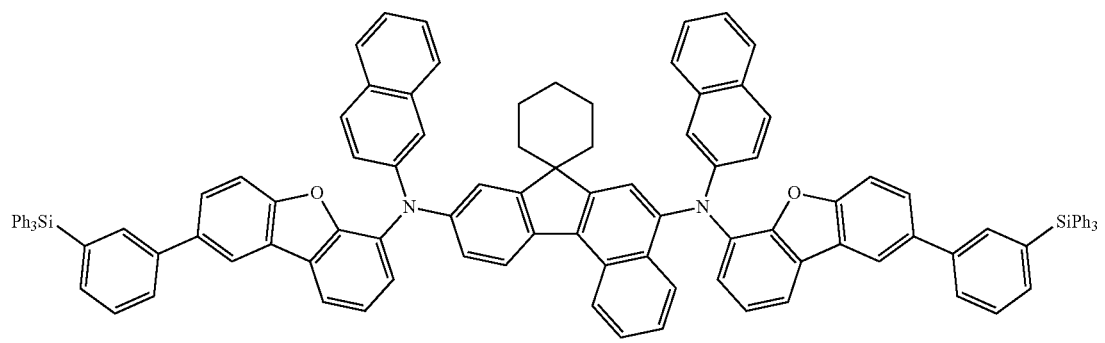
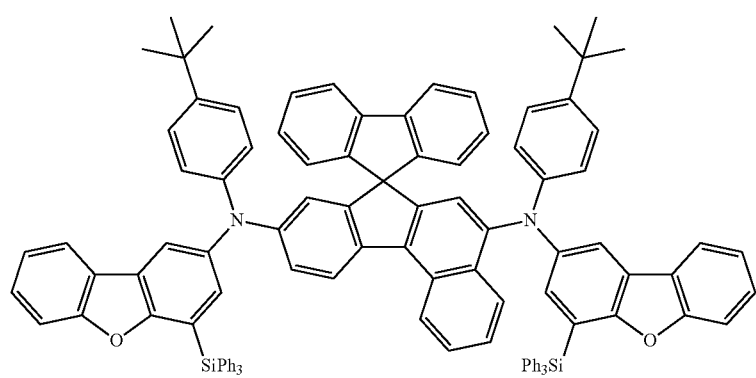

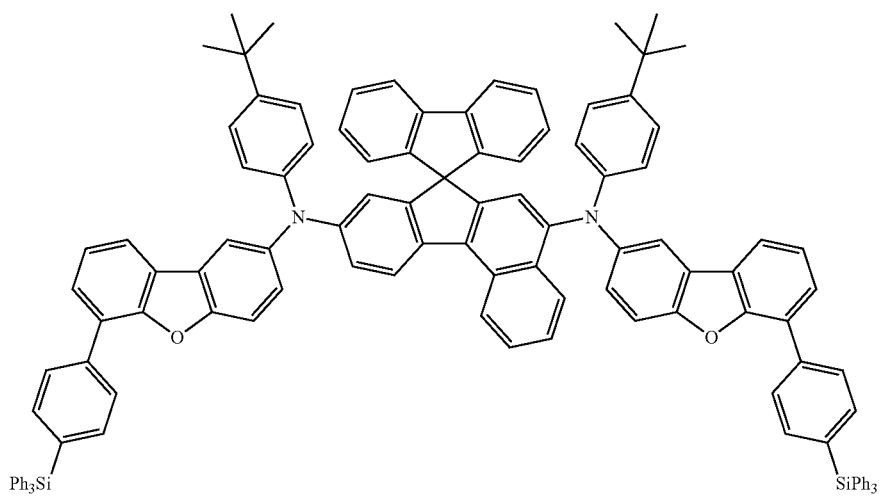
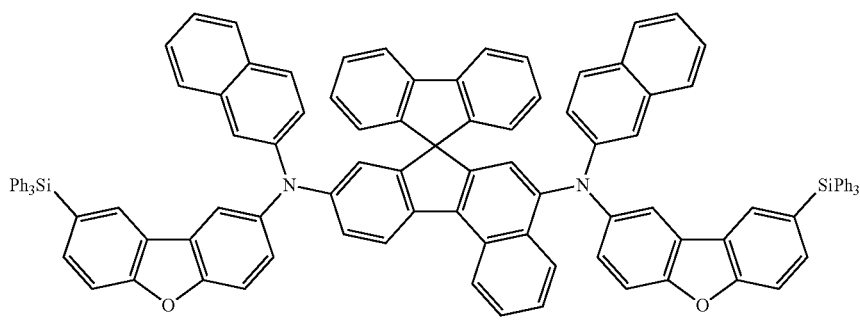
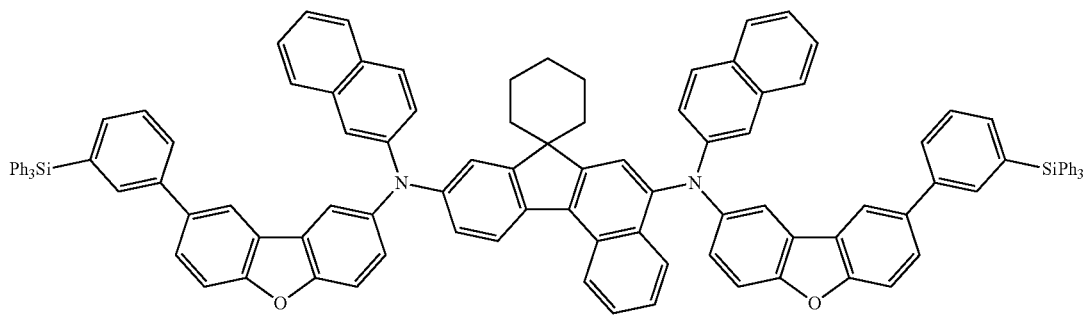
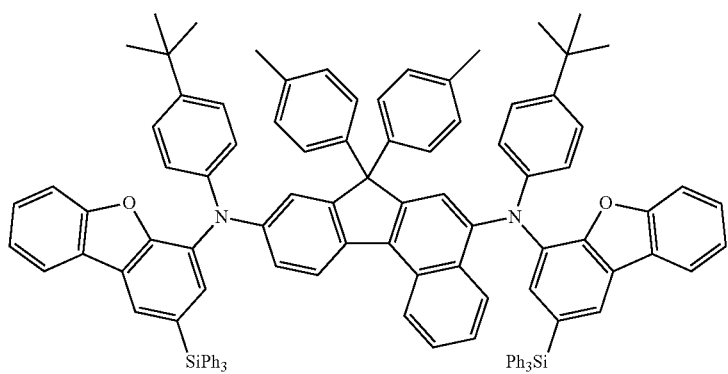

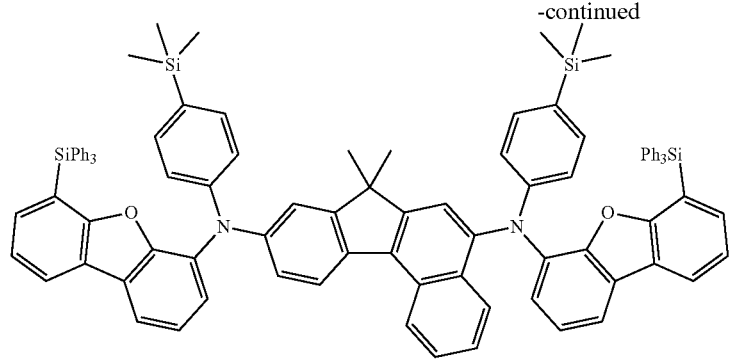
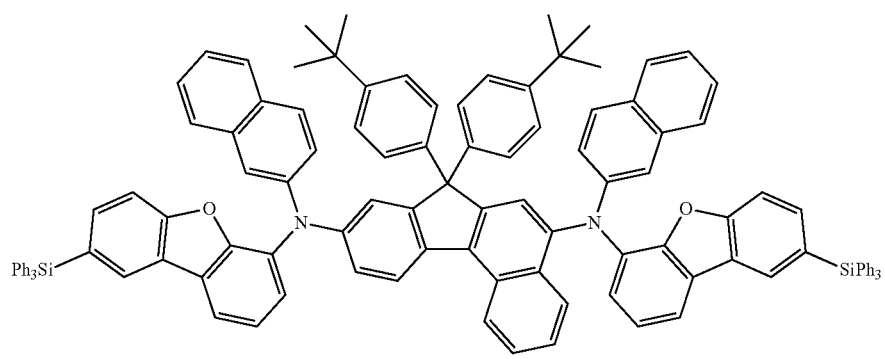
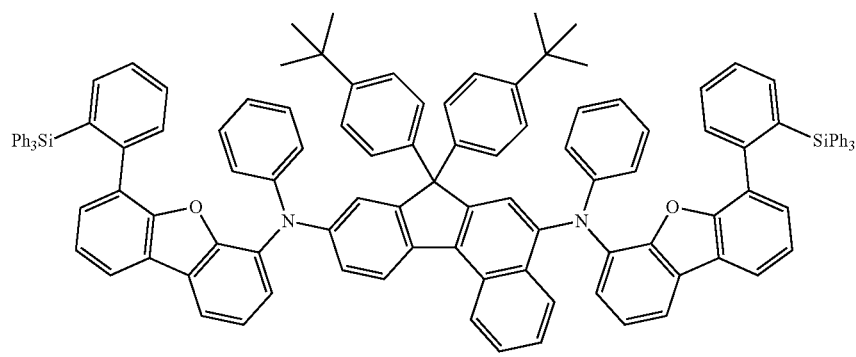
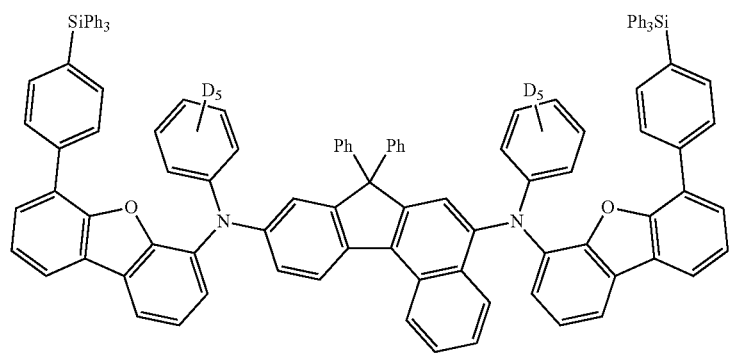

-continued
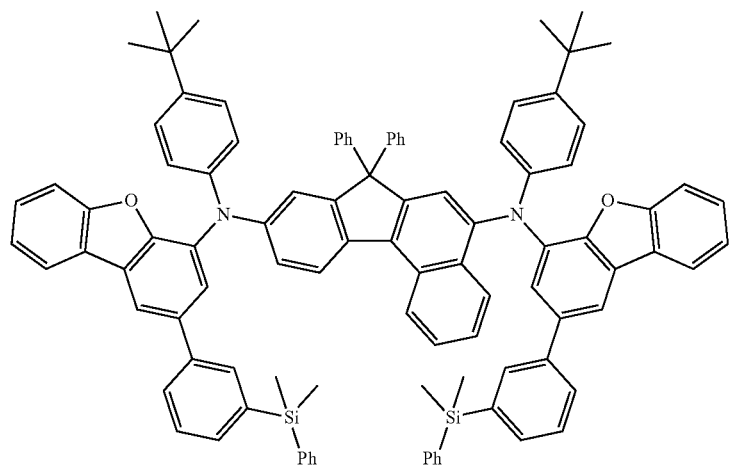
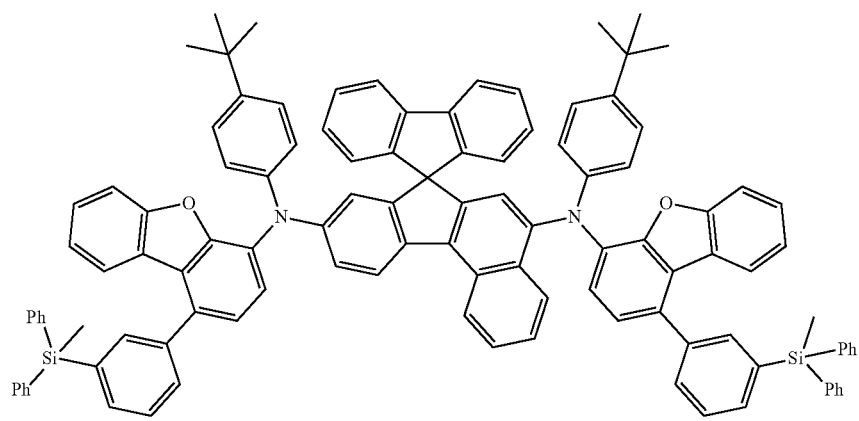
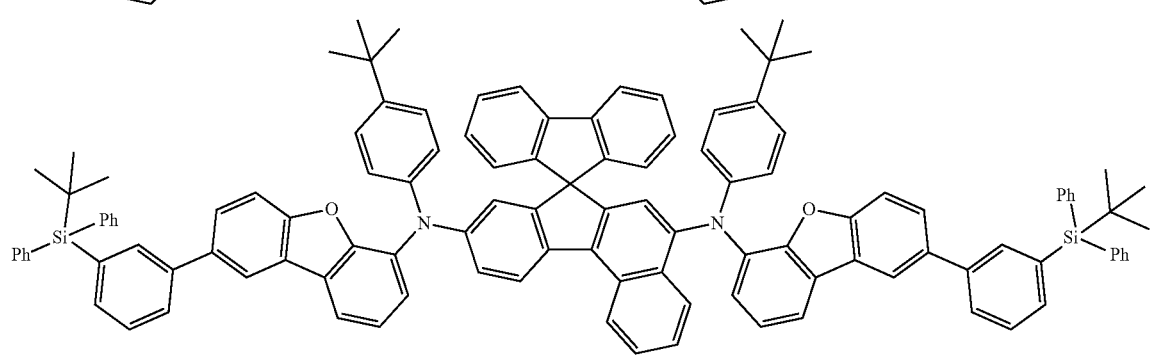
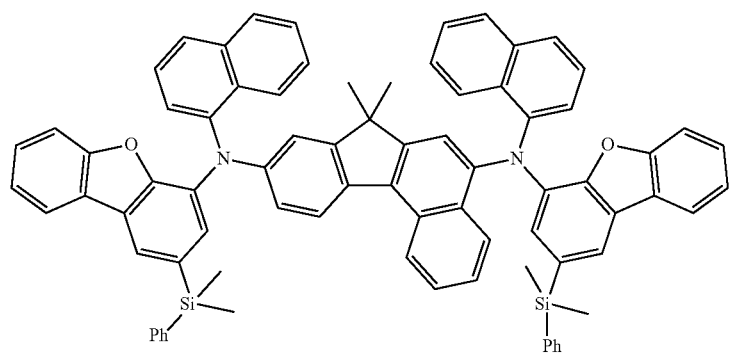

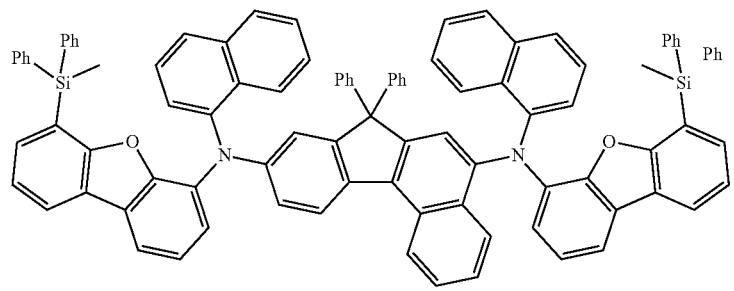
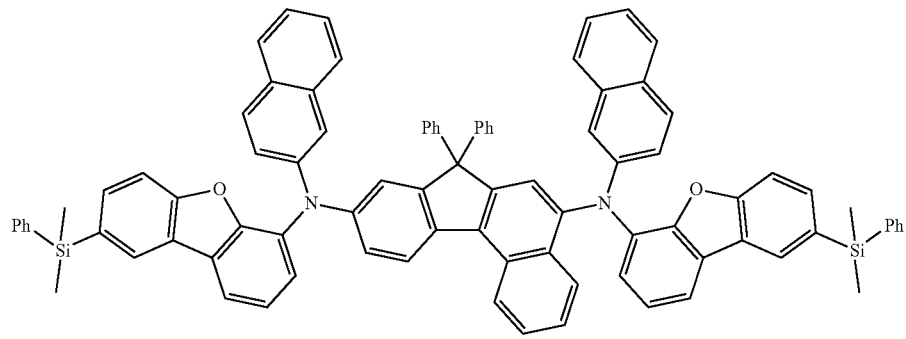
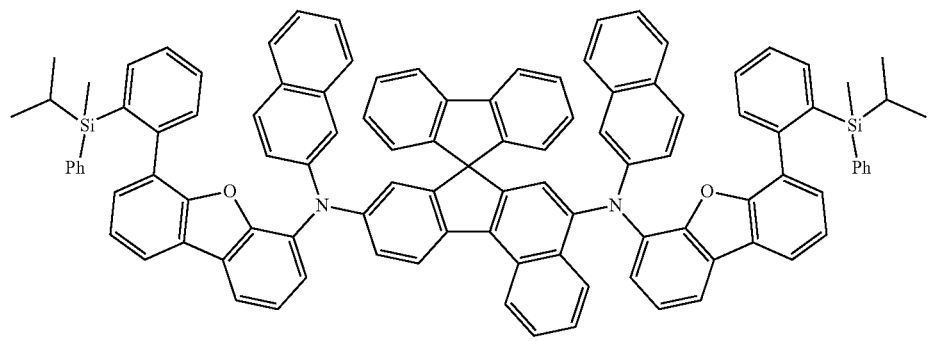
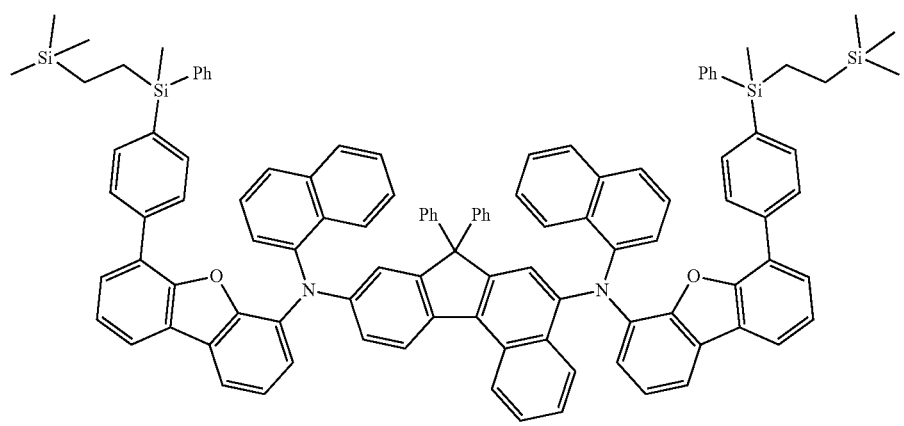

-continued
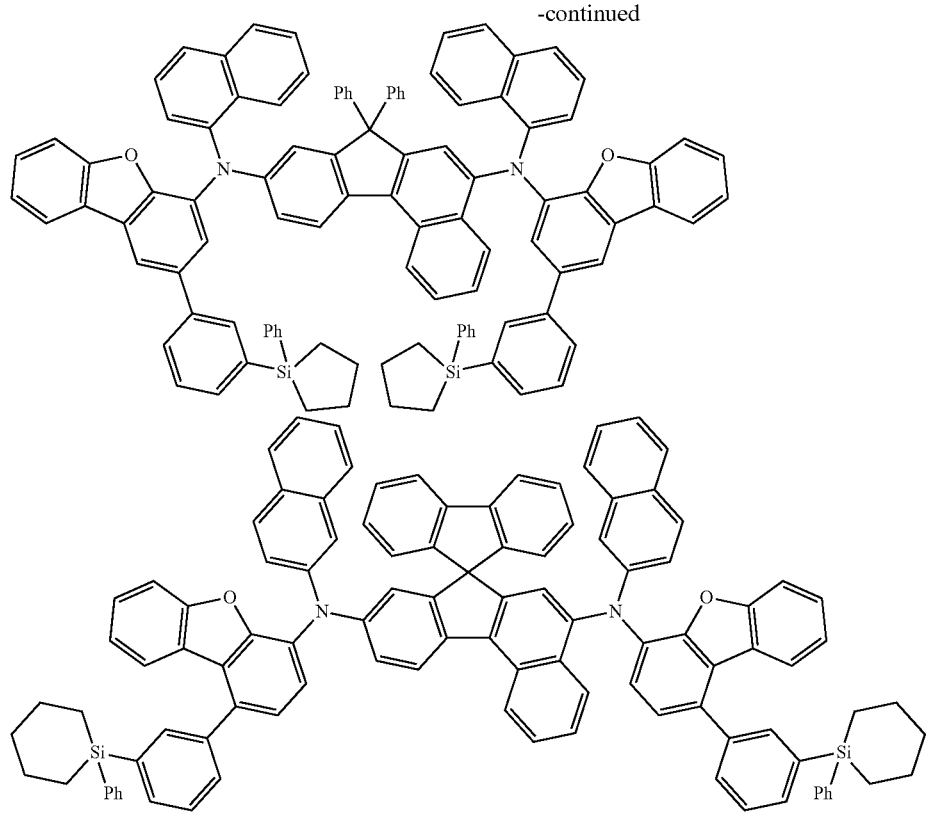
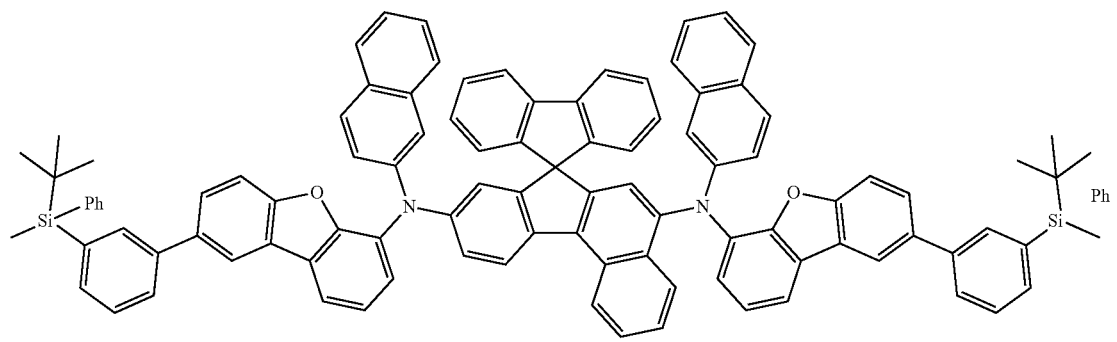
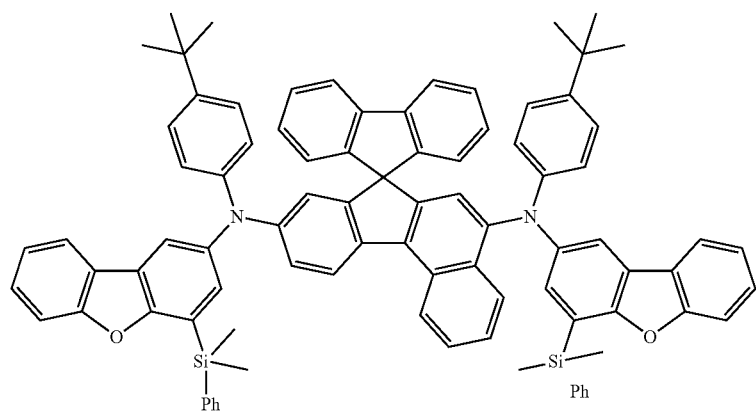

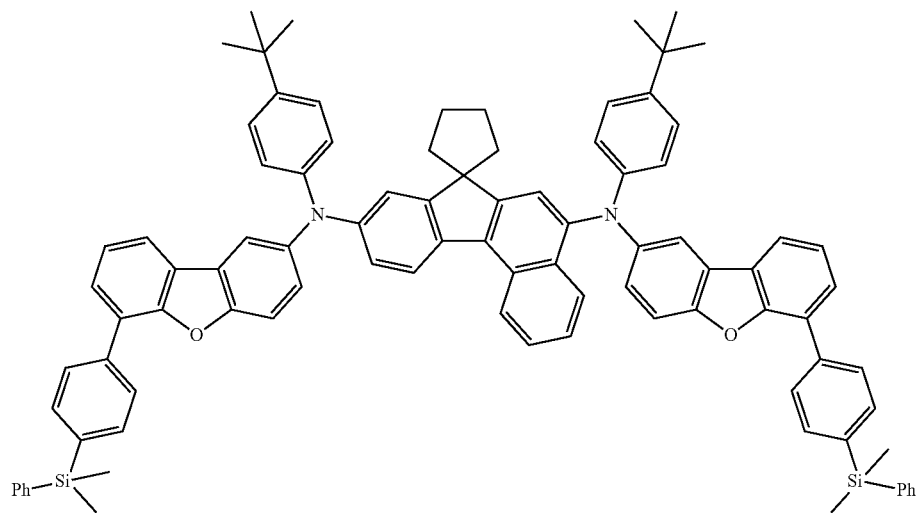
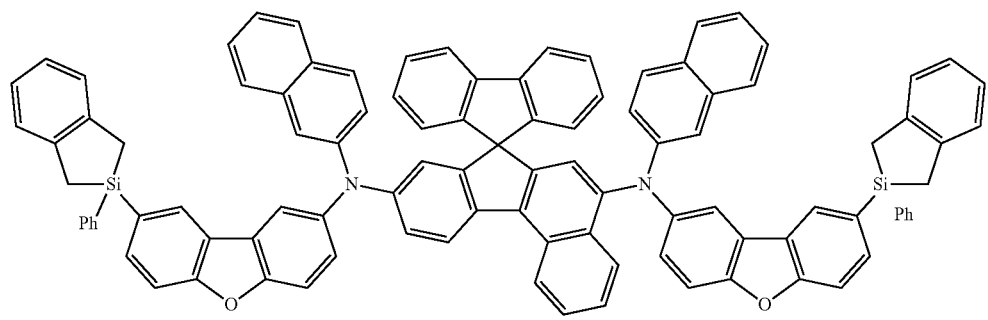
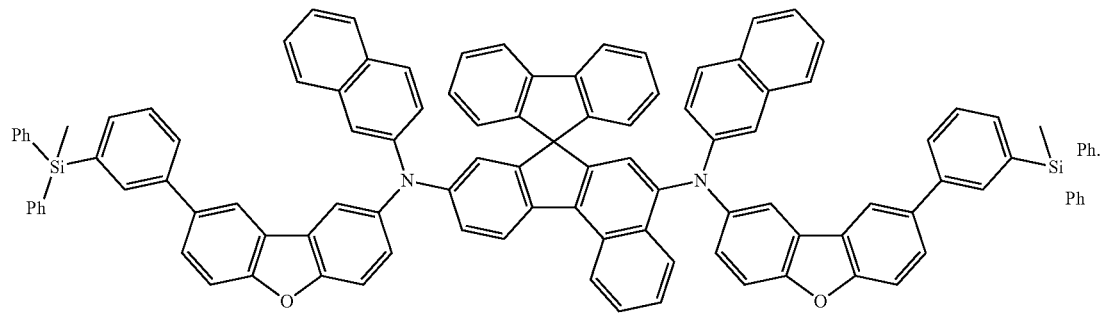

10. An organic light emitting device comprising a first electrode; a second electrode opposite to the first electrode; and one or more organic material layers between the first electrode and the second electrode, wherein the one or more organic material layers comprise the compound according to claim 1.

11. The organic light emitting device according to claim 10, wherein the one or more organic material layers comprise a light emission layer, and the light emission layer comprises the compound.

12. The organic light emitting device according to claim 11, wherein the light emission layer further comprises a compound of the following Chemical Formula 3:

[Chemical Formula 3]

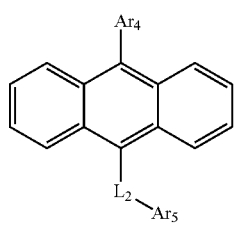

in the Chemical Formula 3, $L_2$ is a single bond; or substituted or unsubstituted $C_{6-60}$ arylene, $Ar_4$ and $Ar_5$ are each independently, substituted or unsubstituted $C_{6-60}$ aryl; or substituted or unsubstituted $C_{5-60}$ heteroaryl comprising one or more heteroatoms selected from the group consisting of N, O and S.

13. The organic light emitting device according to claim 12, wherein $L_2$ is a single bond; or phenylene.

14. The organic light emitting device according to claim 12, wherein $Ar_4$ and $Ar_5$ are each independently, one selected from the group consisting of the followings:

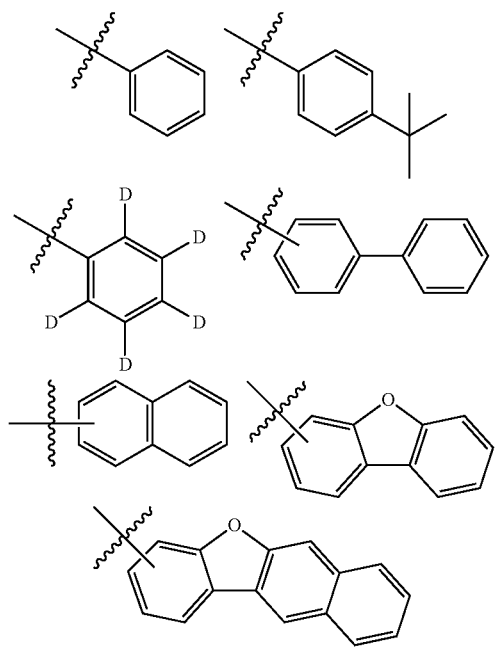

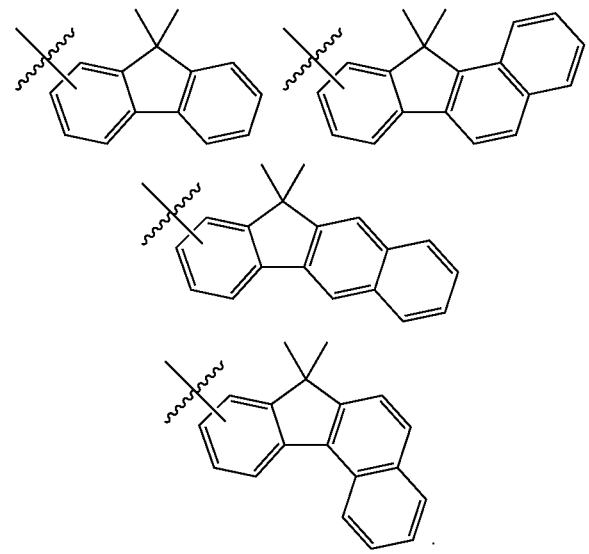

15. The organic light emitting device according to claim 12, wherein the compound represented by the Chemical Formula 3 is one selected from the group consisting of the following compounds:

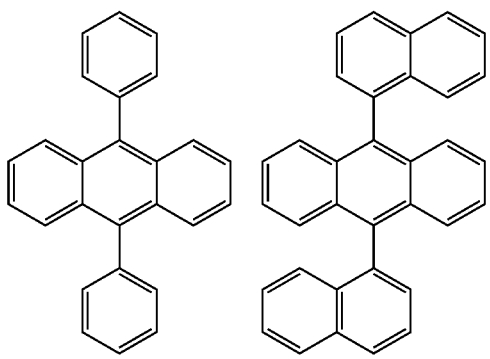

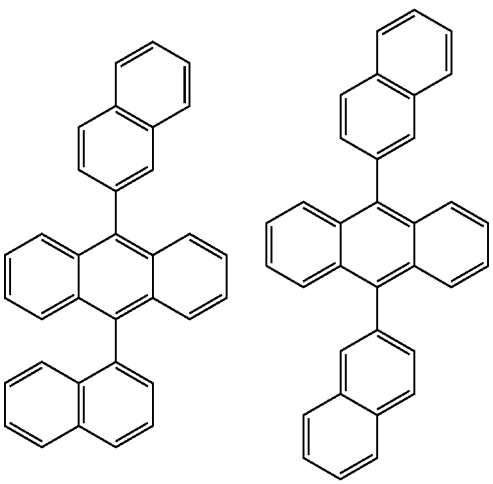

-continued
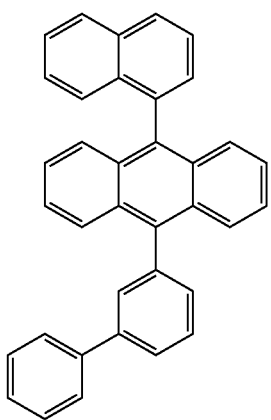
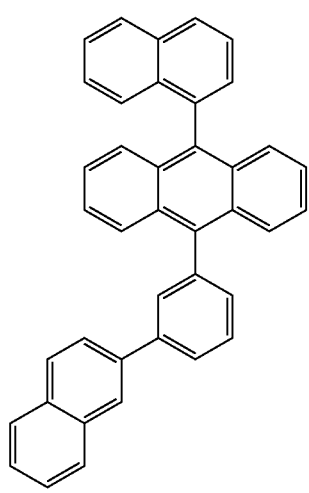
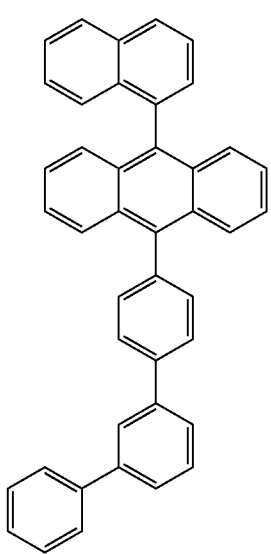
-continued
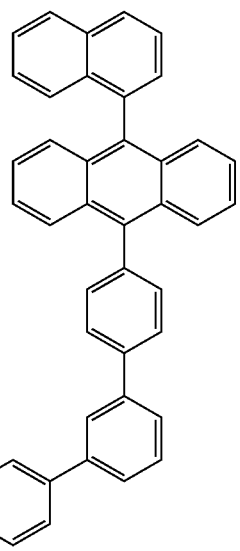
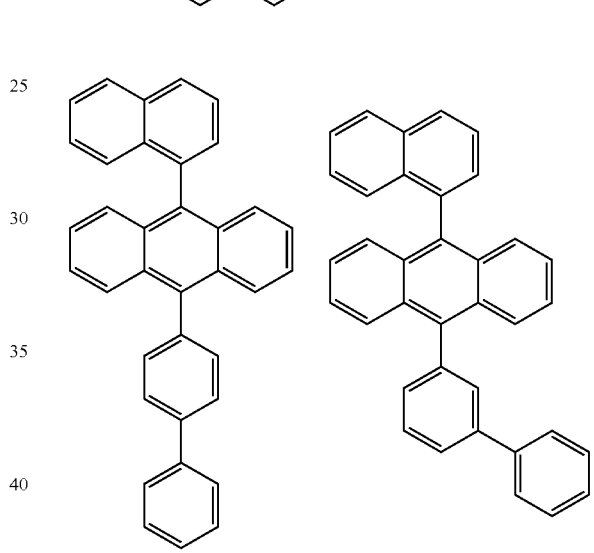
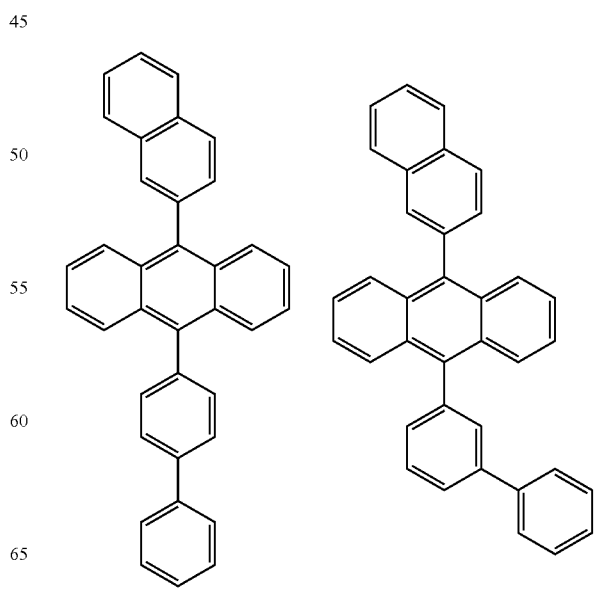

131
-continued
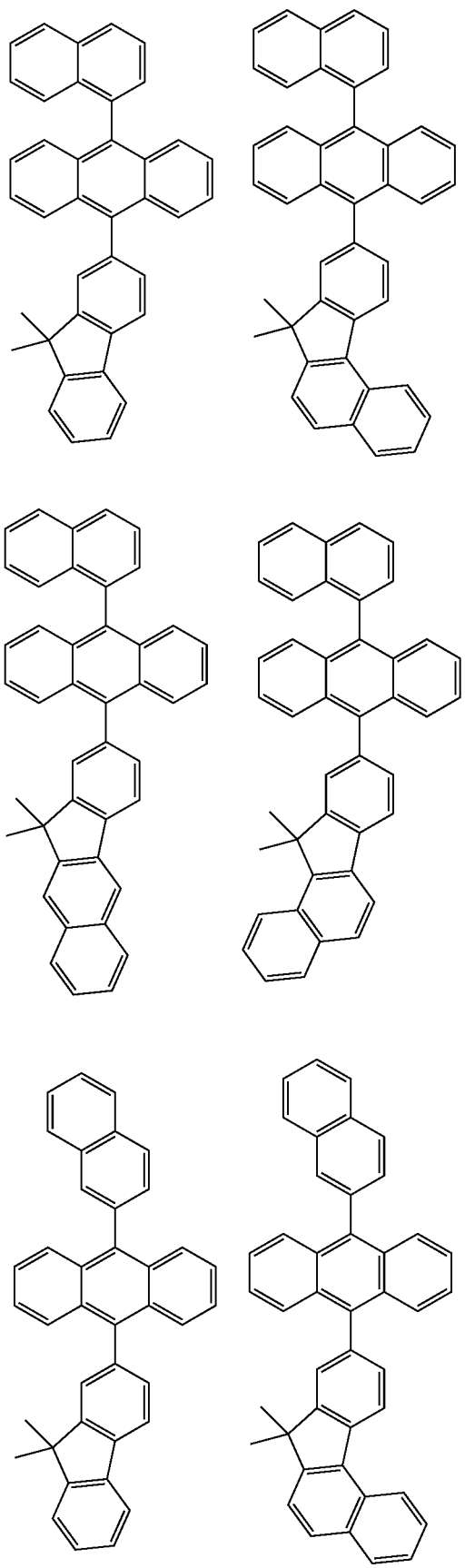
132
-continued
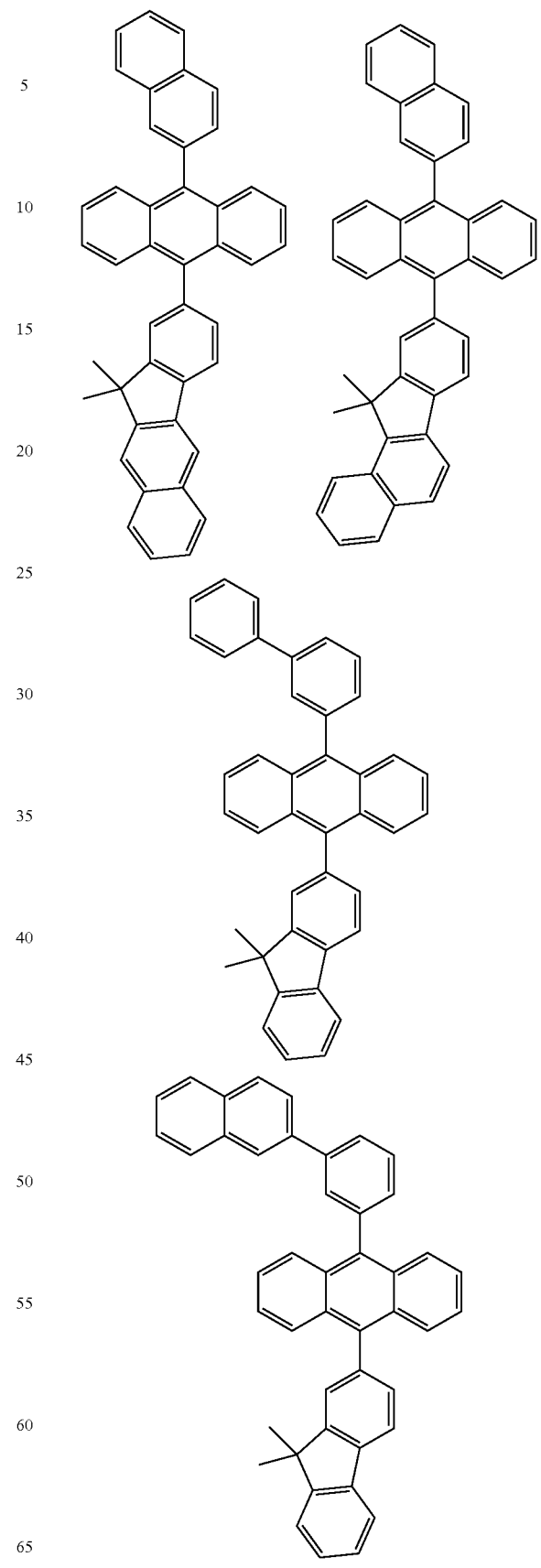

133
-continued
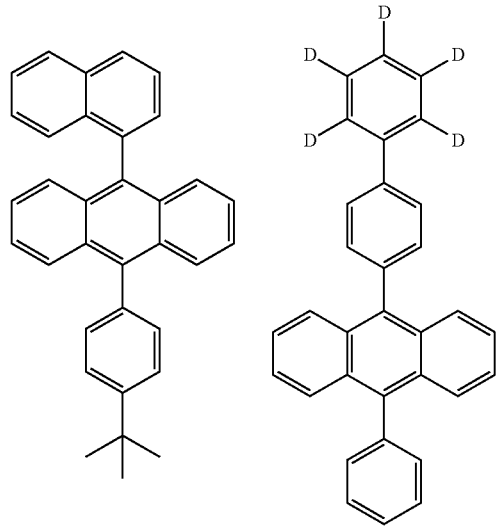
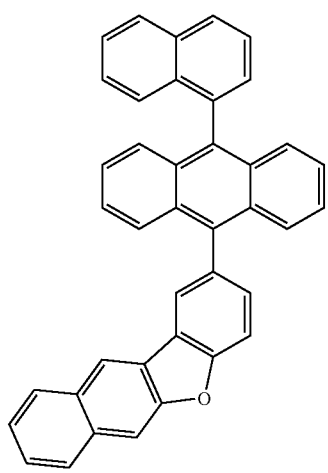
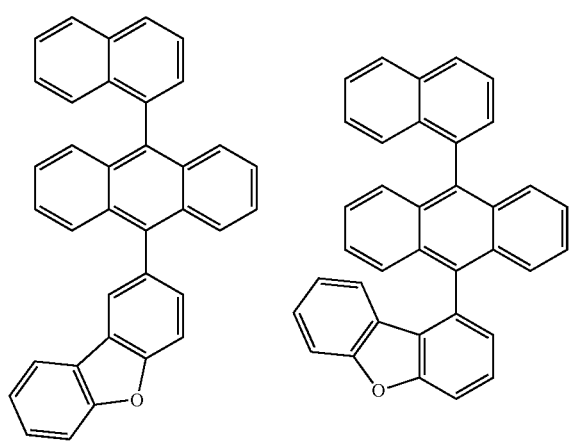
134
-continued
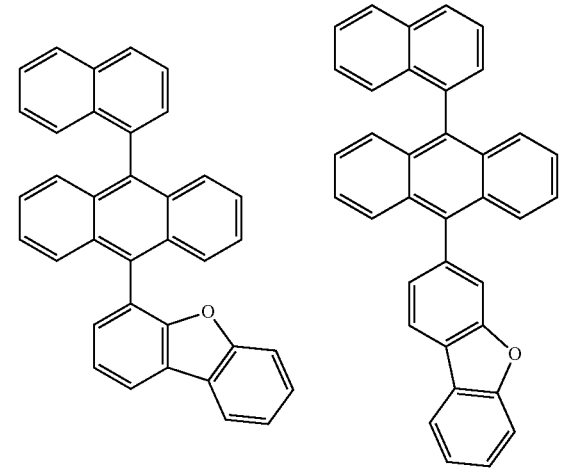

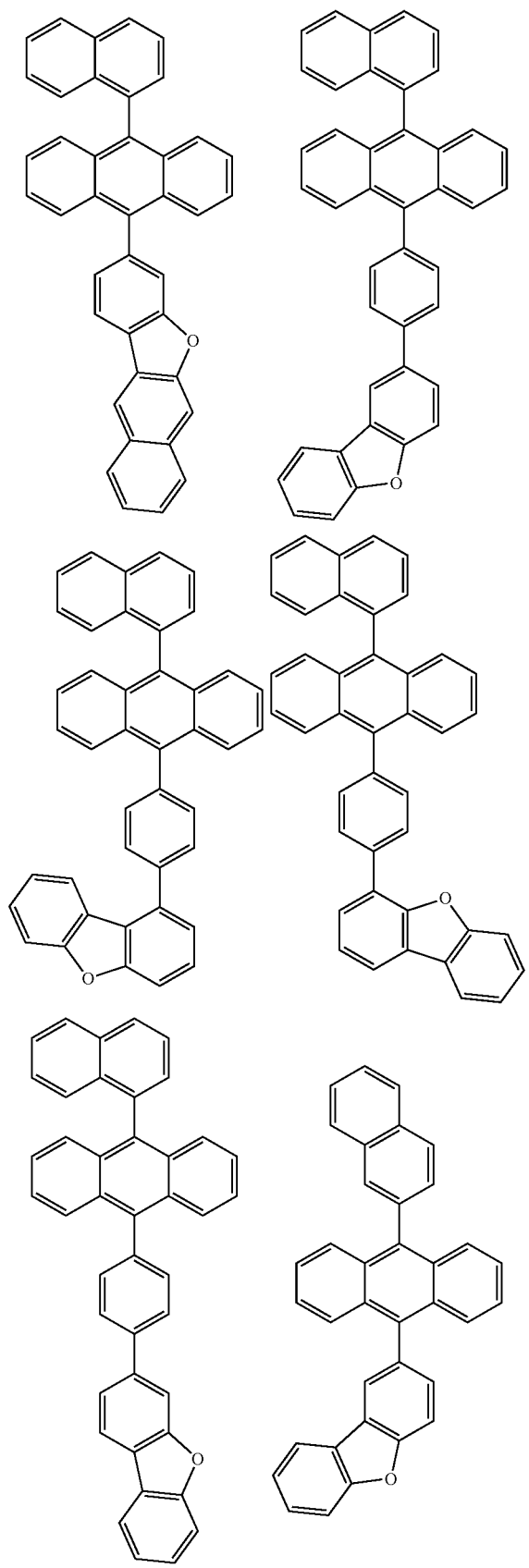
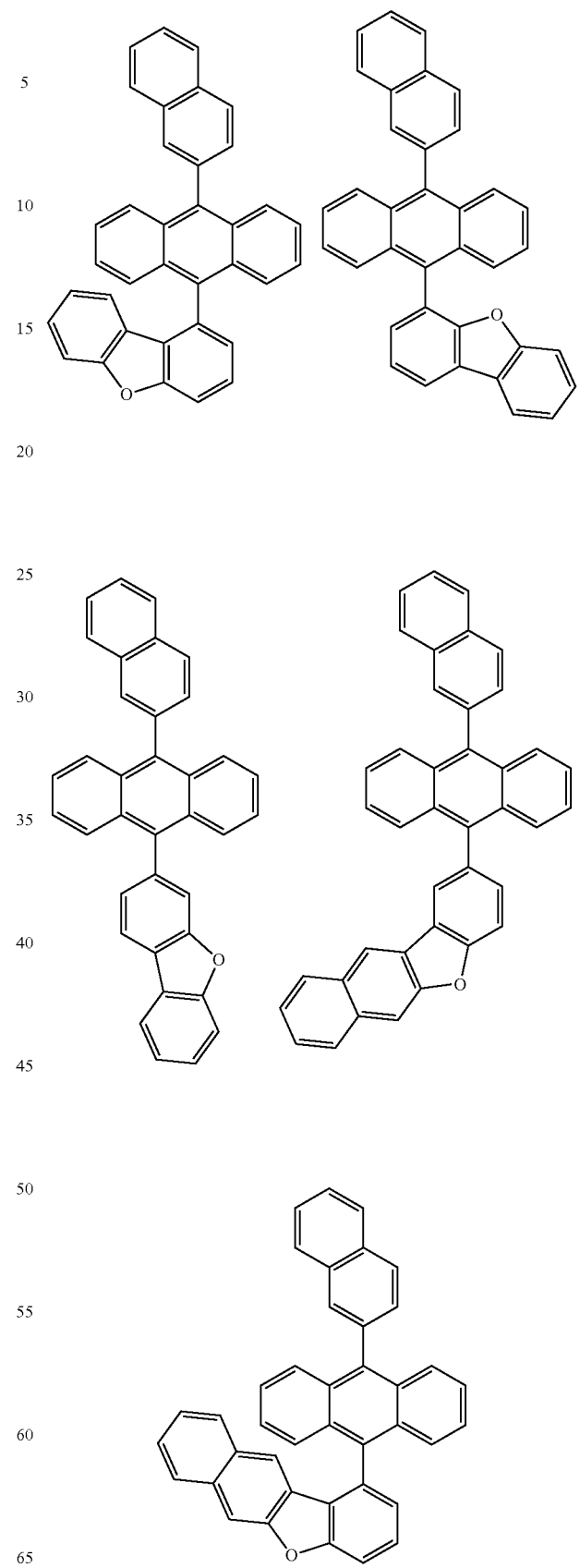

137
-continued

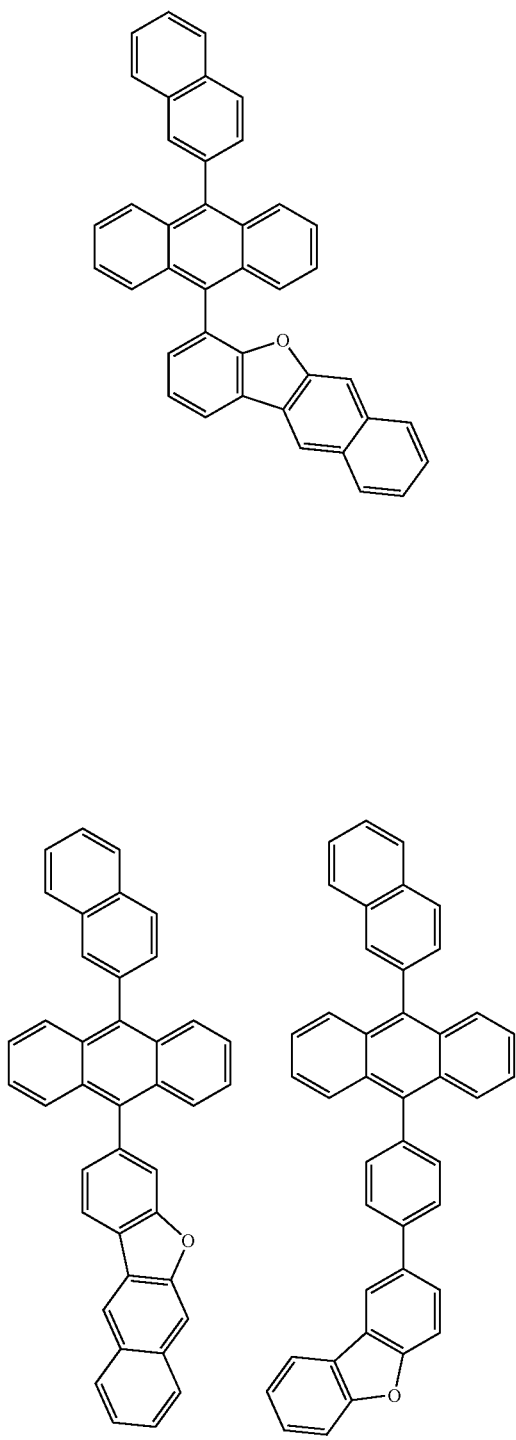

138
-continued

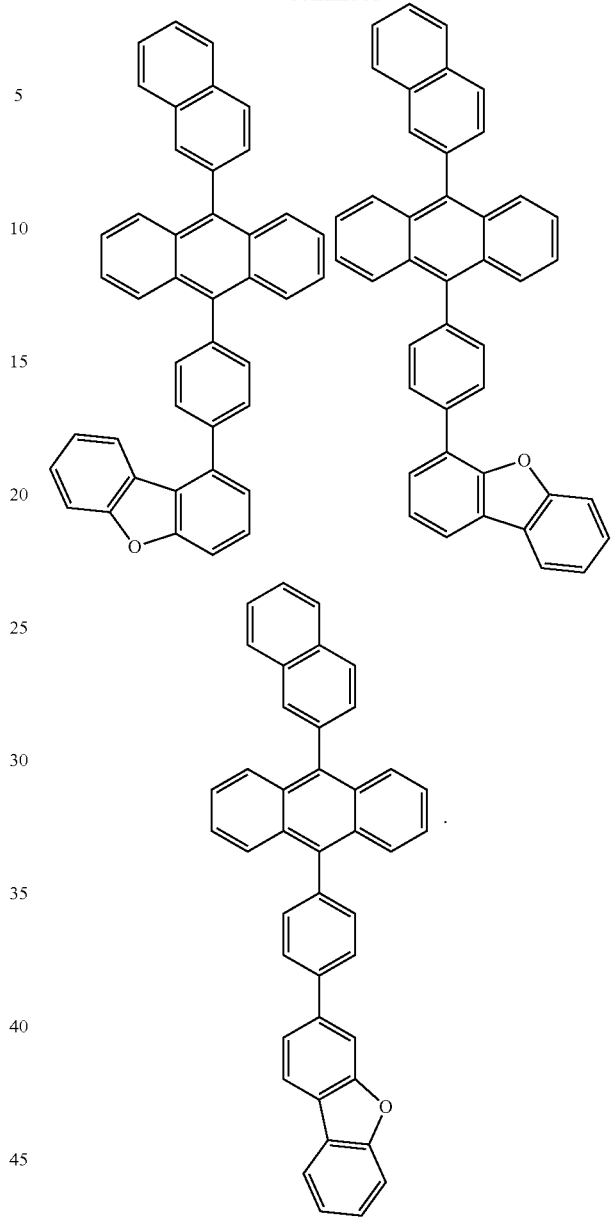

16. The organic light emitting device according to claim 10, wherein the one or more organic material layers comprise a hole injection layer, a hole transport layer, a light emission layer, or an electron transport layer light emission layer, and at least one of the hole injection layer, the hole transport layer, the light emission layer, or the electron transport layer light emission layer comprises the compound.

* * * * *